(12) United States Patent
Moyle

(10) Patent No.: US 8,530,190 B1
(45) Date of Patent: Sep. 10, 2013

(54) DISULFIDE CROSSLINKED GLYCOPROTEIN HORMONE ANALOGS, AND THEIR PREPARATION AND USE

(75) Inventor: William R. Moyle, Piscataway, NJ (US)

(73) Assignee: Merck Serono SA, Coinsins, Vaud (CH)

( * ) Notice: Subject to any disclaimer, the term of this patent is extended or adjusted under 35 U.S.C. 154(b) by 639 days.

(21) Appl. No.: 09/104,400

(22) Filed: Jun. 25, 1998

Related U.S. Application Data

(60) Provisional application No. 60/050,784, filed on Jun. 25, 1997.

(51) Int. Cl.
| | | |
|---|---|---|
| *A61K 38/24* | (2006.01) | |
| *A61P 5/06* | (2006.01) | |
| *C07K 14/59* | (2006.01) | |
| *C07K 1/00* | (2006.01) | |
| *C07K 14/00* | (2006.01) | |
| *C07K 16/00* | (2006.01) | |
| *C07K 17/00* | (2006.01) | |
| *C07H 21/04* | (2006.01) | |
| *C12N 15/09* | (2006.01) | |
| *C12N 5/07* | (2010.01) | |
| *C12N 5/10* | (2006.01) | |
| *C12N 5/00* | (2006.01) | |
| *C12N 5/02* | (2006.01) | |
| *C12N 15/00* | (2006.01) | |

(52) U.S. Cl.
USPC ....... 435/69.4; 435/360; 435/320.1; 435/325; 530/398; 536/23.51

(58) Field of Classification Search
USPC .............. 435/69.1, 69.7; 530/398; 930/110, 930/260; 424/194.1, 198.1
See application file for complete search history.

(56) References Cited

U.S. PATENT DOCUMENTS 5,691,455 A * 11/1997 Grootenhuis et al. ........ 530/398

FOREIGN PATENT DOCUMENTS

| CA | 2188508 | * | 4/1997 |
| WO | WO 2006113452 A2 | * | 10/2006 |

OTHER PUBLICATIONS

J.C. Heikoop et al. Nature Biotechnology 15(7):658-662, 1997. Structure-based deisgn and protein engineering of intersubunit disulfide bonds in gonadotropins.*
Fairlie et al., (Biochem J. 1996. 314:449-455).*
Fox et al., (Mol Endocrin. 2001:15(3):378-389).*
Bousfeld et al., (Rev Endocr Metab Disord. 2011.12:289-302).*
Bernard et al., (Mol Cell Endo. 2005.233:25-31).*
Xing et al., (JBC. Aug. 20, 2004. 279(34):35458-35468).*
Bernard et al., (JBC. Oct. 22, 2004. 279(43):44438-44441).*
Xing et al., (JBC. Oct. 22, 2004. 279(43):44427-44437).*
Xing et al., (JBC. Dec. 14, 2001. 276(50):46953-46960).*
A.J. Lapthorn et al., "Crystal structure of human chorionic gonadotropin", *Nature*, 369:455-461, (1994).
Xia et al., "Identification of Conserved Amino Acid Residues in the B Subunit of Human Choriogonadotropin Important in Holoprotein Formation", *The Journal of Biological Chemistry*, 269 (27) 17944-17953, (1994).
Bedows et al, "Disulfide Bond Mutations Affect the Folding of the Human Chorionic Gonadotropin-Beta Subunit Transfected Chinese Hamster Ovary Cells*" J. Biol. Chem. 268:11655-11662 (1993).

(Continued)

*Primary Examiner* — Cherie M Stanfield
(74) *Attorney, Agent, or Firm* — Browdy and Neimark, PLLC

(57) ABSTRACT

The invention relates to analogs of glycoprotein hormones with an intersubunit disulfide crosslink and their preparation and use. Corresponding DNA sequences and host cells, as well as pharmaceutical compositions are also disclosed.

34 Claims, 32 Drawing Sheets

(56) References Cited

OTHER PUBLICATIONS

Bernard et al., Only a portion of the small seatbelt loop in human choriogonadotropin appears capable of contacting the lutropin receptor, The Journal of Biological Chemistry, 279(43): 44438-44441 (2004).
Bernard et al., Crosslinked bifuncational gonadotropin analogs with reduced efficacy, Molecular and Cellular Endocrinology, 233:25-31 (2005).
Braun et al, "Amino-terminal leucine-rich repeats in gonadotropin receptors determine hormone selectivity" EMBO. J. 10:1885-1890 (1991).
Campbell et al, "Conversion of human choriogonadotropin into a follitropin by protein engineering" Proc. Natl. Acad. Sci., USA 88:760-764 (1991).
Campbell et al, Chimeric proteins can exceed the sum of their parts: Implications for evolution and protein designNature Biotech. 15:439-443 (1997).
Cosowsky et al, "Influence of Subunit Interactions on Lutropin Specificity" J. Biol. Chem. 272:3309-3314 (1997).
Furuhashi et al, "Mutagenesis of Cysteine Residues in the Human Gonadotropin a Subunit" J. Biol. Chem. 269:25543-25548 (1994).
Han et al, "hCGB Residues 94-96 alter LH activity without appearing to make key receptor contacts" Mol. Cell. Endocrinol. 124:151-161 (1996).
Han et al, Erratum to "hCGBeta Residues 94-96 alter LH activity without appearing to make key receptor contacts" [Mol. Cell. Endocrinol. 124 (1996) 151 161F 129 (1997) 237-239.
Kriegler, M., Gene Transfer and Expression: A Laboratory Manual, Stockton Press, New York, pp. 96-98 (1990).
Lapthorn et al, "Crystal structure of human chorionic gonadotropin" Nature 369:455-461 (1994).
Matsumura et al, "Substantial Increase of protein stability by multiple disulphide bonds" Nature 342:291-293 (1989).
Matthews, B. W., "Perspectives in Biochemistry—Genetic and Structural Analysis of the Protein Stability Problem" Biochemistry 26:6885-6888 (1987).
Moyle et al, "Co-evolution of ligand-receptor pairs" Nature 368:251-255 (1994).
Moyle et al, "Model of Human Chorionic Gonadotropin and Lutropin Receptor Interaction That Explains Signal Transduction of the Glycoprotein Hormones*" J. Biol. Chem. 270:20020-20031 (1995).
Moyle et al, Endocrinology, "Gonadotropins" L. J. DeGroot, ed., Saunders, Philadelphia (1995), pp. 230-241.
Nagayama et al, "Thyrotropin-luteinizing hormone/chorionic gonadotropin receptor extracellular domain chimeras as probes for thyrotropin receptor function" Proc. Natl. Acad. Sci., USA 88:902-905 (1991).
Pierce et al, "Glycoprotein Hormones: Structure and Function" Ann. Rev. Biochem. 50:465-495 (1981).
Sugahara et al, Biosynthesis of a biologically active single peptide chain containing the human common alpha and chorionic gonadotropin beta subunits in tandem Proc. Natl. Acad. Sci., USA 92:2041-2045 (1995).
Suganuma et al, "Elimination of Disulfide Bonds Affects Assembly and Secretion of the Human Chorionic GonadotropinBeta Subunit*" J. Biol. Chem. 264:19302-19307 (1989).
Sun et al, "The Cystine-Knot Growth-Factor Superfamily" Annu. Rev. Biophys. Biomol. Struct. 24:269-291 (1995).
Weare et al, "Studies with Carbodiimide-cross-linked Derivatives of Bovine Lutropin: I. The Effects of Specific Group Modifications on Receptor Site Binding in Testes" J. Biol. Chem. 254:6964-6971 (1979).
Weare et al, "Studies with Carbodiimide-cross-linked Derivatives of Bovine Lutropin: II. Location of the Cross-Link and Implication for Interaction With the Receptors in Testes"J. Biol. Chem. 254:6972-6979 (1979).
Xing et al, Alternatively Folded Choriogonadotropin Analogs, The Journal of Biological Chemistry, 276(50) 46953-46960 (2001).
Xing et al., Glycoprotein Hormone Assembly in the Endoplasmic Reticulum: I. The Glycosylated end of Human $\alpha$-Subunit Loop 2 is Threaded Through a $\beta$-Subunit Hole, The Journal of Biological Chemistry, 279(34)35426-35436 (2004).
Xing et al., Glycoprotein hormone assembly in the endoplasmic reticulum: II. Multiple Roles of a Redox Sensitive $\beta$-Subunit Disulfide Switch, The Journal of Biological Chemistry, 279(34)35437-35448 (2004).
Xing et al., Glycoprotein Hormone Assembly in the Endoplasmic Reticulum: III. The Seatbelt and its Latch Site Determine the Assembly Pathway, The Journal of Biological Chemistry, 279(34)35449-35457 (2004).
Xing et al., Glycoprotein Hormone Assembly in the Endoplasmic Reticulum: IV. Probable Mechanism of Subunit docking and Completion of Assembly, The Journal of Biological Chemistry, 279(34)35458-35468 (2004).
Xing et al., Use of protein knobs to characterize the position of conserved $\alpha$-subunit regions in lutropin receptor complexes, The Journal of Biological Chemistry, 279(43)44427-44437 (2004).

* cited by examiner

α:

mdyyrkyaaiflvtlsvflhvlhsapdvqdcpectlqenpffsqpgapilqcmgccfsrayptplrskktmlvqk
nvtsestccvaksynrvtvmggfkvenhtachcstcyyhks

mdyyrkyaaiflvtlsvflhvlhsapdvqdSpectlqenpffsqpgapilqcmgccfsrayptplrskktmlvq
knvtsestccvaksynrvtvmggfkvenhtachcstcyyhks

FIGURE 3B hCGβ':

memfqgllllllllsmggtwaskeplrprcrpinatlavekegcpvcitvntticagycptmtrvlqgvlp
alpqvvcnyrdvrfesirlpgcprgvnpvvsyavalscqcalcrrsttdcggpkdhpltcddprfqdsss
skapppslpspsrlpgpsdtpilpq

FIGURE 4A hCGβ'Y37C:

memfqgllllllllsmggtwaskeplrprcrpinatlavekegcpvcitvntticagCcptmtrvlqgvlp
alpqvvcnyrdvrfesirlpgcprgvnpvvsyavalscqcalcrrsttdcggpkdhpltcddprfqdsss
skapppslpspsrlpgpsdtpilpq

FIGURE 4B

CFC101-114β':

memfqglllllllsmggtwaskeplrprcrpinatlavekegcpvcitvntticagycptmtrvlqgvlp
alpqvvcnyrdvrfesirlpgcprgvnpvvsyavalscqcalcrrsttdc<u>tvrglqpsycsfqe</u>fqdsss
skapppslpspsrlpgpsdtpilpq

FIGURE 10A

CFC101-114βY37C:

memfqglllllllsmggtwaskeplrprcrpinatlavekegcpvcitvntticagCcptmtrvlqgvlp
alpqvvcnyrdvrfesirlpgcprgvnpvvsyavalscqcalcrrsttdc<u>tvrglqpsycsfqe</u>fqdsss
skapppslpspsrlpgpsdtpilpq

mdyyrkyaaiflvtlsvflhvlhsapdvqdcpectlqenpffsqpgapilqcmgccfsrayptplrskktmlvq
Cnvtsestccvaksynrvtvmggfkvenhtachcstcyyhks

FIGURE 15A hCGβ'D99C:

memfqgllllllsmggtwaskeplrprcrpinatlavekegcpvcitvntticagycptmtrvlqgvlp
alpqvvcnyrdvrfesirlpgcprgvnpvvsyavalscqcalcrrsttCcggpkdhpltcddprfqdsss
skapppslpspsrlpgpsdtpilpq

FIGURE 15B memfqgllllllllsmggtwaskeplrprcrpinatlavekegcpvcitvntticagycptmtrvlqgvlp
alpqvvcnyrdvrfesirlpgcprgvnpvvsyavalscqcalcrrsttCc<u>tvrqlqpsycsfqe</u>fqdsss
skapppslpspsrlpgpsdtpilpq

αC7S, K51C:

mdyyrkyaaiflvtlsvflhvlhsapdvqdSpectlqenpffsqpgapilqcmgccfsrayptplrskktmlvq
Cnvtsestccvaksynrvtvmggfkvenhtachcstcyyhks hCGβ'Y37C,D99C:

memfqglllllllsmggtwaskeplrprcrpinatlavekegcpvcitvntticagCcptmtrvlqgvlp
alpqvvcnyrdvrfesirlpgcprgvnpvvsyavalscqcalcrrsttCcggpkdhpltcddprfqdsss
skapppslpspsrlpgpsdtpilpq

αC7A:

mdyyrkyaaiflvtlsvflhvlhsapdvqdApectlqenpffsqpgapilqcmgccfsrayptplrskktmlvq
knvtsestccvaksynrvtvmggfkvenhtachcstcyyhks

FIGURE 32A hFSHβY31C mktlqffflfllwkaiccnsceltnitiavekegcgfcitinttwcagCcytrdlvykdparpkiqktctfkel
vyetvrvpgcahhadslytypvatqchcgkcdsdstdctvrglgpsycsfgemke

FIGURE 32B

| Desired Amino Acid | | Permitted Codons |
|---|---|---|
| Alanine | (A) | GCA, GCC, GCG, GCT |
| Cysteine | (C) | TGC, TGT |
| Aspartate | (D) | GAC, GAT |
| Glutamate | (E) | GAA, GAG |
| Phenylalanine | (F) | TTC, TTT |
| Glycine | (G) | GGA, GGC, GGG, GGT |
| Histidine | (H) | CAG, CAT |
| Isoleucine | (I) | ATA, ATC, ATT |
| Lysine | (K) | AAA, AAG |
| Leucine | (L) | CTA, CTC, CTG, CTT, TTA, TTG |
| Methionine | (M) | ATG |
| Asparagine | (N) | AAC, AAT |
| Proline | (P) | CCA, CCC, CCG, CCT |
| Glutamine | (Q) | CAA, CAG |
| Arginine | (R) | CGA, CGC, CGG, CGT, AGA, AGG |
| Serine | (S) | AGC, AGT, TCA, TCC, TCG, TCT |
| Threonine | (T) | ACA, ACC, ACG, ACT |
| Valine | (V) | GTA, GTC, GTG, GTG |
| Tryptophan | (W) | TGG |
| Tyrosine | (Y) | TAC, TAT |
| Termination | | TAA, TAG, TGA |

mdyyrkyaaiflvtlsvflhvlhsapdvCdcpectlqenpffsqpgapilqcmgccfsrayptplrskktmlvq
knvtsestccvaksynrvtvmggfkvenhtachcstcyyhks

FIGURE 34A hCGβR8C:

memfqglllllllsmggtwaskeplrpCcrpinatlavekegcpvcitvntticagycptmtrvlqgvlpalpq
vvcnyrdvrfesirlpgcprgvnpvvsyavalscqcalcrrsttdcggpkdhpltcddprfqdsssskapppslp
spsrlpgpsdtpilpq

FIGURE 34B mktlqffflfllwkaiccnCceltnitiavekegcgfcitinttwcagycytrdlvykdparpkiqktctfkel
vyetvrvpgcahhadslytypvatqchcgkcdsdstdctvrglgpsycsfgemke

FIGURE 35 memlqglllllllsmggawasreplrpwchpinailavekegcpvcitvntticagCcptmmrvlqavlpplpq
vvctyrdvrfesirlpgcprgvdpvvsfpvalscrcgpcrrstsdcggpkdhpltcdhpqlsgllfl

FIGURE 36 memlqglllllllsmggawasreplrpCchpinailavekegcpvcitvntticagycptmmrvlqavlpplpq
vvctyrdvrfesirlpgcprgvdpvvsfpvalscrcgpcrrstsdcggpkdhpltcdhpqlsgllfl

FIGURE 37 mtalflmsmlfglacgqamsfcipteymthierrecaycltintticagCcmtrdingklflpkyalsqdvcty
rdfiyrtveipqcplhvapyfsypvalsckcgkcntdysdciheaiktnyctkpqksy

FIGURE 38 mtalflmsmlfglacgqamsCcipteymthierrecaycltintticagycmtrdingklflpkyalsqdvcty
rdfiyrtveipqcplhvapyfsypvalsckcgkcntdysdciheaiktnyctkpqksy

FIGURE 39

```
hCG   SKEPLRPRCRPINATLAVEKEGCPVCITVNTTICAGYCPTHTRV..LQGVLPALPQVVCNYRDVRFESIRLPGCPRGVNPVVSYAVALSCQCALCRRSTTDCGGPKDHPLTCDDPRFQDSSSSKAPPPSLPSPSRLPGPSDTPILPQ
hLH   SREPLRPWCHPINAILAVEKEGCPVCITVNTTICAGYCPTHMRV..LQAVLPPLPQVVCTYRDVRFESIRLPGCPRGVDPVVSFPVALSCRCGPCRRSTSDCGGPKDHPLTCDHPQLSGLLFL..........................
hFSH  .....NSCELTNITIAVEKEGCGFCITINTTWCAGYCYTRDLV..YKDPARPKIQKTCTFKELVYETVRVPGCAHHADSLYTYPVATQCHCGKCDSDSTDCTVRGLGPSYCSFGEMKE............................
hTSH  ......FCIPTEYMTHIERRECAYCLTINTTICAGYCMTRDINGKLFLPKYALSQDVCTYRDFIYRTVEIPQCPLHVAPYFSYPVALSCKCGKCNTDYSDCIHEAIKTNYCTKPQKSY.............................
```

FIG. 47

| | |
|---|---|
| Human | ....APDVQDCPECTLQENPFFSQPGAPILQCMGCCFSRAYPTPLRSKKTMLVQKNVTSESTCCVAKSYNRVTVMGGFKVENHTACHCSTCYYHKS |
| Ovine | FPDGEFTMQGCPECKLKENKYFSKPDAPIYQCMGCCFSRAYPTPARSKKTMLVPKNITSEATCCVAKCCVAKAFTKATVMGNVRVENHTECHCSTCYYHKS |
| Porcine | FPDGEFTMQGCPECKLKENKYFSKLGAPIYQCMGCCFSRAYPTPARSKKTMLVPKNITSEATCCVAKAFTKATVMGNARVENHTECHCSTCYYHKS |
| Bovine | FPDGEFTMQGCPECKLKENKYFSKPDAPIYQCMGCCFSRAYPTPARSKKTMLVPKNITSEATCCVAKAFTKATVMGNVRVENHTECHCSTCYYHKS |
| Equine | FPDGEFTMQGCPECKLRENKYFFKLGVPIYQCKGCCFSRAYPTPARSRKTMLVPKNITSESTCCVAKAFIRVTVMGNIKLENHTQCYCSTCYHHKI |
| Rat | FPDGEFTTQDCPECKLKENKYFSKLGAPIYQCMGCCFSRAYPTPARSKKTMLVPKNITSEATCCVAKSFTKATVMGNARVENHTKCHCSTCYYHKS |
| Mouse | LPDGDLIIQGCPECKLKENKYFSKLGAPIYQCMGCCFSRAYPTPARSKKTMLVPKNITSEATCCVAKAFTKATVMGNARVENHTECHCSTCYYHKS |
| Rabbit | LPDGDFIIQGCPECKLKENKYFSKLGAPIYQCMGCCFSRAYPTPARSKKTMLVPKNITSEAGCCVAKAFTKATVMGNAKVENHTECHCSTCYYHYS |
| Chicken | FPDGEFAMQGCPECKLKENRFFSKPGAPIYQCTGCCFSRAYPTPMRSKKTMLVPKNITSEATCCVAKAFTKITLKDNVRIENHTECHCSTCYYHYS |
| Carp-1 | FPDGEFLMQGCPECKLKENKYFSKPGAPVYQCMGCCFSRAYPTPLRSKKTMLVPKNITSEATCCVAKEVKKILVNDV.KLVNHTDCHCSTCYYHKS |
| Carp-2 | YPRNDMNNFGCEECKLKENNIFSKPGAPVYQCMGCCFSRAYPTPLRSKKTMLVPKNITSEATCCVAKEFKQVLVNDI.KLVNHTDCHCSTCYYHKS |
| Eur. Eel | YPRNYMNNFGCEECTLKENNIFSKPGAPVYQCMGCCFSRAYPTPLRSKKTMLVPKNITSEATCCVAREFQVLVNDI...DNMKLENHTDCGGSTCYYHKF |
| Pike eel | YPNNEMARGGCDECRLQENKIFSKPSAPIFQCVGCCFSRAYPTPLRSKKTMLVPKNITSEATCCVAREVTRL...DNMKLENHTDCHCSTCYYHKS |
| Salmon-1 | YPNNEISRGGCDECRLKDNKFFSKPSAPIFQCVGCCFSRAYPTPLRSKKTMLVPKDITSEATCCVAREVTKL...DNMKLENHTDCHCSTCYYHKS |
| Salmon-2 | YQNSDMTNVGCEECKLKENKVFSNPGAPVLQCTGCCFSRAYPTPLQSKKAMLVPKNITSEATCCVAKEGERV.VVDNIKLTNHTECWCNTCYHHKS |
| Salmon-2 | YPNSDKTNMGCEECKLKPNTIFPNPGAPIMQCTGCCFSRAYPTPLRSKQTMLVPKNITSEATCCVAKEGERVTTKDGFPVTNHTECHCSTCYYHKS |

DISULFIDE CROSSLINKED GLYCOPROTEIN HORMONE ANALOGS, AND THEIR PREPARATION AND USE

CROSS-REFERENCE TO RELATED APPLICATIONS

The present application claims priority from U.S. provisional application Ser. No. 60/050,784, filed Jun. 25, 1997, the entire contents of which are hereby incorporated by reference.

GOVERNMENT LICENSING RIGHTS

The experiments in this application were supported by the National Institutes of Health, Grant Nos. HD14907 and DK50600. The U.S. Government has a paid-up license in this invention and the right in limited circumstances to require the patent owner to license others on reasonable terms as provided by the terms of Grant Nos. HD14907 and DK50600 awarded by the National Institutes of Health.

BACKGROUND OF THE INVENTION

1. Field of the Invention

The present invention relates to analogs of glycoprotein hormones and their preparation and use. More specifically, the invention relates to disulfide bond crosslinked analogs of the glycoprotein hormones and their preparation and use.

2. Description of the Related Art

The glycoprotein hormones include the hormones chorionic gonadotropin (CG) also known as choriogonadotropin, luteinizing hormone (LH) also known as lutropin, follicle stimulating hormone (FSH) also known as follitropin, and thyroid stimulating hormone (TSH) also known as thyrotropin. Those from humans are known as human chorionic gonadotropin (hCG), human luteinizing hormone (hLH), human follicle stimulating hormone (hFSH), and human thyroid stimulating hormone (hTSH). These hormones have important roles in gonadal and thyroid function (Pierce et al, 1981, Moyle et al, 1995). CG and LH bind to and stimulate LH receptors, FSH binds to and stimulates FSH receptors, and TSH binds to and stimulates TSH receptors. CG is a hormone produced in large quantities primarily by the placentas of a few mammals including those of primates. The amino acid sequences of the β-subunits of CG from primates usually differ from those of LH. Equines also produce a CG, however, this has the same amino acid sequence as equine LH (Murphy et al, 1991).

As reviewed by Pierce et al (1981), the glycoprotein hormones are heterodimers consisting of an α- and a β-subunit. The heterodimers are not covalently linked together and their subunits can be dissociated by treating the hormones with acid or urea (Pierce et al, 1981). Most higher vertebrates contain only one gene that encodes the α-subunit (Fiddes et al, 1984); the same α-subunit normally combines with the β-subunits of LH, FSH, TSH, and, when present, CG. Nonetheless, post-translational protein processing, notably glycosylation (Baenziger et al, 1988), can contribute to differences in the compositions of the α-subunits of LH, FSH, TSH, and CG. Most of the amino acid sequence differences between the hormones reside in their hormone-specific β-subunits (Pierce et al, 1981). These are produced from separate genes (Fiddes et al, 1984, Bo et al, 1992).

With few exceptions (Blithe et al, 1991), the α-β-heterodimers have much more hormonal activity than either free subunit (Pierce et al, 1981). The naturally occurring α- and β-subunits form α,β-heterodimers much better than they form α,α-homodimers or -homodimers. Indeed, expression of hCG α-subunit and β-subunit genes together in mammalian cells leads to the formation of α-β-heterodimers, α-subunit monomers, and β-subunit monomers. Only trace amounts, if any, of the α,α-homodimer or -homodimer are made or secreted from the cells.

High-resolution X-ray crystal structures of human chorionic gonadotropin (hCG) have been reported by two laboratories (Lapthorn et al, 1994; Wu et al, 1994). These structures revealed that the original proposed disulfide bond patterns (Mise et al, 1980 and 1981) were incorrect and that the hormone is a member of the cysteine knot family of proteins (Sun et al, 1995). Since the relative locations of the cysteines in all glycoprotein hormones are similar, they are likely to have the cysteine knot architecture found in hCG.

The locations of the cysteine residues in the α-subunits of the vertebrate glycoprotein hormones are similar (FIGS. 1A and 1B). Using the hCG α-subunit as a model, it is seen that the cysteine knot is formed by the second, third, fifth, seventh, eighth, and ninth α-subunit cysteines. This creates three large α-subunit loops (FIGS. 1A and 1B). Loop 1 is the sequence of amino acids between the second and third cysteines; loop 2 is the sequence of amino acids between the fifth and seventh α-subunit cysteines; and loop 3 is the sequence of amino acids between the seventh and eighth cysteines. The locations of the cysteine residues in the β-subunits of the vertebrate glycoprotein hormones are similar (Pierce et al, 1981). Using the hCG β-subunit as a model, it is seen that the cysteine knot is formed by the first, fourth, fifth, sixth, eighth, and ninth cysteines. This creates three large β-subunit loops (FIGS. 2A and 2B). Loop 1 is the sequence of amino acids between the first and fourth cysteines; loop 2 is the sequence between the fifth and sixth cysteines; and loop 3 is the sequence between the sixth and eighth cysteines. By replacing portions of the α-subunit with homologous portions of another α-subunit or by replacing portions of the β-subunit with homologous portions of another β-subunit, it is possible to prepare functional chimeras of each glycoprotein hormone subunit (Campbell et al, 1991; Moyle et al, 1990; Moyle et al, 1994; Cosowsky et al, 1995; Moyle et al, 1995; Cosowsky et al, 1997). A general schematic of the structural elements in glycoprotein hormone subunits is presented in FIG. 1C, and the correspondence with human glycoprotein hormone subunits by amino acid residues is shown below in Table 1A.

TABLE 1A

Correspondence of Human Hormone Subunit Amino Acid Sequences to Structural Elements Depicted in FIG. 1C

| | N-term | | Loop 1 | | Loop 2 | | Loop 3 | | C-term/ Seat-Belt | | Cys-Knot |
|---|---|---|---|---|---|---|---|---|---|---|---|
| α | 1-6 | α | 11-27 | α | 33-59 | α | 61-81 | α | 85-92 | α | 10, 28-32, |
| CGβ | 1-8 | CGβ | 10-33 | CGβ | 39-56 | CGβ | 58-87 | CGβ | 91-145 | | 60, 82-84 |

TABLE 1A-continued

Correspondence of Human Hormone Subunit Amino Acid Sequences to Structural Elements Depicted in FIG. 1C

| N-term | Loop 1 | Loop 2 | Loop 3 | C-term/<br>Seat-Belt | Cys-Knot | |
|---|---|---|---|---|---|---|
| LHβ 1-8 | LHβ 10-33 | LHβ 39-56 | LHβ 58-87 | LHβ 91-end | CGβ | 9, 34-38,<br>57, 88-90 |
| FSHβ 1-2 | FSHβ 4-27 | FSHβ 33-50 | FSHβ 52-81 | FSHβ 85-111 | | |
| TSHβ 1 | TSHβ 3-26 | TSHβ 32-51 | TSHβ 53-82 | TSHβ 86-end | LHβ | 9, 34-38,<br>57, 88-90 |
| | | | | | FSHβ | 3, 28-32,<br>51, 82-84 |
| | | | | | TSHβ | 2, 27-31,<br>52, 83-85 |

In addition to its cysteine knot, the β-subunit also contains a sequence termed the seat-belt (Lapthorn et al, 1994) that is wrapped around the second α-subunit loop. The seat-belt begins at the ninth cysteine, the last residue in the β-subunit cysteine knot, and includes the tenth, eleventh, and twelfth cysteines. It is latched to the first β-subunit loop by a disulfide bond formed between cysteine twelve (i.e., at the carboxyl-terminal end of the seat-belt) and cysteine three (i.e., in the first β-subunit loop).

The seat-belt is a portion of the hCG β-subunit that has a significant (if not primary) influence on the ability of hCG to distinguish LH and FSH receptors (Campbell et al, 1991; Moyle et al, 1994). Replacement of all or parts of the hCG seat-belt amino acid sequence with the seat-belt sequence found in hFSH altered the receptor binding specificity of the resulting hormone analog. Normally, hCG binds LH receptors more than 1000-fold better than FSH or TSH receptors. However, analogs of hCG such as CF94-117 and CF101-109 in which hCG seat-belt residues 101-109 (i.e., Gly-Gly-Pro-Lys-Asp-His-Pro-Leu-Thr) (residues 101-109 of SEQ ID NO:2) are replaced with their hFSH counterparts (i.e., Thr-Val-Arg-Gly-Leu-Gly-Pro-Ser-Tyr) (residues 113-121 of SEQ ID NO:15) bound FSH receptors much better than hCG (Moyle et al, 1994). Further, by manipulating the composition of the seat-belt, it is possible to prepare analogs of hCG that have various degrees of LH and FSH activities (Moyle et al, 1994; Han et al, 1996). These have potential important therapeutic uses for enhancing fertility in males and females.

Most, but not all of the intrasubunit disulfide bonds of the glycoprotein hormones are essential for their biological activities. Studies in which individual cysteines have been replaced by other amino acids, notably alanine, have shown that all the disulfide bonds of the cysteine knots and the seat-belt are essential for folding of the heterodimer (Suganuma et al, 1989; Bedows et al, 1993; Furuhashi et al, 1994). The remaining disulfide bonds between human α-subunit cysteines 7-31 and 59-87 and between hCG β-subunit cysteines 23-72 are not essential for heterodimer formation or for hormone activity.

As yet there is no high-resolution crystal structure that describes the interaction of any glycoprotein hormone with its receptor. Several models have been built in an effort to describe the structure of the hormone receptor complex. Most of these are based on the crystal structures of hCG and ribonuclease inhibitor, a protein that may be similar in structure to the extracellular domains of the glycoprotein hormone receptors. Most efforts to identify hormone residues that contact the receptor have been based on the influence of chemical, enzymatic, or genetic mutations that lead to a reduction in receptor binding. Unfortunately, since reduction in binding could be caused by disruption of a specific contact or by a change in hormone conformation (Cosowsky et al, 1997), the effects of these changes are difficult, if not impossible to interpret. This has led to considerable disagreement in this field (Remy et al, 1996; Berger et al, 1996) and some investigators have concluded that it is not possible to determine the orientation of the hormone in the receptor complex (Blowmick et al, 1996).

Other approaches to determine the orientation of the hormone in the receptor complex rely on identifying regions of the hormone that do not contact the receptor. These remain exposed after the hormone has bound to the receptor and/or can be altered without disrupting hormone-receptor interactions. When these are mapped on the crystal structure of hCG (Lapthorn et al, 1994; Wu et al, 1994), it is possible to develop a hypothetical model of the way that hCG might interact with LH receptors (Moyle et al, 1995). This approach suggested that the hormone groove formed by the second α-subunit loop and the first and third β-subunit loops is involved in the primary receptor contact (Cosowsky et al, 1995). This would also explain why both subunits are needed for highest hormone-receptor binding (Pierce et al, 1981). The data that support this conclusion are discussed in the next several paragraphs. However, it should be noted that most, if not all other investigators in this field support a model in which the hormone is oriented very differently (Remy et al, 1996; Berger et al, 1996), even though these investigators were aware of the model just described (i.e., they cite the paper describing the model in which the primary receptor binding site was made by the hormone groove).

Many portions of hCG α-subunit that do not appear to contact the receptor can be replaced without disrupting binding to LH receptors. Some of these regions are clearly exposed in the hormone-receptor complex since they can also be recognized by monoclonal antibodies while hCG is bound to LH receptors (Moyle et al, 1990; Cosowsky et al, 1995; Moyle et al, 1995). For example, although the human and bovine α-subunits have very different amino acid sequences, heterodimers containing the bovine α-subunit and the hCG β-subunit bind rat and human LH receptors well (Cosowsky et al, 1997). These heterodimers are readily distinguished by most monoclonal antibodies that recognize epitopes on loops 1 and 3 of the α-subunit of hCG (Moyle et al, 1995). These observations show that the surfaces of human and bovine α-subunit loops 1 and 3 differ and suggest that this region of the hormone does not form key essential receptor contacts.

By comparing the abilities of monoclonal antibodies to recognize analogs of hCG in which parts of the α-subunit were derived from either the human or bovine proteins, it was possible to identify key α-subunit residues that participated in antibody binding (Moyle et al, 1995). Some monoclonal antibodies that recognize epitopes on the hCG α-subunit also bound to a fragment of the α-subunit that had been prepared by trypsin digestion and that lacked most of the second α-subunit loop (Lapthorn et al, 1994; Wu et al, 1994; Birken et al, 1986). This observation was also used to determine and/or confirm the binding sites of these antibodies (Moyle et al, 1995). Two monoclonal antibodies that recognize α-subunit epitopes and that are referred to as A105 and A407 (Moyle et al, 1995) bound to hCG when the hormone was complexed with LH receptors. Thus, the α-subunit residues recognized by these antibodies do not appear to contact the LH receptor (Moyle et al, 1995). The remainder of the α-subunit includes the second α-subunit loop and the C-terminus of the protein. Some of the residues in these highly conserved portions of the α-subunit may participate in receptor contacts.

Many portions of hCG β-subunit that do not appear to contact the LH receptor can also be replaced by mutagenesis without disrupting LH receptor binding. This includes hCG β-subunit loop 2. An analog of hCG in which residues of hCG β-subunit loop 2 were replaced with those normally found in hFSH β-subunit loop 2, termed CF39-58 (Campbell et al, 1991), was readily distinguished by monoclonal antibodies that recognized FSH but not hCG residues in β-subunit loop 2. This showed that the structure of the second subunit loop differed in this analog and in hCG. Nonetheless, this β-subunit analog combined with the α-subunit to form an α,β-heterodimer that interacted with LH receptors similar to hCG (Campbell et al, 1991). Thus, few, if any, residues in the second β-subunit loop of hCG appear to make essential direct LH receptor contacts. Similarly, the second β-subunit loop of hFSH does not appear to contact FSH receptors. Analogs of hCG β-subunit have been reported in which residues between the tenth β-subunit cysteine and the C-terminus or between residues 94-114 were replaced with the corresponding residues of hFSH. These analogs are named CF94-117 (Campbell et al, 1991) and CFC94-114 (Wang et al, 1994). Both bind to FSH receptors much better than to LH receptors even though they contain the entire sequence of hCG in the second β-subunit loop. Because the second β-subunit loop of hCG appears to have minimal influence on the ability of the hormone to bind to either LH or FSH receptors, it seems unlikely that it participates in essential high affinity contacts with the LH or FSH receptor. Further, the second β-subunit loop of hCG is located near the first and third α-subunit loops, a portion of the α-subunit that also does not appear to contact the receptor. Thus, it appears likely that the entire region of hCG that contains residues in the first and third α-subunit loops and the second β-subunit loop may not contact the receptor. As will be discussed later, it is thought that this portion of the hormone projects into a cavity created by the horseshoe shape of the extracellular domain of the receptor (Moyle et al, 1995).

Residues of the hCG β-subunit that do not participate in high affinity receptor contacts can also be recognized by monoclonal antibodies after the hormone has bound to LH receptors (Campbell et al, 1991; Moyle et al, 1990; Moyle et al, 1994; Cosowsky et al, 1995). These include portions of the hCG β-subunit found in loops 1 and 3 furthest from the α-subunit interface that can be recognized by antibodies such as B105, B108, B111, and B112. These antibodies bind hCG when it is complexed with LH receptors (Moyle et al, 1990; Cosowsky et al, 1995), demonstrating that these portions of the β-subunit loops 1 and 3 do not make essential receptor contacts. Other studies have shown that it is possible to remove residues between the N-terminus and the first cysteine and between the twelfth cysteine and the C-terminus of the hCG β-subunit without eliminating the ability of the hormone to bind to LH receptors (Huang et al, 1993). The remaining portion of the β-subunit includes the seat-belt. Few of these residues appear to make essential contacts needed for high affinity binding to LH or FSH receptors. For example, it was found that changing the residues in the seat-belt between the eleventh and twelfth cysteines had minimal, if any, effect on binding to LH receptors (Moyle et al, 1994). Changing residues between the tenth and eleventh cysteines had less than five-fold effect on FSH receptor binding (Moyle et al, 1994). Further, most residues in the seat-belt of equine LH (eLH) and equine CG (eCG) differ from FSH (Pierce et al, 1981; Murphy et al, 1991), yet these hormones bind well to the rat FSH receptor. Indeed, purified eLH binds at least 30% as well as hFSH to the rat FSH receptor in vitro (Moyle et al, 1994). The portions of the hCG β-subunit that remain unaccounted include the surfaces of loops 1 and 3 that are nearest the α-subunit interface. Thus, these are likely sites of the hormone that contact the receptor. Portions of the α-subunit can also be recognized by monoclonal antibodies when hCG is complexed with LH receptors. These include residues recognized by antibodies A105 and A407 (Moyle et al, 1995).

Other strategies for identifying regions of the glycoprotein hormones that interact with receptors involve the use of hormone analogs that recognize more than one receptor (Campbell et al, 1991; Moyle et al, 1994; Han et al, 1996; Campbell et al, 1997). Thus, it was possible to prepare analogs of hCG that bind to FSH and TSH receptors simply by changing the β-subunit seat-belt of hCG to that found in hFSH (Campbell et al, 1997). This analog contains no TSH-specific residues yet was capable of stimulating a TSH response to the same maximum level as TSH. By comparing the activities of several of these multifunctional analogs, it is possible to conclude that most seat-belt residues and nearly all of the second β-subunit loop are unlikely to form key essential high-affinity receptor contacts.

There are no reports of a crystal structure for any LH, FSH, or TSH receptor. However, the amino acid sequences of several glycoprotein hormone receptors are known (Moyle et al, 1994; McFarland et al, 1989; Loosfelt et al, 1989; Segaloff et al, 1990; Sprengel et al, 1990; Braun et al, 1991; Nagayama et al, 1991; Nagayama et al, 1989; Jia et al, 1991). These proteins appear to have extracellular, transmembrane, and intracellular domains. When expressed without the transmembrane or intracellular domains (Braun et al, 1991; Ji et al, 1991; Xie et al, 1990; Moyle et al, 1991), or in conjunction with other transmembrane domains (Moyle et al, 1991), the extracellular domain is seen to contribute most of the affinity of the receptor for its ligand. The extra-cellular domains of these proteins are members of the leucine-rich repeat family of proteins and the transmembrane domains appear to have seven hydrophobic helices that span the plasma membrane (McFarland et al, 1989). A crystal structure of ribonuclease inhibitor, a model structure of one leucine-rich repeat protein has been determined and shown to have a horseshoe shape (Kobe et al, 1993 and 1995). This finding suggested that the extracellular domains of the LH, FSH, and TSH receptors are horseshoe-shaped (Moyle et al, 1995). Portions of the extracellular domain of the LH and FSH receptors that control their hCG and hFSH binding specificity have been identified through the use of LH/FSH receptor chimeras (Moyle et al, 1994). By considering the portions of hCG most likely to contact the LH receptor and the portions of the LH receptor that are responsible for ligand binding specificity, a model was developed that explains the abilities of this hormone to interact with LH receptors and to elicit signal transduction (Moyle et al, 1995). In this model, the groove between the second α-subunit loop and the first and third β-subunit loops contacts the rim of the receptor extracellular domain near the middle of the horseshoe (Moyle et al, 1995). The remainder of the hormone projects into the space between the arms of the horseshoe. When the hormone binds to the receptor and projects into this space, it stabilizes a conformation of the extracellular domain needed for signal transduction. This is conducted to the transmembrane domain by specific contacts between the extra-cellular and transmembrane domains needed for proper receptor expression on the cell surface (Moyle et al, 1991). The model accounts for the abilities of the oligosaccharides to influence signal transduction (Moyle et al, 1975; Matzuk et al, 1989). However, while the model can explain these data, other models in which different parts of hCG interact with the receptors have been proposed (Jiang et al, 1995). Thus, it is still unclear as to how the glycoprotein hormones interact with their receptors.

This view of hormone receptor interaction also explains the inhibition of hCG binding by some monoclonal antibodies that recognize regions of hCG thought not to participate in key receptor contacts. As discussed earlier, these include the hormone surface formed by α-subunit loops 1 and 3 and β-subunit loop 2. In the model, these regions project into a space between the N- and C-terminal arms of the receptor extracellular domain. Binding of antibodies to these sites prevents the hormone from entering this space.

Similarities in the locations of the cysteines in glycoprotein hormones from most vertebrate species (Pierce et al, 1981) suggest that they will fold like hCG. The structures of the receptors for the glycoprotein hormones are also likely to be quite comparable due to similarities in the leucine-rich repeats of their extracellular domains and the large number of conserved residues in their transmembrane domains (Moyle et al, 1994; Braun et al, 1991; Nagayama et al, 1991). Thus, it seems likely that any model that successfully explains the interaction of hCG with LH receptors will also predict the abilities of the other glycoprotein hormones to interact with their receptors. One way that the seat-belt can influence the specificity of ligand-receptor interaction would be to alter the relative positions of the hormone subunits (Cosowsky et al, 1997). This would change the shape of the groove between the second α-subunit loop and the first and third β-subunit loops. The suggestion has been made that inhibitory elements in the hormone and the receptor are responsible for preventing inappropriate ligand-receptor interactions (Moyle et al, 1994). Therefore, the effect of the seat-belt would be to alter the shape of the hormone to reduce its ability to fit into the central portion of the horseshoe.

The glycoprotein hormones have several therapeutic uses. FSH is used to induce development of ovarian follicles in preparation for ovulation induction in females (Galway et al, 1990; Shoham et al, 1991; Gast, 1995; Olive, 1995). LH and hCG are also used to induce ovulation of follicles that have initiated development. FSH, LH, and hCG are used to induce testis function in males. While the existing hormones can be used to stimulate the functions of the male and female gonads and the thyroid gland, practical application of the hormones for this use requires that they be heterodimers. These can be isolated from the pituitary gland (i.e., LH and FSH), serum (equine chorionic gonadotropin), or urine from pregnant (hCG) or postmenopausal women (mixtures of hLH and hFSH). Active heterodimers can also be isolated from cultures of cells that express both the α- and β-subunits including some from tumors (Cole et al, 1981) or those that have been transfected with cDNA or genomic DNA that encode the α- and β-subunits (Reddy et al, 1985). Indeed, the latter are an important source of glycoprotein hormones that have therapeutic utility. Because the oligosaccharides of the glycoprotein hormones have been shown to influence their abilities to elicit signal transduction (Moyle et al, 1975; Matzuk et al, 1989), preparation and synthesis of active heterodimers is best carried out in eukaryotic cells. These cells are capable of adding high mannose oligosaccharides to oligosaccharides and, in some cases, processing them to give the complex oligosaccharides that are found in the natural hormones (Baenziger et al, 1988). Nonetheless, because eukaryotic cells can process glycoproteins differently, synthesis of glycoprotein hormones is often carried out in mammalian cell lines such as that derived from the Chinese hamster ovary (CHO). While the hormones can be made in non-mammalian eukaryotic cells, the potential antigenicity of the oligosaccharide chains limits their clinical use.

The heterodimeric hormones have also been used as immunogens to elicit antisera that can be used to limit fertility (Singh et al, 1989; Pal et al, 1990; Talwar et al, 1986; Talwar et al, 1992; Moudgal et al, 1971 and 1972; Moudgal, 1976; Ravindranath et al, 1990; Moudgal et al, 1978). Due to the essential roles of hCG in maintaining human pregnancy, development of an immune response to hCG would be useful as a means of contraception and a substantial effort has been made to devise an hCG-based contraceptive vaccine. However, in principle, antibodies to the hormones could also be used to promote fertility. For example, LH levels appear to be excessive in some women who have polycystic ovarian disease. Thus, development of a method that would reduce but not eliminate circulating LH activity would be beneficial in restoration of fertility.

Glycoprotein hormone metabolism is very poorly understood. The half-lives of the hormones are known to be influenced by their content of oligosaccharides (Baenziger et al, 1988), particularly their terminal sugar residues. The most stable hormones are those that have the highest content of sialic acid in this location (Murphy et al, 1991; Baenziger et al, 1992; Fiete et al, 1991; Smith et al, 1993; Rosa et al, 1984). Nonetheless, the oligosaccharides are not entirely responsible for the stability of the hormones since the free hormone subunits are known to have significantly shorter circulating half-lives even though they have the same oligosaccharides as the heterodimers (Wehmann et al, 1984; Kardana et al, 1991). Indeed, it has been proposed that the hormones may be inactivated by proteolysis that leads to subunit dissociation (Kardana et al, 1991; Birken et al, 1991; Cole et al, 1991; Cole et al, 1991; Cole et al, 1993). Nicked hCG dissociated into its inactive subunits much faster than hCG (Cole et al, 1993). Thus, it is expected that a procedure that can prevent or reduce subunit dissociation would potentiate hormone efficacy.

The glycoprotein hormone subunits dissociate rapidly in denaturing conditions that include heat-treatment, extremes of pH, and urea (Pierce et al, 1981; Cole et al, 1993). For this reason, most glycoprotein hormone preparations are stored as lyophilized powders. A procedure that leads to enhanced stability of the heterodimer may enable hormone preparations to be stored and distributed in aqueous solutions. This would eliminate the need for shipping of separate hormone diluent and the additional step of hormone reconstitution by the end user.

Several attempts have been made to stabilize the hormones by "crosslinking" their subunits. Chemical crosslinking methods have been used (Weare et al, 1979 and 1979); however, these lead to reduced activity. It is also possible to genetically fuse the β- and α-subunits together to produce a single chain hormone. This molecule is more stable than the heterodimer and has high biological activity (Sugahara et al, 1995); however, it is grossly dissimilar from the native molecule.

Another method of crosslinking proteins would be to tether them by means of a disulfide bond. This strategy occurs naturally to stabilize other proteins of the cysteine knot superfamily (Sun et al, 1995) and probably takes the place of the seat-belt. Furthermore, addition of disulfide bonds to proteins can enhance their stability, provided the addition of the disulfide bond does not increase the internal strain within the protein (Matthews, 1987; Matsumura et al, 1989). However, no efforts have been reported to stabilize the glycoprotein heterodimers by a disulfide bond although a comment has been made that suggests the introduction of a disulfide bond may decrease their activity (Han et al, 1996). This is most likely because these heterodimers are complex proteins having several disulfides. Addition of a cysteine to these has the potential to disrupt folding, resulting in non-functional proteins. In addition, it is not likely that one can use other cysteine knot proteins as a basis to predict the locations of disulfide bonds that would stabilize the glycoprotein hormones as the organization of the subunits in the other cysteine knot proteins is substantially different from that in the glycoprotein hormones (Sun et al, 1995).

Citation of any document herein is not intended as an admission that such document is pertinent prior art, or considered material to the patentability of any claim of the present application. Any statement as to content or a date of any document is based on the information available to the applicant at the time of filing and does not constitute an admission as to the correctness of such a statement.

SUMMARY OF THE INVENTION

It is, accordingly, an object of the invention to overcome the deficiencies in the art as discussed above.

The present invention provides for analogs of glycoprotein hormones which stabilize the heterodimer of α- and β-subunits by forming an intersubunit disulfide bond between modified subunits. These analogs of the present invention retain at least a portion of the bioactivity of the corresponding glycoprotein hormone for its native glycoprotein hormone receptor, and when prepared in a pharmaceutical composition can be used to treat infertility or to limit fertility in a patient in need thereof. The heterodimer of the analogs of the present invention are stable to transport and storage as a liquid pharmaceutical formulation.

It has been discovered by the present inventor that the glycoprotein hormone analogs preferably fit the rule whereby the intersubunit crosslinks must be placed within two residues of existing (native) cysteines involved in native disulfide bonds and not outside the outermost cysteines of the corresponding native subunit.

Another aspect of the present invention is the provision of glycoprotein hormone analogs having an intersubunit disulfide crosslink between a cysteine knot of an α-subunit and a cysteine knot of a β-subunit. This minimizes perturbations to the glycoprotein hormone and permits it to substantially retain the activity of stimulating a gonadotropin receptor possessed by the corresponding native hormone, while conferring improved stability. The present invention further provides for recombinant DNA molecules containing nucleotide sequences encoding the α- and β-subunits of a glycoprotein hormone analog, which recombinant DNA molecules may be expression vectors. Eukaryotic host cells transformed with such recombinant DNA molecules are also provided for and used in a process for preparing the analogs of the present invention.

BRIEF DESCRIPTION OF THE DRAWINGS

FIGS. 3A and 3B show the translated amino acid of sequences of α (FIG. 3A) (SEQ ID NO:3) and αC7S (FIG. 3B) (SEQ ID NO:4) encoded by plasmids pSVL-α, pCI-α, pSVL-αC7S and pC7-αC7S. Since each translated protein has the same leader sequence, both are expected to be processed in the same way to create proteins consisting of 92 amino acids and having an N-terminal amino acid sequence beginning with APD. The single letter code used in this and other figures is: A, alanine (Ala); C, cysteine (Cys); D, aspartic acid (Asp); E, glutamic acid (Glu); F, phenylalanine (Phe); G, glycine (Gly); H, histidine (His); I, isoleucine (Ile); K, lysine (Lys); L, leucine (Leu); M, methionine (Met); N, asparagine (Asn); P, proline (Pro); Q, glutamine (Gln); R, arginine (Arg); S, serine (Ser); T, threonine (Thr); V, valine (Val); W, tryptophan (Trp); and Y, tyrosine (Tyr). The uppercase letter denotes the location of the Cys7 substitution by serine that formed C7S.

FIGS. 4A and 4B show the translated amino acid sequences of hCGβ' (FIG. 4A) (SEQ ID NO:5) and hCGβ'Y37C (FIG. 4B) (SEQ ID NO:6) encoded by plasmids pSVL-hCGβ' and pSVL-hCGβ'C7S. Since each has the same leader sequence, both are expected to be processed in the same way to create proteins consisting of 145 amino acids and having an N-terminal amino acid sequence beginning with SKE. The upper case letter refers to the location of the Tyr37 to cysteine mutation.

FIGS. 10A and 10B show the translated amino acid sequences of CFC101-114β' (FIG. 10A) (SEQ ID NO:7) and CFC101-114β'Y37C (FIG. 10B) (SEQ ID NO:8) encoded by plasmids pSVL-CFC101-114β and pSVLCFC101-114βY37C in the single letter amino acid code. Since each has the same leader sequence, both are expected to be processed in the same way to create proteins consisting of 145 amino acids having an N-terminal amino acid sequence beginning with SKE. The location of the upper case letter indicates the location of the Tyr37 to cysteine mutation. The underlined sequences are derived from the hFSH β-subunit. The codons for residues Arg95-Ser96 form a BglII site and those for Val102-Arg103-Gly104 form an SstII site.

FIGS. 15A and 15B show the translated amino acid sequences of αKSIC (FIG. 15A) (SEQ ID NO:9) and hCGβD99C (FIG. 15B) (SEQ ID NO:10) encoded by plasmids pSVL-αK51C, and pSVL-hcGβ'D99C. Since each hCG α-subunit based protein and each hCG β-subunit based protein has the same signal peptide leader sequence as the α- and β-subunits of hCG, they are expected to be processed in the same way. Thus, αK51C would be expected to contain 92 amino acid residues containing the N-terminal sequence APD and hCGβ'D99C would be expected to contain 145 amino acid residues containing the N-terminal sequence SKE. The single letter amino acid code used here has been defined in the legend to FIGS. 3A and 3B. The upper case letter refers to the locations of the mutations that were made to form the inter-subunit disulfide bond.

FIGS. 32A and 32B show the amino acid sequences of αC7A (FIG. 32A) (SEQ 10 NO:14), an α-subunit analog expected to be useful for preparing hCG, hLH, hFSH, and hTSH analogs stabilized by an intercysteine knot disulfide between the α- and β-subunits and hFSHβY31C (FIG. 32B) (SEQ 10 NO:15), a β-subunit analog expected to be useful for preparing hFSH analogs stabilized by an intercysteine knot disulfide between the α- and β-subunits. This figure illustrates the amino acid sequences of an α-subunit analog and an hFSH β-subunit analog in lower case letters representing the single letter amino acid code. The replacement of Cys7 by alanine in the α-subunit illustrated in upper case in the αC7A amino acid sequence would be expected to have the same effect as replacement of Cys7 by serine as illustrated in Examples 1 and 2. The presence of a cysteine residue at position 31 in the hFSHβY31C sequence is also illustrated in upper case. Cells expressing this FSH β-subunit analog and αC7A or the α-subunit analog previously identified as αC7S would be expected to secrete disulfide crosslinked heterodimeric protein having FSH activity. This signal sequence of hFSHβY31C is identical to that of hFSH β-subunit and, therefore, it is expected to be processed similarly to hFSH β-subunit. Thus, its N-terminal sequence would be NSC.

FIG. 33 shows the genetic code for preparing glycoprotein hormone analogs.

FIGS. 34A and 34B show the amino acid sequences of αV4C (FIG. 34A) (SEQ 10 NO:16), an α-subunit analog expected to be useful for preparing hCG, hLH, hFSH, and hTSH analogs stabilized by an intersubunit disulfide between the N-terminal portions of the α- and β-subunits, and hCGβR8C (FIG. 34B) (SEQ 10 NO:17), a β-subunit analog expected to be useful for preparing hCG analogs stabilized by an intersubunit disulfide between the N-terminal portions of the α- and β-subunits. This figure illustrates the coding sequence of an analog of an α-subunit analog and an hCG β-subunit analog that, when co-expressed, would be expected to form a disulfide crosslinked hormone analog having LH activity. The amino acid sequences of the proteins and their signal sequences are illustrated in single letter code. The upper case illustrates the positions of the mutations needed to form the intersubunit disulfide.

FIG. 35 shows the amino acid sequence of hFSHβ52C (SEQ 10 NO:18), an hFSH β-subunit analog expected to be useful for preparing hFSH analogs stabilized by intersubunit disulfide between the N-terminal portions of the α- and β-subunits, in which Ser2 is converted to cysteine. Cells co-expressing αQ5C (described earlier) and hFSHβS2C would be expected to produce a disulfide crosslinked heterodimer that had substantial FSH activity.

FIG. 36 shows the amino acid sequence of hLHβY37C (SEQ 10 NO:19), a β-subunit analog expected to be useful for preparing hLH analogs stabilized by an intercysteine knot disulfide between the α- and β-subunits, with the lower case letters representing the single letter amino acid code. The presence of a cysteine residue at position 37 is illustrated as an upper case letter. Cells expressing this LH β-subunit analog and the α-subunit analog previously identified as αC7S or αC7A would be expected to secrete disulfide crosslinked heterodimeric protein having LH activity. This signal sequence of hLHβY31C is identical to that of hLH β-subunit and, therefore, it is expected to be processed similarly to hLH β-subunit. Thus, its N-terminal sequence would be SRE.

FIG. 37 shows the amino acid sequence of hLHβW8C (SEQ 10 NO:20), a β-subunit analog expected to be useful for preparing hLH analogs stabilized by an intersubunit disulfide between the N-terminal portions of the α- and β-subunits, in which Trp8 is converted to cysteine. Cells co-expressing αQ5C (described earlier) and hLHβW8C would be expected to produce a disulfide crosslinked heterodimer that had substantial LH activity.

FIG. 38 shows the amino acid sequence of hTSHβY30C (SEQ 10 NO:21), a β-subunit analog expected to be useful for preparing hTSH analogs stabilized by an intercysteine knot disulfide between the α- and β-subunits, with the lower case letters representing the single letter amino acid code. The presence of a cysteine residue at position 30 is illustrated as an upper case letter. Cells expressing this TSH β-subunit analog and the α-subunit analogs previously identified as αC7s or αC7A would be expected to secrete disulfide crosslinked heterodimeric protein having TSH activity. The signal sequence of hTSHβY31C is identical to that of hTSH β-subunit, and, therefore, it is expected to be processed similarly to hTSH β-subunit. Thus, its N-terminal sequence would be FCI.

FIG. 39 shows the amino acid sequence of hTSHβF1C (SEQ 10 NO:22), a β-subunit analog expected to be useful for preparing hTSH analogs stabilized by an intersubunit disulfide between the N-terminal portions of the α- and β-subunits, in which Phe1 is converted to cysteine. Cells co-expressing αQ5C (described earlier) and hTSHβF1C would be expected to produce a disulfide heterodimer that had substantial TSH activity.

FIG. 47 is an amino acid sequence alignment showing the equivalent positions in the human gonadotropin hormone β-subunits for hCG (SEQ ID NO:2), hLH (SEQ ID NO:23), hFSH (SEQ ID NO:24), and hTSH (SEQ ID NO:25). The leader sequences are not presented in this alignment. A dot (.) indicates that there is no residue at that position.

FIG. 48 is an amino acid sequence alignment showing the equivalent positions in vertebrate α-subunit amino acid sequence from human (SEQ ID NO:1), ovine (SEQ ID NO:26), porcine (SEQ ID NO:27), bovine (SEQ ID NO:28), equine (SEQ ID NO:29), rat (SEQ ID NO:30), mouse (SEQ ID NO:31), rabbit (SEQ ID NO:32), chicken (SEQ ID NO:33), carp-1 (SEQ ID NO:34), carp-2 (SEQ ID NO:35), Eur. eel (SEQ ID NO:36), Pike eel (SEQ ID NO:37), salmon-1 (SEQ ID NO:38), and salmon-2 (SEQ ID NO:39). The leader sequences are not present in this alignment. A dot (.) indicates that there is no residue at that position.

FIG. 49 is an amino acid alignment showing the equivalent positions in vertebrate β-subunit amino acid sequence from hCG (SEQ ID NO:2), hLH (SEQ ID NO:23), eCG (SEQ ID NO:40), dLH (SEQ ID NO:41), cLH (SEQ ID NO:42), bLH (SEQ ID NO:43), oLH (SEQ ID NO:44), lLH (SEQ ID NO:45), sGTH (SEQ ID NO:46), sGTH1 (SEQ ID NO:47), sGTH2 (SEQ ID NO:48), hFSH (SEQ ID NO:24), eFSH (SEQ ID NO:49), oFSH (SEQ ID NO:50), bFSH (SEQ ID NO:51), pFSH (SEQ ID NO:52), rFSH (SEQ ID NO:53), hTSH (SEQ ID NO:25), bTSH (SEQ ID NO:54), pTSH (SEQ ID NO:55), mTSH (SEQ ID NO:56), and rTSH (SEQ ID NO:57). The abbreviations are as follows: h, human; e, equine; d, dog; c, chicken; b, bovine; o, ovine; l, rabbit; s, salmon, p, porcine; r, rat; m, mouse. A dot (.) indicates that there is no residue at that position.

DETAILED DESCRIPTION OF THE INVENTION

Figure 1A:
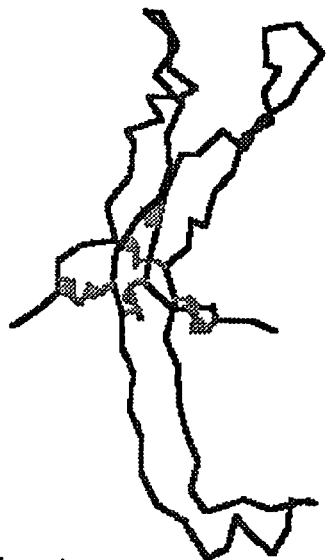
FIGS. 1A-1C show the structure of the α-subunit of hCG (FIG. 1A) along with its amino acid sequence in single letter code (FIG. 1B) (SEQ ID NO:1) and a general schematic of the structural elements in glycoprotein hormone subunits (FIG. 1C). As can be seen in FIG. 1A, the cysteine knot divides the subunit into three large loops. Loops 1 and 3 are shown at the top. Note that the black lines refer to the Cα atoms of the amino acid backbone while the grey lines refer to the disulfide bonds. The lines in FIG. 1B have been drawn to illustrate the disulfide bonds. The structural elements of glycoprotein hormone subunits as listed in Table 1A are shown in FIG. 1C in schematic form.
Figure 1B:
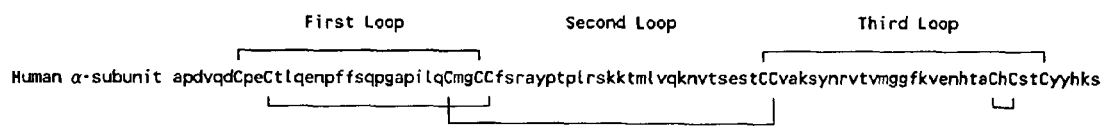
Figure 1C:
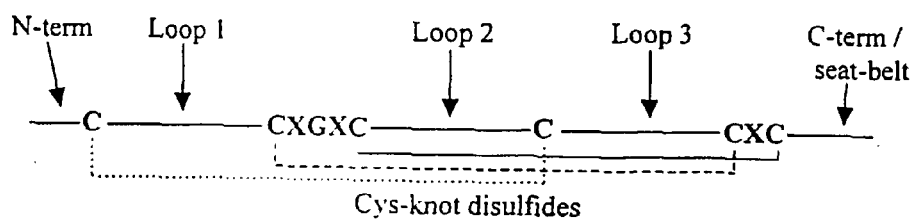
Figure 2A:
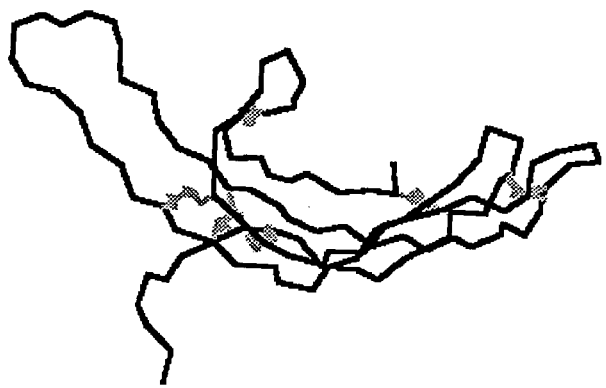
FIGS. 2A and 2B show the structure of the β-subunit of hCG (FIG. 2A) along with its amino acid sequence in single letter code (FIG. 2B) (SEQ ID NO:2). As can be seen in FIG. 2A, the cysteine knot divides the β-subunit into three large loops. Loop 2 is shown at the top. The small loop at the right side of the figure is found in the seat-belt. Positively and negatively charged residues in this region are important for LH and TSH activity, respectively. Residues shown that connect this small loop to β-subunit loop 1 seen running from the small seat-belt loop downward to the remainder of the β-subunit have a major influence on FSH and TSH receptor binding. Note that the black lines refer to the Cα atoms of the amino acid backbone while the grey lines refer to the disulfide bonds. The lines in FIG. 2B have been drawn to illustrate the disulfide bonds.
Figure 2B:
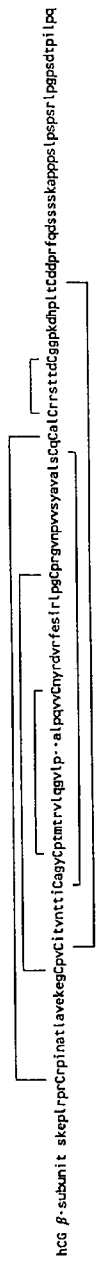

The analogs of glycoprotein hormones according to the present invention are based on the discovery that intersubunit disulfide bonds stabilize the α- and β-subunits of the glycoprotein hormone heterodimer. The analogs are designed specifically to reduce perturbation of the three-dimensional structure of the hormone, thereby creating greater likelihood that the dimer will be formed in vivo and the formed dimer will have affinity for the native receptors and have agonistic activity thereon.

The terms "analog" or "analogs" as used herein are intended to mean a glycoprotein hormone selected from human chorionic gonadotropin (hCG), human luteinized hormone (hLH), human follicle stimulating hormone (hFSH), human thyroid stimulating hormone (hTSH), and functional muteins thereof, in which the amino acid sequences of their α- and β-subunits are modified to create free cysteines in each of the subunits, which form intersubunit disulfide bonds, thereby stabilizing the heterodimer.

Also as used herein, the terms "mutein" or "muteins" are meant to refer to glycoprotein hormones hCG, hLH, hFSH, and hTSH which are modified, but not modified so as to create intersubunit disulfide bonds, and which substantially (at least 80%) retain their functional biological activity, e.g. receptor affinity and hormone potency, antibody recognition, or that increases their affinity or specificity for a different glycoprotein hormone, such as may occur with chimeric glycoprotein hormones, whether or not these muteins are expressly stated as being functional.

To generate muteins of glycoprotein hormones, the protein may be modified by any art-recognized means. For the sake of convenience, modifications are divided into those achievable by expression, in a suitable host cell of a modified gene(s) which encodes the modified protein which will be termed "mutations", and those which are not, which will be termed "derivatizations."

While normally derivatives are prepared by first synthesizing the lead molecule and then derivatizing it, derivatives may also be prepared directly. However, implicit in the term "derivatives" is that it is technically feasible to obtain the derivative by modification of the lead molecule, even if that is not the preferred method of production.

Modifications of proteins may be classified as follows:

Favorable—these modifications enhance the utility of a protein for a particular use.

Neutral—these modifications neither enhance nor diminish the utility of a protein for a particular use.

Unfavorable—these modifications diminish, but do not necessarily eliminate, the utility of a protein for a particular use.

Inactivating—these modifications eliminate the utility of a protein for a particular use.

Tolerable—these modifications are favorable, neutral, or unfavorable, but not inactivating.

It is possible, since a protein may have more than one use, that a modification is favorable for one use, unfavorable for a second, neutral for a third, and inactivating for a fourth.

In general, the effect of modifications on the suitability of the protein will be discussed for uses which are specific, to a greater or lesser degree, on the specific structure of the protein, rather than on those which are dependent only on the protein's amino acid composition, molecular weight, or gross physical properties.

A protein may be modified for a variety of reasons, including one or more of the following purposes:

to render the molecule more detectable, as in the case of radiolabeled, enzyme labeled, and fluorescent labeled derivatives;
  to render the molecule more stable with respect to a particular physical, chemical, or biological agent, such as heat, light, oxidizing agents, reducing agents, and enzymes;
  to render the molecule more soluble in a solvent of interest, e.g., to facilitate its administration, or less soluble, e.g., to facilitate its precipitation or to allow its use in capturing another molecule;
  to limit the nature of the reactions which the molecule can participate in, e.g., placing protective groups on amino acid side chains, or conversely, to expand the possible reactions, e.g., placing a reactive group on the molecule to facilitate a subsequent coupling reaction;
  to render the molecule less (or more) immunogenic;
  to increase (or decrease) the time which the molecule resides in a particular organ or tissue if administered to a subject, or to hasten (or slow) its arrival in a particular organ or tissue;
  to enhance (or diminish) one or more of its biological or immunological activities, e.g., to increase or decrease its affinity for a receptor, or to alter its specificity; or
  to confer a new activity which complements a prior activity (e.g., attaching a toxin to an antitumor antibody); or
  to inhibit a undesirable side effect of the molecule.

Most residues of a protein can tolerate some degree of mutation. Mutations may take the form of single or multiple substitutions, insertions, or deletions. Preferably, insertions or deletions are directed to the termini of the molecule, or to surface loops or interdomain boundaries.

There is no preferred maximum with respect to an insertion at a terminus, which is more aptly termed an "addition" or "fusion". It is routine to fuse one protein to another to facilitate expression, or to provide a fusion protein which has the combined biological activities of its components. A fusion protein may be useful as a precursor, which can be cleaved to liberate an active protein, even if the fusion protein itself lacks activity.

With regard to deletion at a terminus, more aptly termed "truncation", the purpose of the modification is important. It is routine to extensively truncate a protein when one is interested only in its immunological properties. One may abstract from a protein an epitope as small as five amino acids, and use it by itself to elicit a T cell response, or conjugated to copies of itself or to an immunogenic carrier to elicit a B cell response. When it is a biological activity which must be preserved, the limits on truncation may be more stringent.

Preferably, after considering substitutions, and any internal deletions and insertions, the mutant is at least 50%, more preferably at least 80%, identical in sequence to the original protein.

A protein is more likely to tolerate a mutation which
  (a) is a substitution rather than an insertion or deletion;
  (b) an insertion or deletion at the termini, than internally, or, if internally, at a loop or an interdomain linker;
  (c) affects a surface residue rather than an interior residue;
  (d) affects a part of the molecule distal to the binding site;
  (e) is a substitution of one amino acid for another of similar size, charge, and/or hydrophobicity; and
  (f) is at a site which is subject to substantial variation among a family of homologous proteins to which the protein of interest belongs.

These considerations can be used to design functional mutants.

Preferably, for the framework residues, and more preferably for the whole chain, the predicted or experimentally determined 3D structure of the modified protein has a main chain (Cα-carbon) conformation whose root-mean-square deviation from the predicted or experimentally determined 3D structure of the original protein is preferably less than 5 Å, more preferably less than 3 Å, still more preferably less than 2 Å, most preferably less than LA.

The determination of the 3-D structure of a protein can provide considerable guidance to one seeking to modify that protein for a useful purpose, or at least to avoid inactivating modifications. If the full 3-D structure is known, the practitioner knows which residues are on the surface and which are on the interior, which residues have side chains pointing toward the outside, which residues are packed closely together and which are not, where the chain is flexible and where it is constrained, which residues are in secondary structures, which residues are brought into proximity as a result of chain folding, and which may be interacting in the form of H-bonding and salt bridges.

Mutations at surface residues are more likely to be tolerated than at internal residues. Mutations at the latter positions have greater potential to destabilize the protein, thereby, by denaturing the protein, affecting all of its binding activities. Mutation at a surface residue may have no effect on binding activity at all, or it may affect some activities but not others. In any event, they are unlikely to denature the protein.

The principal methods of determining the complete 3-D structure of a protein are X-ray crystallography and NMR spectroscopy, and the principal hurdle in obtaining high-resolution X-ray diffraction data is the crystallization step. High resolution crystal structures of hCG are available from two laboratories (Lapthorn et al, 1994; Wu et al, 1994) and serves as a model for hLH, hFSH and hTSH.

In the case of smaller proteins, preferably smaller than 20 kDa, Nuclear Magnetic Resonance (NMR) spectroscopy can also elucidate the 3D-structure. For use of NMR structure determination, see McIntosh et al, (1987). NMR can also provide partial information about the structure of larger proteins. Regions of a larger protein which are of special interest may be produced separately, either by recombinant DNA techniques or by controlled proteolysis, and then studied by NMR.

Various spectral changes accompany the alteration of the charge of environment of certain amino acids. If the amino acids tryptophan, tyrosine, phenylalanine and histidine are shifted to a less polar environment, $\lambda$max and $\epsilon$ increase. Thus, if they are higher for one of these amino acids in a polar solvent, then for the free amino acid the same solvent, the residue must be buried and surrounded by non-polar amino acids. Also, if the spectrum of a protein is sensitive to changes in solvent polarity, the amino acid in question must be on the surface. To give another example, for amino acids, $\lambda$max and $\epsilon$ always increase if a titratable group (e.g., the OH of tyrosine, the imidazole of histidine, and SH of cysteine) is charged. Hence, by correlating special changes with pH changes, one may deduce whether the titratable group is on the surface or buried. Residues in deep crevices may be distinguished from those completely on the surface, or completely buried, by comparison of results with solvents whose molecules have different mean diameters.

Besides being of use in determining the location of particular residues, these spectroscopic techniques can help resolve ambiguities in X-ray and NMR analysis.

Amino acid-specific chemical affinity labels may be used to ferret out which residues are in fact exposed. The most useful labels are likely to be those which react with charged residues, as those are most likely to appear on the surface. Sample labels include the following:

| Amino Acid | Affinity Label |
| --- | --- |
| Asp, Glu | diazo compounds (with non-ionized AA) or epoxides (with ionized AA) |
| Lys | 2,4,6-trinitrobenzene sulfonic acid; acetic, succinic, maleic and citraconic anhydrides |
| Arg | cyclohexanedione, hydrazine |

Labeled and unlabeled protein are then separately subjected to a fragmentation reagent such as cyanogen bromide, pepsin, papain, chymotrypsin, trypsin or iodosobenzoic acid. The peptides resulting from cleavage of the labeled protein are compared to those derived from the native protein, using two-dimensional electrophoresis. Peptides that have altered mobility are sequenced, and modified amino acids are determined.

Adachi et al (1989) used Arg- and Lys-specific reagents to explore the role of these residues in both the catalytic and heparin-binding activities of EC-SOD. They found that modification of these residues did result in diminution of these activities; however, they did not attempt to discern which residues had been modified.

Surface residues may also be identified by means of photoaffinity labels which, upon exposure to light, form highly reactive intermediates, e.g. nitrenes and carbenes. These species are capable of insertion into C—H bonds, and therefore can react with any accessible amino acid. For this reason, photoaffinity labeling has been used to study membrane topography. Some proteins lie at the periphery of the membrane, others are integral to it.

Another example of a nonspecific labeling reagent is tritium. A folded protein may be tritiated (by hydrogen exchange with tritiated water), denatured, and fragmented, and the fragments sequenced and tested for the presence of tritium (which is radioactive).

All of these labeling methods may also be used to determine whether residues, besides being on the surface, are part of a binding site. The distribution of label obtained when free protein is labeled is compared with that obtained when the complexed protein is labeled. Since in the complex, the binding partner occludes the binding site residues of the binding protein, binding site residues should be labeled in the free protein and not in the complexed protein.

In general, within families of proteins of similar sequence and function, surface residues are more likely to vary than are interior residues. This is most likely because the surface residues are unlikely to be involved in interactions with other residues which are necessary to maintain the overall conformation of the protein.

The most reliable method of identifying the surface residues of a protein is to determine the protein's 3-D structure by X-ray diffraction. Even an incomplete 3D structure can be useful in designing mutants. Residues with high mobility, as evidenced by a higher than average crystallographic thermal factor, are those least susceptible to destabilizing mutations. See Alber et al (1987).

Although many amino acid substitutions can be made at surface positions with no adverse effects, substitutions at internal positions tend to be severely destabilizing. Within families of homologous proteins, the most conserved residues, apart from functional amino acids, are those which are buried.

The main contribution to the free energy of protein folding, and hence to protein stability, comes from burying hydrophobic side chains in the interior, thereby shielding them from solvent. Packing densities are typically high. In general, the ability of a protein to tolerate mutations which alter the volume of core residues is dependent more on the net change in the total core residue volume, then on the magnitude of the individual residue volume changes. In other words, an increase in the volume of one core position can compensate for a decrease in the volume of another core position. Preferably, the net change in the total core residue volume is not more than 10%, more preferably, not more than 5%. See Lim et al (1989); Lim et al (1992).

In the absence of evidence to the contrary, all residues identified as interior residues may be assumed to be part of a single core. However, if it is likely that the protein folds to form several distinct cores, the above-stated volume conservation rule should be applied separately to each core.

The makeup of the buried core of a protein is dependent, not only on the propensity of each amino acid, if present, to be buried, but also on the overall frequency of occurrence of that amino acid in the protein. The most commonly buried residues are, in descending order, Val, Gly, Leu, Ala, Ile and Ser.

Lim et al (1992) reported that replacing a single hydrophobic amino acid (Leu, Val) in the protein core with a hydrophilic amino acid (Asn, Gln) prevented the complete folding of the protein and destroyed biological activity.

Buried Cys, (-S-S-form), Asp, Gly, His, Pro, and Trp are more than 70% likely to be unchanged in a homologous protein. Therefore, if these residues occur in a buried position in the protein of interest it is preferable to leave them unchanged. Their conservation is probably explainable as follows: Cys (disulfide bonding), Asp (charged but rigid side chain), Gly (chain flexibility), His (charged and uncharged states both available at physiological pH), Pro (unique chain geometry), and Trp (largest side chain).

The other residues, with the exception of Met, are 40-60% likely to be left unchanged when buried (Met is unchanged only 26% of the time, but it is 25% likely to be replaced by Leu).

The following buried residue substitution probabilities exceed 10%:

Ala→Val, Glu→Gln, Phe→Leu, Ile→Leu, Ile→Val,
Lys→Arg, Leu→Ile, Leu→Val, Met→Leu, Met→Val,
Asn→Asp, Asn→Ser, Arg→Lys, Arg→Gln, Ser→Ala,
Thr→Ser, Val→Ile, Val→Leu, Tyr→Phe,
Cys(-SH)→Ala.

These further substitutions have probabilities in the 5-10% range:

Ala→Ser, Asp→Asn, Glu→Arg, Glu→Val, Phe→Ile,
Phe→Val, Phe→Tyr, His→Val, Leu→Phe, Met→Ala,
Met→Ile, Gln→Glu, Gln→His, Gln→Met, Ser→Gly,
Ser→Thr, Thr→Val, Val→Ala, Trp→Phe, Tyr→Leu,
Cys(-SH)→Ser.

See Overington et al (1992), Table 5.

The most consistent exchange groups appear to be (Arg, Lys), (Leu, Ile, Met, Val, Phe), and (Ser, Thr, Ala). However, Ala and Val appear to be fairly promiscuous.

In general, therefore, it is preferable to avoid mutating buried residues at all. However, if they are mutated, one should limit the overall change in the volume of the core, and most preferably should limit the mutation to the replacement of one residue with another whose typical substitution probability exceeds zero, more preferably is at least 5%, and most preferably at least 10%. Mutation of buried Cys(-S-S), Asp, Gly, His, Pro and Trp should be avoided, absent justification by other evidence. The safest core mutations are exchanges of one hydrophobic amino acid for another, and of Arg for Lys (or vice versa).

Nonetheless, judicious mutation at internal residues may be used to improve protein stability. Such mutations could introduce additional stabilizing interactions (hydrogen bonds, ion pairs) compatible with the native structure, or could reduce the mobility of nearby interacting groups by replacing smaller amino acids with larger ones, or linear side chains with branched or aromatic ones. See Alber et al (1987).

More importantly, in addition to the generalizations on modifications to residues in the glycoprotein hormones discussed above, there is a considerable amount of available information on regions of the glycoprotein hormones (hCG in particular) that may or may not be exposed upon binding to a glycoprotein hormone receptor and that do not disrupt hormone-receptor interactions, i.e., receptor affinity and hormone potency. Such available information on residues and regions which can be safely modified is presented in the Description of the Related Art section, as well as elsewhere in the present specification. Accordingly, from the wealth of structure and function data as presented herein and as available in the scientific literature, it is well within the skill of those in the art to make modifications to the amino acid sequences of the glycoprotein hormones that do not disrupt their function.

Furthermore, the functional muteins of the glycoprotein hormones are intended to encompass chimeric glycoprotein hormones in which one or more residues or regions of a glycoprotein hormone, i.e., the β-subunit seat belt, are replaced by a corresponding residue(s) or region(s) from another glycoprotein hormone which may, for example, change the receptor binding specificity. Some examples of residues and regions affecting receptor binding specificity, etc., are discussed in the present specification.

The muteins of the glycoprotein hormones are further intended to encompass single chain glycoprotein hormones in which the α- and β-subunits are translated as a single chain and correctly folded into its heterodimer conformation.

A procedure is outlined below that can be used to identify residues that have the potential to form disulfide bonds. As will be demonstrated in the following examples, not all disulfide bond stabilized heterodimers of hCG and its analogs retain their full biological potency. However, the introduction of an intersubunit disulfide between the cysteine knots has the ability to increase protein stability without disrupting hormone potency.

Disulfide bond crosslinked glycoprotein hormone analogs according to the present invention can be prepared by creating free cysteines in each of the subunits which can be crosslinked to form one or more intersubunit disulfide bonds. This can be accomplished by replacing the codons for one or more amino acids with those for cysteine or by replacing the codon for a cysteine residue in an existing disulfide bond with a codon for any other amino acid. However, not all such substitutions would be expected to create intersubunit disulfide bonds. Two of the factors that should be considered in the design of the analogs are illustrated here.

1) The most useful disulfide crosslinked glycoprotein hormone analogs are expected to have a structure similar to that of hCG, hLH, hFSH, or hTSH. Thus, the disulfide should not grossly distort the overall conformation of the protein. The locations of disulfides that are expected to have the least disruptive influence on protein conformation can be predicted from the data in Table 1B that illustrate the approximate distances between the Cα and Cβ carbon atoms of selected amino acid residues in the α-subunit of hCG (left column of each pair of columns) and one or more nearby residues of the hCG β-subunit (right column of each pair of columns). These values can be calculated from the crystal structure of hCG by any of several well-known, widely and publicly available molecular modeling packages including Sybyl, Insight, Rasmol, and Kinemage, to name a few. The distance between amino acid residues in the α-subunit of the hCG and one or more nearby residues of the hCG β-subunit besides those shown in Table 1B can be readily calculated from the published crystal structure data of hCG (Lapthorn et al, 1994; Wu et al, 1994)

TABLE 1B

Approximate Distances Between Cα and Cβ Carbon Atoms of Selected hCG α- and β-Subunit Residues

| α-Subunit Residue | β-Subunit Residue * | |
|---|---|---|
| Val4 | Pro4 | (7.2, 5.7) |
| | Pro7 | (7.3, 7.2) |
| | Arg8 | (7.6, 8.4) |
| Gln5 | Pro4 | (6.3, 6.5) |
| | Pro7 | (5.6, 7.1) |
| | Arg8 | (5.2, 3.9) |
| Asp6 | Pro4 | (4.7, 4.1) |
| | Leu5 | (6.2, 6.0) |
| | Arg6 | (5.3, 6.0) |
| | Pro7 | (4.7, 6.8) |
| | Arg8 | (5.4, 6.8) |
| Cys7 | Pro4 | (7.7, 7.4) |
| | Leu5 | (7.3, 7.8) |
| | Arg6 | (4.9, 3.9) |
| | Pro7 | (5.9, 6.7) |
| | Arg8 | (5.6, 5.0) |
| | Tyr37 | (6.3, 3.5) |
| | Cys38 | (7.1, 7.4) |
| | Pro39 | (7.1, 6.6) |
| Pro8 | Arg6 | (7.3, 7.5) |
| | Pro39 | (7.2, 6.4) |
| Glu9 | Arg6 | (7.4, 6.3) |
| Gln27 | Met41 | (7.9, 6.6) |
| | Thr42 | (7.6, 7.7) |
| | Arg43 | (7.9, 8.6) |
| | Val44 | (6.7, 5.5) |
| Cys28 | Met41 | (6.3, 7.0) |
| | Thr42 | (6.9, 6.3) |
| Met29 | Pro39 | (7.6, 7.9) |
| | Thr40 | (6.4, 8.2) |
| | Met41 | (5.0, 4.8) |
| | Thr42 | (7.5, 9.0) |
| Gly30 | Cys38 | (7.8, 7.8) |
| | Pro39 | (5.1, 5.1) |
| | Thr40 | (5.6, 5.6) |
| | Met41 | (6.7, 6.7) |
| Cys31 | Arg6 | (7.6, 5.1) |
| | Tyr37 | (5.7, 3.6) |
| | Cys38 | (5.0, 5.8) |
| | Pro39 | (4.2, 5.4) |
| | Thr40 | (5.7, 7.2) |
| Cys32 | Gly36 | (7.9, 7.9) |
| | Tyr37 | (5.2, 6.3) |
| | Cys38 | (5.5, 6.5) |
| | Pro39 | (6.7, 8.8) |
| | Thr40 | (7.1, 6.2) |
| Phe33 | Arg6 | (7.7, 7.4) |
| | Ala35 | (7.7, 7.8) |
| | Gly36 | (5.1, 5.1) |
| | Tyr37 | (4.5, 6.0) |
| | Cys38 | (6.6, 8.5) |
| Ser34 | Cys9 | (7.6, 6.9) |
| | Ala35 | (6.0, 7.6) |
| | Gly36 | (5.3, 5.3) |
| | Tyr37 | (5.8, 7.1) |
| | Cys38 | (6.9, 5.4) |
| | Val56 | (6.0, 4.7) |
| | Cys57 | (5.2, 3.9) |
| Arg35 | Cys9 | (8.0, 8.2) |
| | Ile33 | (7.9, 6.5) |
| | Cys34 | (5.6, 6.4) |
| | Ala35 | (4.4, 3.5) |
| | Gly36 | (6.2, 6.2) |
| | Val56 | (7.2, 8.2) |
| | Cys57 | (5.3, 5.4) |
| | Asn58 | (6.8, 9,1) |
| Ala36 | Ile33 | (6.4, 6.8) |
| | Cys34 | (5.0, 4.7) |
| | Ala35 | (6.3, 7.5) |
| | Cys57 | (6.4, 6.0) |
| | Asn58 | (5.5, 5.0) |
| | Tyr59 | (6.7, 5.8) |
| Tyr37 | Ile33 | (5.6, 4.3) |
| | Cys34 | (6.6, 7.6) |
| Pro38 | Ala83 | (6.8, 4.9) |
| Thr39 | Asp99 | (7.8, 6.0) |
| Pro40 | Ala17 | (7.9, 7.0) |
| | Pro107 | (8.0, 5.9) |
| | Leu108 | (7.7, 7.7) |
| Leu41 | Glu19 | (7.7, 6.2) |
| Gln50 | Thr97 | (7.8, 9.2) |
| Lys51 | Ser96 | (7.6, 8.8) |
| | Thr97 | (5.2, 6.4) |
| | Thr98 | (5.4, 6.2) |
| | Asp99 | (5.8, 4.2) |
| Asn52 | Thr97 | (6.4, 6.3) |
| | Thr98 | (6.4, 8.3) |
| | Asp99 | (7.7, 9.0) |
| Val53 | Thr97 | (6.9, 6.4) |
| | Thr98 | (4.9, 4.8) |
| | Asp99 | (5.9, 6.9) |
| Thr54 | Thr98 | (5.8, 7.5) |
| | Asp99 | (4.5, 4.5) |
| | Cys100 | (6.7, 8.9) |
| | Gly101 | (7.6, 7.6) |
| Ser55 | Val56 | (7.6, 5.0) |
| | Asn58 | (7.7, 6.7) |
| | Cys93 | (7.2, 4.6) |
| | Thr98 | (6.6, 5.0) |
| | Asp99 | (5.5, 6.3) |
| | Cys100 | (5.1, 5.2) |
| | Gly101 | (5.7, 5.7) |
| | Gly102 | (7.3, 7.3) |
| Glu56 | Cys100 | (7.2, 9.7) |
| | Gly101 | (5.6, 5.6) |
| | Gly102 | (4.8, 4.8) |
| | Pro103 | (4.8, 5.2) |
| | Lys104 | (7.0, 6.5) |
| Ser57 | Val56 | (6.3, 4.2) |
| | Cys57 | (7.9, 6.9) |
| | Cys100 | (7.9, 7.9) |
| | Gly101 | (6.4, 6.4) |
| | Gly102 | (5.0, 5.0) |
| | Pro103 | (6.1, 7.8) |
| Thr58 | Gly102 | (6.8, 6.8) |
| | Pro103 | (7.4, 6.6) |
| Cys59 | Thr40 | (6.3, 4.5) |
| | Met41 | (7.7, 8.6) |
| | Gln54 | (7.8, 4.9) |
| Cys60 | Pro39 | (7.8, 7.9) |
| | Thr40 | (5.6, 4.7) |
| | Met41 | (5.9, 6.1) |
| | Thr42 | (7.9, 7.9) |
| Val61 | Met41 | (6.7, 8.8) |
| | Thr42 | (6.6, 5.8) |
| Phe74 | Leu45 | (7.1, 6.5) |
| | Gln46 | (7.8, 8.4) |
| Lys75 | Leu45 | (6.1, 7.7) |
| | Gln46 | (5.4, 4.6) |
| | Gly47 | (7.4, 7.4) |
| Val176 | Val44 | (5.3, 4.5) |
| | Leu45 | (4.4, 5.5) |
| | Gln46 | (5.4, 6.5) |
| Glu77 | Val44 | (4.8, 5.7) |
| | Leu45 | (6.2, 8.2) |
| | Gln46 | (6.7, 6.0) |

TABLE 1B-continued

Approximate Distances Between
Cα and Cβ Carbon Atoms of
Selected hCG α- and β-Subunit Residues

| α-Subunit Residue | β-Subunit Residue * | |
|---|---|---|
| His79 | Val44 | (7.9, 7.1) |
| Thr86 | Gly102 | (6.5, 6.5) |
| Cys87 | Gln54 | (6.9, 5.0) |
|  | Gly101 | (7.7, 7.7) |
|  | Gly102 | (7.2, 7.2) |
| Tyr88 | Gly101 | (7.2, 7.2) |

* [Distance between Cα carbons (A), Distance between Cβ carbons (A)]

The left value of each pair of values presented in the parentheses associated with each β-subunit residue shows the distance between the Cα carbon atom of that β-subunit residue and the corresponding α-subunit residue in the left column. The right value of each pair of values presented in the parentheses shows the corresponding distance between the Cβ carbon atoms of these residues. In principle, replacing these pairs of residues with cysteines would permit the formation of an intersubunit disulfide bond, provided that no other interfering cysteine were present in either subunit. Not all pairs of cysteines would have an equal probability of forming an intersubunit disulfide. Formation of an intersubunit disulfide expected to have the least influence on the conformation of the heterodimer would be influenced by the orientation of the sidechain atoms of their component cysteines. Favorable and preferred positions for placement of disulfides would include amino acid pairs in which the distance between the Cβ carbon atoms is smaller than that between their Cα carbons. The most favorable and preferred locations for the placement of an intersubunit disulfide bond are those in which the distances between the Cα and Cβ carbons are similar to those in naturally occurring disulfides, namely about 5.0-6.5 Å and about 3.5-4.2 Å, respectively.

Thus, substitutions that created an intersubunit pair of cysteines having Cα carbon atoms 4-8 Å apart and Cβ carbon atoms 1-2 Å closer would be expected to have the best chance of forming a disulfide with the least influence on overall protein structure and/or promoting intermolecular crosslinking of two or more molecules. Indeed, as shown in the examples, this rule of thumb according to the present invention has been used successfully to create several disulfide crosslinked hCG analogs that retain many of their immunological and hormonal properties.

2) The most active disulfide crosslinked glycoprotein hormone analogs would be expected to contain the crosslink at sites not needed for receptor binding or signal transduction and/or at sites not needed for stabilizing the active conformation of the hormone. There are a large number of residues in the glycoprotein hormones that are known not to be needed for their biological activities. These include most residues N-terminal of the cysteine knot (i.e., the second cysteine in the native α-subunit and the first cysteine in the native β-subunits). For example, highly potent analogs of hFSH have been prepared in which these FSH β-subunit residues (Asn1, Ser2) were replaced with their hCG counterparts (Ser1, Lys2, Glu3, Pro4, Leu5, Arg6, Pro7, Arg8). Thus, a disulfide in this region of the molecule made by replacing hCG α-subunit Gln5 and β-subunit Arg8 with cysteines would not be expected to eliminate the LH activity of the disulfide crosslinked heterodimer. Similarly, a disulfide made by replacing hFSH α-subunit Gln5 and β-subunit Ser2 with cysteines would not be expected to eliminate the FSH activity of the disulfide crosslinked heterodimer. By changing α-subunit Cys31 to Ala or Ser and by replacing hCG β-subunit Arg6 with Cys or adding a Cys to the N-terminus of the FSH β-subunit, it is expected that a disulfide could be created in the N-terminal region of the α- and β-subunits of hCG or hFSH. This disulfide would not be expected to disrupt the activity of either hormone analog.

The crystal structure of hCG revealed that each of its subunits is composed of a cysteine knot. Thus, each subunit contains three loops termed α1,α2,α3 and β1,β2,β3. In addition, the β-subunit has 20 additional amino acids known as the seat-belt that surround α2 to secure the heterodimer and stabilize it in a conformation capable of binding to its unique receptor. The locations of the cysteines in lutropins, follitropins, and thyrotropins suggest that all three molecules will have a similar overall folding pattern and that the crystal structure of hCG will be a reasonable guide to introducing intersubunit disulfides. However, the structures of FSH and TSH have not been determined and can only be inferred from that of hCG. The crystal structures of the cysteine knots of each subunit show each to be highly similar. This is because they are highly constrained by their three component disulfide bonds. Thus, residues within and adjacent to the cysteine knots are expected to have similar conformations in each hormone. Further, there is a cysteine in loops β1 and β3 at similar positions in all three classes of hormones. These form a disulfide in hCG and would be expected to form a disulfide in all glycoprotein hormones. This disulfide and the extensive number of hydrogen bonds within and between the backbone atoms in these loops of hCG suggests that the conformations of β1 and β3 will be highly similar in all three hormone classes. Loops a1 and α3 also contain several hydrogen bonds, suggesting that this portion of the molecule will also be similar in all three hormone classes. This view is supported by the observation that an NMR structure of the free α-subunit shows that a1 and α3 have similar conformations even when not in the heterodimer (DeBeer, et al, 1996). While the remaining portions of all three classes of hormones are almost certainly similar in conformation to that of hCG, they are not likely to be as closely related to the structure of hCG as the portions of the molecules just discussed. For example, β2 contains relatively few internal hydrogen bonds and/or contacts with α1 and α3. Because it does not appear to be highly constrained in hCG, there is no reason to believe that its structure will be completely identical to that in the other hormones. Indeed, loop β2 in TSH is 2 amino acid residues larger than that in hCG or hFSH. The N- and C-terminal ends of α2 participate in extensive hydrogen bond contacts and portions of the C-terminal end of α2 also contact β1. Thus, these parts of α2 might be similar in most hormones. However, the central portion of α2 contacts only the seat-belt, a region of the protein that is not well conserved in the three hormone classes. The NMR structure of the α-subunit showed α2 to be highly disordered, an observation suggesting that this part of the hormone in hCG has a well-ordered structure in the heterodimer only because it is sandwiched between β1, β3, and the seat-belt. Differences in the seat-belt would be expected to alter the conformation of α2, particularly those portions not located near the cysteine knot.

Insights into the influence of the seat-belt on hormone structure have been obtained by the present inventor using immunological probes to study hCG analogs that have the ability to bind to lutropin and follitropin receptors. These data suggest that the composition of the seat-belt can alter the conformation of the hormone. Similar data also suggest that the conformation of the hormone can be influenced by the receptor. For example, monoclonal antibodies whose binding sites have been partially determined (Moyle, et al, 1990; Moyle, et al, 1995) have been used to study the conformation of a bifunctional hCG analog (CF101-109) when it is free and when it is bound to LH and FSH receptors. CF101-109 was prepared by replacing hCG seat-belt residues 101-109 with hFSH seat-belt residues 95-103 (Moyle, et al, 1994). The abilities of CF101-109 to be recognized by monoclonal antibodies showed that the presence of the FSH residues in the seat-belt altered the interaction between the two subunits. Thus, A407, an antibody to a conformational epitope that included residues at the N-terminal end of the α-subunit in hCG but not hFSH, had greatly reduced affinity for CF101-109 even though its epitope is distant from the site of the mutation (Table 1C). The influence of the receptor on hormone structure was seen by the fact that A407 recognized CF101-109 when it was bound to LH receptors but not when it was bound to FSH receptors (Table 1D). Other antibodies that recognize epitopes located entirely within α1 and/or α2 or within β1 and/or β3 recognized CF101-109 even when it was combined with receptors.

Taken together, these observations suggest that the positions of the subunits within the hormones may not be identical and can be influenced by interactions with their receptors. Therefore, the present inventor has determined that, in addition to considering the relative locations and orientations of potential cysteine substitutions obtained from the crystal structure of hCG, one should also consider the likelihood that the crystal structure of hCG will represent the structures of follitropins and thyrotropins and/or the conformation of the hormone in the hormone-receptor complex. The portions of the hormones that are most likely to be identical to those of hCG and least likely to be altered during receptor interaction include those in or near residues in the cysteine knot.

TABLE 1C

Recognition of hCG, hFSH and hCG/hFSH Chimeras by Anti-hCG α-subunit Monoclonal Antibodies

| | | Radiolabeled Test Anti-α-subunit Antibody | | | | | | |
|---|---|---|---|---|---|---|---|---|
| Analog | :Capture | $^{125}$I-A105 | $^{125}$I-A109 | $^{125}$I-A110 | $^{125}$I-A112 | $^{125}$I-A113 | $^{125}$I-A202 | $^{125}$I-A407 |
| hCG | :B112 | 100 ± 4.0 | 100 ± 2.4 | 100 ± 4.7 | 100 ± 4.7 | 100 ± 4.9 | 100 ± 4.9 | 100 ± 1.7 |
| | :B410 | 100 ± 5.7 | 100 ± 2.5 | 100 ± 2.4 | 200 ± 3.6 | 100 ± 1.3 | 100 ± 1.3 | 100 ± 4.2 |
| CF94-97 | :B112 | 90.5 ± 4.0 | 136.8 ± 4.0 | 105.0 ± 6.6 | 116.7 ± 1.9 | 101.2 ± 3.2 | 113.3 ± 2.7 | 103.4 ± 4.9 |
| | :B410 | 145.3 ± 6.0 | 145.0 ± 6.0 | 125.9 ± 2.5 | 104.4 ± 3.6 | 120.4 ± 1.8 | 136.6 ± 9.0 | 128.2 ± 12.5 |
| CF101-109 | :B112 | 102.1 ± 0.6 | 49.6 ± 2.3 | 82.8 ± 3.8 | 86.3 ± 2.1 | 84.2 ± 1.5 | 66.7 ± 0.8 | 6.8 ± 0.9 |
| | :B410 | 87.8 ± 4.4 | 80.0 ± 3.8 | 87.9 ± 1.7 | 82.7 ± 1.4 | 119.8 ± 0.3 | 100.5 ± 4.0 | 16.7 ± 0.1 |
| CF94-117 | :B112 | 149.8 ± 5.6 | 184.5 ± 9.4 | 140.8 ± 4.1 | 144.7 ± 2.6 | 109.4 ± 2.3 | 137.3 ± 4.7 | 31.0 ± 1.0 |
| | :B410 | 118.0 ± 8.7 | 158.3 ± 3.7 | 141.9 ± 1.2 | 1118. ± 1.3 | 124.1 ± 2.7 | 139.7 ± 3.8 | 18.0 ± 0.8 |
| CF39-58 | :B112 | 38.1 ± 2.3 | 1.2 ± 0.1 | 78.8 ± 2.0 | 68.8 ± 3.5 | 73.1 ± 0.7 | 79.6 ± 1.4 | 96.4 ± 0.6 |
| | :B410 | 11.4 ± 2.7 | 2.9 ± 0.3 | 69.8 ± 0.1 | 67.5 ± 1.1 | 96.9 ± 0.4 | 106.3 ± 1.3 | 129.1 ± 1.3 |
| hFSH* | :B602 | −2.5 ± 5.8 | 2.8 ± 0.6 | 49.0 ± 6.1 | 56.0 ± 0.9 | 77.7 ± 2.6 | 65.2 ± 1.1 | −6.7 ± 1.4 |

TABLE 1D

Binding of Radiolabeled Antibodies to hCG or CF101-109 Complexed to the Rat LHR or Human FSHR

| | | Anti-α-subunit Antibody | | Anti-β-Subunit Antibody | | |
|---|---|---|---|---|---|---|
| Analog | Experiment | A105 | A407 | B105 | B112 | B410 |
| | | Rat LHR | | | | |
| hCG | 1 | 3853 ± 1709 | 6215 ± 968 | 14706 ± 2042 | Not Tested | Not Tested |
| | 2 | 7749 ± 1484 | 38294 ± 3653 | 21582 ± 1272 | Not Tested | Not Tested |
| | 3 | 5486 ± 757 | 37855 ± 2051 | 22415 ± 3071 | Not Tested | 12718 ± 2044 |
| | 4 | 4197 ± 550 | 29915 ± 1018 | 21037 ± 957 | 11937 ± 154 | Not Tested |
| | Ratio to B105: | 0.27 ± 0.05 | 1.33 ± 0.45 | 1.0 | 0.57 | 0.57 |
| CF101-109 | 1 | 4846 ± 1737 | 1900 ± 315 | 17944 ± 2804 | Not Tested | Not Tested |
| | 2 | 10770 ± 1673 | 4130 ± 627 | 29110 ± 2445 | Not Tested | Not Tested |
| | 3 | 11781 ± 1754 | 2854 ± 695 | 13074 ± 1985 | Not Tested | 6282 ± 1437 |
| | 4 | 8537 ± 171 | 7960 ± 466 | 27647 ± 387 | 14101 ± 1152 | Not Tested |
| | Ratio to B105: | 0.46 ± 0.22 | 0.19 ± 0.07 | 1.0 | 0.51 | 0.48 |
| | | Human FSHR | | | | |
| CF94-117 | 1 | Not Tested | Not Tested | Not Tested | Not Tested | Not Tested |
| | 2 | 2910 ± 603 | <0 ± 300 | 14641 ± 1064 | Not Tested | Not Tested |
| | 3 | 1665 ± 269 | 61 ± 347 | 7313 ± 2569 | Not Tested | 3039 ± 1242 |
| | 4 | 5321 ± 308 | 50 ± 413 | 28204 ± 1481 | 2320 ± 574 | Not Tested |
| | Ratio to B105: | 0.2 ± 0.02 | 0 | 0.082 | 0.082 | 0.42 |
| CF101-109 | 1 | Not Tested | Not Tested | Not Tested | Not Tested | Not Tested |
| | 2 | 8958 ± 601 | <0 ± 271 | 24781 ± 1369 | Not Tested | Not Tested |
| | 3 | 5611 ± 611 | 129 ± 286 | 10214 ± 5750 | 4693 ± 1056 | 4693 ± 1056 |
| | 4 | 7358 ± 439 | 444 ± 323 | 20923 ± 751 | Not Tested | Not Tested |
| | Ratio to B105: | 0.42 ± 0.09 | 0 | 0.33 | 0.46 | 0.46 |

Notes:
Ligand Receptor complexes were formed and then detected using radiolabeled monoclonal antibodies as described in the text. Values illustrated (average of triplicates ± SEM) are cpm minus the blank. In most cases, data for binding to LHR and FSHR were obtained in the same experiment (identified by number in the left column). "Ratio to B105" was calculated by dividing the amount of radiolabel seen with each antibody divided by that obtained with B105 and taking the average of these values. All values except those for binding of A407 to CF94-117 and CF101-109 bound to FSHR are greater than 0 ($p < 0.05$).

The region between the cysteine knots is one of the most attractive sites for engineering a disulfide bond and is a preferred site for an intersubunit disulfide bond. The cysteine knot of each subunit is stabilized by three disulfides, making it one of the most rigid parts of the molecule. The results from the laboratory of the present inventor indicate that changing hCG β-subunit residue Tyr37 had relatively little influence on hormone activity. Thus, the presence of a cysteine at this site is not expected by the present inventor to alter hormone activity. As shown in the present examples, one way this can be accomplished is by replacing α-subunit residue Cys7 with Ala or Ser to disrupt the Cys7-Cys31 intrasubunit disulfide and replacing hCG β-subunit Tyr37 with Cys. The crosslinked analog of hCG that was produced had high LH activity. Similarly, in another non-limiting example, it was possible to prepare a crosslinked analog of CFC101-114, an hCG/hFSH chimera in which hCG β-subunit amino acid residues 101-114 were replaced with their hFSH counterparts (i.e., β-subunit residues 95-108). CFC101-114 binds and activates both LH and FSH receptors. The disulfide crosslinked analog was also capable of binding and activating both LH and FSH receptors. The latter observation shows that this disulfide does not prevent FSH receptor activity, making it highly likely that a similar disulfide in hFSH would also not destroy its hormonal activity. Preparation of a disulfide crosslinked hFSH could be accomplished by co-expressing the α-subunit cDNA in which Cys7 is converted to Ala and the hFSH β-subunit cDNA in which Tyr31 is converted to Cys. A disulfide bond between the cysteine knots can also occur with another intersubunit disulfide bond elsewhere, such as between a loop 2 and β seat-belt or between α-N-terminus and β-N-terminus, as a preferred embodiment. Furthermore, disulfide bonds formed between the Cys knots of α- and β-subunits would free-up a residue near the N-terminus, i.e., αCys7Ser, that can advantageously be used for PEGylation.

An intersubunit disulfide bond located between the cysteine knots of the α- and β-subunits may also fit into the general rule of minimizing the potential impact of intersubunit crosslinks on hormone structure by placing both crosslink positions within two residues of existing (native) cysteines involved in native disulfide bonds and not outside, i.e., further N-terminal or C-terminal, of the most N-terminal or C-terminal cysteine (the outermost cysteine unit of the corresponding native subunit) as a means to minimize the risk of structural perturbations.

Hormone analogs crosslinked by a disulfide between α-subunit loops 1 or 3 and β-subunit loop 2 would also be expected to retain hormone activity. These regions are highly amenable to amino acid substitutions. Thus, replacing the human α-subunit in hCG or hFSH with the bovine α-subunit usually does not eliminate hormone activity even though the bovine and human α-subunits differ significantly in this region. Likewise, wholesale substitutions of hFSH residues for hCG residues and vice versa in β-subunit loop 2 did not eliminate the activity of either hormone. Thus, disulfides in this region would not be expected to disrupt biological activity of either lutropins or follitropins. These disulfides include those created by changing α-subunit Gln27 and hCG or hLH β-subunit Val44 or hFSH β-subunit Val38 to Cys. They also include disulfides prepared by changing α-subunit Val76 and hCG β-subunit Val44 or hFSH β-subunit Val38 to Cys. Another intersubunit disulfide crosslinked analog expected to retain substantial activity is one having α-subunit residue Lys75 and hCG or hLH β-subunit residue Gln46 or hFSH β-subunit residue Lys40 converted to Cys. However, the latter analog would be less positively charged than either hCG or hFSH and thus its overall LH or FSH activity might be low. It is further possible to insert intersubunit disulfides into other regions of lutropins and follitropins. Some of these disulfides involve residues in the β-subunit seat-belt (i.e., created by substitution of hCG β-subunit Asp99 by Cys) and α-subunit loop 2 (i.e., created by substitution of α-subunit Lys51 with Cys). This disulfide significantly reduced the LH activity of hCG and the LH and FSH activities of the bifunctional analog CFC101-114. The location of residues in hLH, hFSH, and hTSH that can be mutated to cysteine with the expectation of producing a disulfide bond can be determined from the "equivalent" locations of the α- and β-subunit residues in these proteins as defined in FIGS. 47-49.

The information in FIG. 47 can be used to calculate residues that occupy "equivalent" positions in each human hormone β-subunit. Crystal structures are only available for hCG. However, due to the high similarities in the amino acid sequences of all the glycoprotein hormones, notably their intrasubunit disulfides, it is expected that all the hormones will have similar shapes. The conclusion that the overall conformation of all the heterodimers is similar to that of hCG is also supported by the observation that it is possible to prepare hCG/hFSH, hCG/hLH, and hCG/hTSH chimeras that retain epitopes found in regions of their progenitors used to derive the chimeras. Thus, it is expected that substitution of equivalent residues as defined in this table will lead to intersubunit disulfide bonds that have similar properties to those that have been made and characterized. "Equivalent" positions are defined in a vertical axis. Thus, in hFSH β-subunit, cysteine 3 is "equivalent" to cysteine 9 of hCG β-subunit.

The information in FIG. 48 can be used to calculate residues that occupy "equivalent" positions in each hormone α-subunit. The crystal structure of hCG is the only one that has been reported. Due to the high similarities in the amino acid sequences of all the glycoprotein hormones, notably their intrasubunit disulfides, it is expected that the hormones of all species will have similar shapes. This idea is also supported by the observation that it is possible to prepare human/bovine α-subunit chimeras that retain epitopes found in regions of their progenitors found in the chimeras. Thus, it is expected that substitution of equivalent residues as defined in this table will lead to intersubunit disulfide bonds that have similar properties to those that have been made and characterized.

Figure 49:
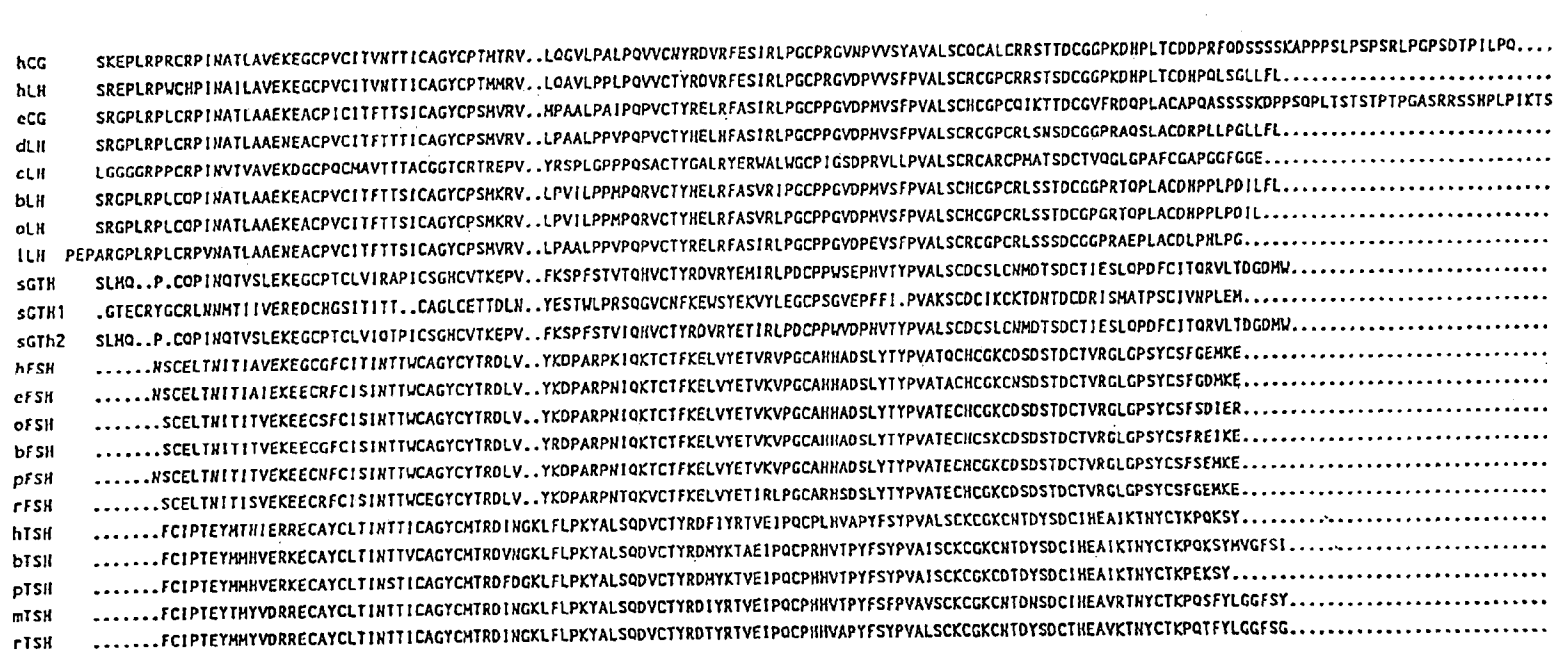

The information in FIG. 49 can be used to calculate residues that occupy "equivalent" positions in each of the vertebrate β-subunits.

The Examples in the present invention teach how disulfide bonds can be introduced into glycoprotein hormones and analogs capable of binding to LH, FSH, and/or TSH receptors. The presence of intersubunit disulfide bonds enhanced the stabilities of hCG and an hCG analog that has significant FSH and TSH activity. Thus, it would be expected that addition of intersubunit disulfides would also stabilize other members and related analogs in this hormone family. When located at hormone sites that are not involved in receptor binding or receptor binding specificity, the disulfides do not prevent hormone function. Indeed, some intersubunit disulfides can potentiate the function of hormone analogs. With one exception (Blithe et al, 1991), the hormone subunits are almost devoid of endocrine activity. Thus, procedures that stabilize the heterodimer are likely to prolong the biological activities of these hormones and would be expected to enhance their therapeutic utility.

The method of improving the stability of heterodimeric glycoprotein hormones according to the present invention involves identifying residues which can be replaced so as to create free cysteines in each of the subunits, which free cysteines have a high potential of forming an intersubunit disulfide bond that would improve the stability of the heterodimer without distorting the overall conformation of the hormone protein. Replacing the residues to create the free cysteines in each of the subunits can be accomplished at the genetic level by replacing the corresponding codons in the nucleotide sequences of the α- and β-subunits. Host cells transformed with recombinant DNA molecules carrying the modified nucleotide sequences encoding the α- and β-subunits operably-linked to a promoter sequence and capable of expressing the modified glycoprotein hormone are cultured, and the modified glycoprotein hormone, referred to as the analog according to the present invention, is expressed. The expressed glycoprotein hormone analog is then recovered and purified according to techniques well-known in the art of glycoprotein hormone purification.

At the genetic level, glycoprotein hormone analogs according to the present invention are generated by any suitable site-directed mutagenesis well-known in the art, such as described in Ausubel et al, *Current Protocols in Molecular Biology*, Greene Publications and Wiley Interscience (New York, 1987-1997), Chapter 8 on mutagenesis of cloned DNA. This *Current Protocols in Molecular Biology* publication, incorporated herein by reference, is an example of a standard reference text setting forth the general principles of recombinant DNA technology.

The nucleotide sequences encoding the α- and β-subunits of the glycoprotein hormone analog as contained in a recombinant DNA molecule can be inserted into appropriate expression vectors capable of expressing the analogs in host cells. In order to be capable of expressing the glycoprotein hormone analog, an expression vector should have specific nucleotide sequences containing transcriptional and translational regulatory information linked to the DNA coding for the subunits in such a way as to permit gene expression and production of the glycoprotein hormone analog. First, in order for the gene to be transcribed, it must be preceded by a promoter recognizable by RNA polymerase, to which the polymerase binds and thus initiates the transcription process.

A DNA is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-non-coding sequences involved with initiation of transcription and translation. There are a variety of promoters in common use for high level protein expression in mammalian and insect cell systems.

The recombinant DNA molecules containing the nucleotide sequences coding for the α- and β-subunits of the analogs of the invention, and the operably-linked transcriptional and translational regulatory signals can be inserted into a vector or vectors which either transiently expresses the subunits in host cells or is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., resistance to antibiotics, or heavy metals, such as copper, or the like. The selectable marker gene can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Okayama (1983).

Expression vectors which are capable of transiently expressing a high level of the desired protein when transfected into eukaryotic host cells, are well-known in the art and are generally either publicly available or commercially available from molecular biology suppliers (e.g, plasmid pcDM8, is available from Invitrogen, San Diego, Calif.; pSVL available from Pharmacia, Piscataway, N.J.; pCI available from Promega, Madison, Wis.; etc.). Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Eukaryotic host cells can be mammalian cells, e.g., human cells, monkey (COS cells), mouse and Chinese hamster ovary (CHO) cells, because they provide post-translational modifications to protein molecules including correct folding, correct disulfide bond formation as well as glycosylation at correct sites. However, insect cells, e.g., baculovirus, can overproduce polypeptides and can also carry out post-translational peptide modifications including glycosylation. Ectopic protein expression in COS, CHO and insect cells are well known in the art and protocols, such as those provided in Ausubel et al, (1987-1997), sections 16.9-16.14, on expression of proteins in insect cells using baculovirus vectors and in mammalian cells, can be suitably used. The transformed host cells expressing α- and β-subunits of a glycoprotein hormone analog can be cultured to produce the analog.

The transformed host cells expressing the α and β-subunits of glycoprotein hormone analog can be cultured to produce the glycoprotein hormone analog which is then recovered and purified according to common and well-known purification techniques for glycoprotein hormones. The amount of the glycoprotein hormone produced can be quantified by a method such as the sandwich immunoassay method described in Example 1. Furthermore, assays for determining the receptor affinity and the biological activity of the glycoprotein hormone analogs of the present invention, such as the radioligand receptor and signal transduction (measuring ability to bind to receptor to elicit a cyclic AMP accumulation response) assays described in Example 1, can be readily performed without undue experimentation.

The glycoprotein hormone analogs according to the present invention have several therapeutic uses. Analogs of hFSH are to be used to induce development of ovarian follicles in preparation for ovulation induction in females. Analogs of hLH and hCG are to be used to induce ovulation of follicles that have initiated development. These analogs are also to be used to induce testes function in males. Furthermore, the glycoprotein hormone analogs according to the present invention can also be used as immunogens to elicit antisera to limit fertility, e.g., contraceptive vaccine. Conversely, antagonist analogs or antibodies to the glycoprotein hormone analogs could also be used to promote fertility, such as when excessive hLH levels appear in some women who have polycystic ovarian disease.

A glycoprotein hormone analog having improved stability, which also retains biological activity and function, e.g., affinity for glycoprotein hormone receptors and hormone potency, such as in the analogs according to the present invention, are quite useful. Not only are the analogs according to the present invention useful for specific therapeutic purposes, but these analogs also provide the superior properties of functional stability in solution and to elevated temperatures, resistance to denaturation by protein denaturants, such as urea, etc. Due to these stability properties, it is expected that the analogs of the present invention would have an improved half-life in vivo.

The glycoprotein hormone analogs of the present invention may be administered to a patient in need thereof by any means that achieves its intended purpose. For example, administration may be by a number of different parenteral routes including, but not limited to, subcutaneous, intravenous, intradermal, intramuscular, intraperitoneal, intranasal, oral, transdermal, or buccal routes. Parenteral administration can be bolus injection or by gradual perfusion over time.

A typical regimen for preventing, suppressing, or treating a condition associated with amyloid or amyloid-like deposits, comprises administration of an effective amount in one or multiple doses of over a period of time up to and including several months to several years.

It is understood that the dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount", it is meant a concentration of glycoprotein hormone analog which is capable of achieving it intended purpose. Such concentrations can be routinely determined by those of skill in the art.

Preparations for parenteral administration include sterile aqueous or non-aqueous solutions, suspensions, and emulsions, which may contain auxiliary agents or excipients which are known in the art.

Pharmaceutical compositions comprising the glycoprotein hormone analogs of the present invention include all compositions wherein the analogs are contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Alfonso Gennaro, Ed., *Remington's Pharmaceutical Sciences*, 18th Edition, Mack Publishing Co. (Easton, Pa., 1990), a standard reference text in this field. Pharmaceutically acceptable vehicles can be routinely selected in accordance with the mode of administration and the solubility and stability of the glycoprotein hormone analogs. For example, formulations for intravenous administration may include sterile aqueous solutions which may also contain buffers, diluents and other suitable additives.

Suitable formulations for parenteral administration include aqueous solutions of the active compounds in water-soluble form, for example, water-soluble salts. In addition, suspension of the active compound as appropriate oily injections suspensions may be administered. Suitable lipophilic solvents or vehicles include fatty oils, for example, sesame oil, or synthetic fatty acid esters for example ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Having now generally described the invention, the same will be more readily understood through reference to the following examples which are provided by way of illustration and are not intended to be limiting of the present invention.

Example 1 hCG Stabilized by an Intersubunit Disulfide Bond Between its Cysteine Knots: hCG(α31-β37)

According to the criteria for intersubunit crosslinking, by disulfide bonds, the data in Table 1B suggested that it would be possible to prepare an analog of hCG stabilized by an intersubunit disulfide between its cysteine knots if a free cysteine were to be created at α-subunit residue 31 and if β-subunit Tyr37 were to be replaced by cysteine. This was accomplished by preparing an analog of hCG β-subunit in which Tyr37 was replaced with cysteine and an analog of the human α-subunit in which Cys7 was replaced with Ser. This latter change disrupted the disulfide normally found in the α-subunit between amino acids Cys7 and Cys31, leaving the free α-subunit cysteine at residue 31 available to form a disulfide bond with the β-subunit cysteine introduced at residue 37. When each of these subunit constructs was expressed in cultured mammalian cells, the cysteines of the α-subunit at residue 31 and of the β-subunit at residue 37 formed an intersubunit disulfide bond.

Formation of the disulfide bond dramatically increased the stability of the heterodimer. Unlike hCG, the crosslinked heterodimer did not dissociate in the presence of urea or low pH. However, the ability of hCG(α31-β37) to be recognized by most monoclonal antibodies, to bind to LH receptors, and to elicit signal transduction was similar to that of hCG. This showed that the presence of the disulfide bond did not disrupt hormone function.

Figure 40:
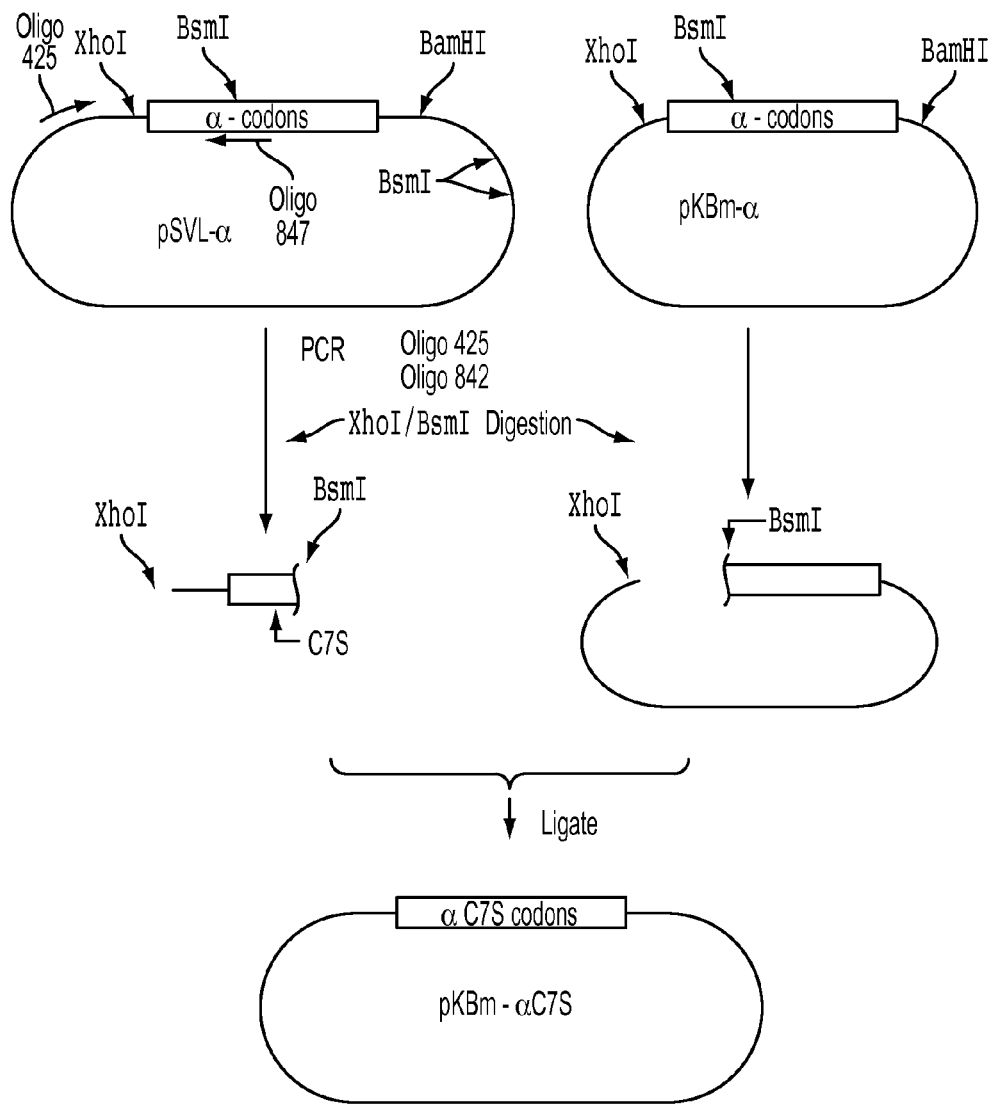
FIG. 40 schematically illustrates the construction of the αC7S codons.

Changing the codon for Cys7 to a codon for serine in the α-subunit was performed in an expression vector (pKBM-hCGα) that has been described in Campbell et al (1991) and that contains the hCG α-subunit cDNA. The pKBM vector is a derivative of the pUC vectors (Yanisch-Perron et al, 1985) in which the polylinker had been replaced with one containing an XhoI site and that permitted transferring of cDNA inserts between pKBM and the expression vector pSVL (Pharmacia, Piscataway, N.J.). Because there is only one α-subunit gene, the cDNA for the α-subunits of hCG, hLH, hFSH, and hTSH contain the same codons and this expression vector will be henceforth referred to as pKBM-α. As shown in FIG. 40, pKBM-α contains a unique XhoI endonuclease restriction site 5' of the α-subunit coding sequence and a unique BsmI endonuclease restriction site near the codons for amino acids 9-11. Polymerase chain reaction (PCR) primers (Oligo425 and Oligo847, Table 2) were designed to bracket this region, change the codon for Cys7 to Ser, and create a new endonuclease restriction site (BspEI) that could be used to facilitate identifying mutant constructs.

TABLE 2

Sequences of the Primers Used to Prepare the Disulfide Crosslinked Analogs

| Oligo363 | 5'-AGCTGTCCTGGAGCTAGGAATCT-3' | SEQ ID NO: 58 |
| --- | --- | --- |
| Oligo364 | 5'-CTAGCCTAGAAGCTCTGACTGTC-3' | SEQ ID NO: 59 |
| Oligo365 | 5'-AGCTGTCCTGGAGCTAGGAATCTCTGTACGGAAGTGTTACTTCTGCTCT-3' | SEQ ID NO: 60 |
| Oligo368 | 5'-CTAGCCTAGAAGCTCTGACTGTCCTAGTTGTGGTTTGTCCAAACTCATC-3' | SEQ ID NO: 61 |
| Oligo425 | 5'-AACCGCCCTGAACACATCCTGCAAAAAGCCCAGA-3' | SEQ ID NO: 62 |
| Oligo435 | 5'-GTGGCTCTCAGCTGTCAATGCGCGCTCTGCCGCAGATCTACCACTGACTGCGGGGTCCCTA-AGGACCAC-3' | SEQ ID NO: 63 |
| Oligo436 | 5'-CCACACGGATCCGAGCTCTTAGCGGGGGTCATCACAGGTCAAGGGGTGGTCCTTAGGGACC-CCGCAGTCAGT-3' | SEQ ID NO: 64 |
| Oligo508 | 5'-ACTGTCCGGGGCTTGGGTCCCTTGACCTGTGATGACCCCCGCTTC-3' | SEQ ID NO: 65 |
| Oligo510 | 5'-GGGACCCAAGCCGCGGACAGTACAGTCAGTACTGTCGCTGTCGCAGAG-3' | SEQ ID NO: 66 |
| Oligo562 | 5'-CCCAAGACCGCGGACAGTGCAGTCAGTGGTAGATCTGCG-3' | SEQ ID NO: 67 |
| Oligo596 | 5'-TGCACTGTCCGCGGTCTTGGCCCAAGCTATTGCAGCTTCGGCGAATTCCAGGACTCCTCTT-CCTCAAAGGCC-3' | SEQ ID NO: 68 |
| Oligo730 | 5'-GATCCTTAAGATTTGTGATAATAACAAGTACTGCA-3' | SEQ ID NO: 69 |
| Oligo758 | 5'-GGTTCTGGTACCGATGACGATGACAAGTCTAAAGAACCGCTGCGGCCGCGTTGCCGCCCCA-TCAATGCCACCCTGGCTGTG-3' | SEQ ID NO: 70 |
| Oligo760 | 5'-CCCACCGGATCCTTAAGATTTGTGATAATAACAAGTACTGCA-3' | SEQ ID NO: 71 |
| Oligo839 | 5'-TGCTTCTCTAGAGCATATCCAACTCCATTGAGATCTAAGAAGACTATGTTGGTCCAAAAGC-AAGTCACTAGTGAGTCCACTTGC-3' | SEQ ID NO: 72 |
| Oligo845 | 5'-CCGGCTGTTGTCCTACCATGACACGTGTGCTGCA-3' | SEQ ID NO: 73 |
| Oligo847 | 5'-CTGTAGCGTGCATTCCGGACTATCCTGCACATCAGGAGC-3' | SEQ ID NO: 74 |
| Oligo850 | 5'-CCATTGAGATCTAAGAAGACTATGTTGGTCCAAAAGGACGTCACTAGTGAGTCCACTTGC-3' | SEQ ID NO: 75 |
| Oligo851 | 5'-ACAAGTACTGCAGTGACAAGCAGTGTGTTGCTCCACTTTGAAACC-3' | SEQ ID NO: 76 |
| Oligo874 | 5'-GCACACGTGTCATGGTAGGACAACAG-3' | SEQ ID NO: 77 |
| Oligo877 | 5'-GATCTGCTAGCTAAGCA-3' | SEQ ID NO: 78 |
| Oligo878 | 5'-CTAGTGCTTAGCTAGCA-3' | SEQ ID NO: 79 |
| Oligo921 | 5'-GATCTAAGAAGACTATGCTTGTACAATGTAACGTTA-3' | SEQ ID NO: 80 |
| Oligo922 | 5'-CTAGTAACGTTACATTGTACAAGCATAGTCTTCTTA-3' | SEQ ID NO: 81 |
| Oligo923 | 5'-GGACTGTACAACAAGTAGTA-3' | SEQ ID NO: 82 |
| Oligo924 | 5'-GATCTACTACTTGTTGTACAGTCCGC-3' | SEQ ID NO: 83 |
| Oligo925 | 5'-TGCCGCAGATCTACTACTTGCTGCGGGGGTCCCAAGGACCAC-3' | SEQ ID NO: 84 |
| Oligo1131 | 5'-CCATTGAGATCTAAGAAGACTATGTTGGTCCAAAAGAACGTCACTAGTGAGTCC-3' | SEQ ID NO: 85 |
| Oligo1132 | 5'-ACAAGTACTGCAGTGACACGCCGTGTGGTTCTCACATTTAAAACCCCCCATTACTGT-3' | SEQ ID NO: 86 |
| Oligo1133 | 5'-CCGGCTATTGTCCTACTATGACGCGTTGTCTGCA-3' | SEQ ID NO: 87 |
| Oligo1134 | 5'-GACAACGCGTCATAGTAGGACAATAG-3' | SEQ ID NO: 88 |
| Oligo1154 | 5'-CTGTGCTATAAG-3' | SEQ ID NO: 89 |
| Oligo1155 | 5'-GTCCTTATAGCACAGATCC-3' | SEQ ID NO: 90 |
| Oligo1161 | 5'-CTTAATACGACTCACTATAGGCTAGCCTCGAG-3' | SEQ ID NO: 91 |
| Oligo1163 | 5'-CATCCCGCGGCACCTAGGACAAAGCGGCTCCTTGGATGCCCATGT-3' | SEQ ID NO: 92 |

The product of the PCR using these primers and pSVL-hCGα (Campbell et al, 1991) as template was digested with XhoI and BsmI and subcloned into the unique XhoI-BsmI sites of pKBM-α using procedures that are well known in the art (Maniatis et al, 1989).

The sequence of a recombinant plasmid containing a BspEI endonuclease restriction site was determined by dideoxy methods (Maniatis et al, 1989) in the region that had been changed by PCR-based mutagenesis. This vector (pKBM-αC7S) encoded a protein having the amino acid sequence shown in FIG. 3. The modified α-subunit cDNA was removed from the pKBM vector by XhoI and BamHI digestion and subcloned into the XhoI-BamHI sites of pSVL to create pSVL-αC7S, a procedure that permitted αC7S to be expressed in COS-7 cells. The coding sequences were also inserted into the XhoI-BamHI sites of another expression vector (pCI) obtained from Promega (Madison, Wis.) that had been modified to facilitate subcloning of this and related constructs. Modification of pCI involved removing its BamHI site and replacing its polylinker (i.e., restriction sites NheI-NotI) with a new polylinker having the following endonuclease restriction sites: NheI-XhoI-EcoRI-MluI-KpnI-XbaI-SalI-BamHI. This permitted subcloning constructs from pKBM and pSVL based vectors into pCI based vectors by removing the XhoI-BamHI fragment containing the desired coding region from either pKBM or pSVL and ligating it to pCI that had been digested with XhoI and BamHI. Further reference to pCI based vectors is intended herein to refer to the modified pCI vector described immediately above. Transfer of the α-subunit coding region from pSVL to pCI created pCI-α and pCI-αC7S, respectively, and was done to facilitate expression in cultured cells.

It is not necessary to use the substitution of serine for cysteine to prepare an α-subunit analog that lacks the ability to form a disulfide between Cys7 and Cys31. Alanine has been used to disrupt this bond (Furuhashi et al, 1994), and it would be expected that replacing Cys7 by any other amino acid would also disrupt the Cys7-Cys31 disulfide bond.

Modification of the hCG β-subunit coding sequence to replace the codon for Tyr37 with that for Cys was accomplished by cassette mutagenesis in the hCG β-subunit cDNA that had been incorporated into a pUC-based vector termed pKBM-hCGβ' (Campbell et al, 1991). This construct contains unique NgoMI and PstI restriction sites at the codons for amino acids 35-36 and 45-46. The mutant codon was introduced by replacing the short piece of DNA between the NgoMI and PstI sites with the cassette created by annealing Oligo845 and Oligo874 (Table 2). This also introduced a PmlI endonuclease restriction site that could be used to facilitate identification of plasmids that contained the mutation.

Subcloning of this cassette into pKBM-hCGβ' (Campbell et al, 1991) was performed by standard methods well-known in the art (Maniatis et al, 1989) and the desired sequence of the mutated region was confirmed by the dideoxy sequencing methods. Since pKBM is not an expression vector, it was subcloned into pSVL to enable this β-subunit construct to be expressed in mammalian cells. This was accomplished by taking the small piece obtained by digestion of pKBM-hCGβ' with XhoI and BamHI and ligating it with the large fragment remaining after digestion of pSVL with XhoI and BamHI to create an expression vector termed pSVL-hCGβ'Y37C. The amino acid sequences encoded by pSVL-hCGβ' and pSVL-hCGβ'Y37C are shown in FIG. 4. These were also subcloned into the modified pCI vector at the XhoI and BamHI sites.

The preparation of these coding sequences could also be accomplished by standard DNA synthesis procedures using commercially available instruments. These procedures can be used to make long oligonucleotides that can be ligated together as described (Campbell et al, 1992). It should be noted that the DNA encoding sequences could also be purchased from one of several companies that specialize in the construction of synthetic oligonucleotides and in preparing synthetic cDNA genes. These include Midland Certified Reagent Company, Midland, Tex., and Genosys Biotechnologies, Inc., The Woodlands, Tex. Expression of these subunits can also be accomplished in cultured mammalian cells (i.e., COS-7 cells) using any of several commercially available vectors such as pSVL (Pharmacia, Piscataway, N.J.) or pCI (Promega, Madison, Wis.) using methods similar to those that have been described (Campbell et al, 1991) and that are common in the art.

The co-expression of pSVL-α and pSVL-hCGβ', pSVL-αC7S and pSVL-hCGβ'Y37C, pCI-α and pCI-hCGβ', and pCI-αC7S and pCI-hCGβ'Y37C in COS-7 cells was performed by routine methods that are well known in the art and that have been described (Campbell et al, 1991). Transfection into COS-7 cells was accomplished by a standard calcium phosphate precipitation method as described (Kriegler, 1990). The COS-7 cells were obtained from the ATCC, Rockville, Md. The day following transfection, the cell culture medium was removed and the medium replaced with serum free DMEM medium. The cells were incubated an additional three days to permit the secreted products to accumulate in the culture media. The media were then centrifuged to remove cell debris and other precipitants, the supernatant transferred to a dialysis bag, and the high molecular weight components concentrated by placing the bag on a bed of hygroscopic powder (Aquacide, Calbiochem, La Jolla, Calif.).

The hCG and crosslinked hCG that had been secreted into the culture media were quantified using a sandwich immunoassay (Moyle et al, 1982) employing antibodies A113 and $^{125}$I-B105 for capture and detection, respectively, and hCG that had been purified from urine being used as a standard. In this assay, anti-hCG α-subunit antibody A113 (1 μg in 0.05 ml) was adsorbed to the surface of a microtiter plate for one hour at 37° C. The non-adsorbed antibody was removed and each well incubated with a solution that contained 0.9% NaCl and 1 mg of bovine serum albumin/ml to block remaining protein adsorption sites. An aliquot (0.05 ml) of culture medium from cells transfected for three days was added to the wells and the hCG or the crosslinked hCG analog was permitted to bind to the adsorbed antibody for 1 hour at 37° C. The non-bound hormone or hormone analog was removed, the wells rinsed with 0.9% NaCl solution, and the captured analyte allowed to react with radioiodinated anti-hCG β-subunit antibody $^{125}$I-B105 that had been prepared as described below. The $^{125}$I-B105 that did not bind to hCG or crosslinked hCG analog was aspirated, and the radiolabel bound to the surface of the microtiter wells was determined using a γ-counter. This assay readily detected 0.1 ng of hCG. It is not necessary to use these particular antibodies for this assay and that there are several commercially available antibodies that can be used as well. Most anti-hCG α-subunit antibodies and any anti-hCG β-subunit antibody that has an affinity for hCG and free hCG β-subunit greater than $10^8 M^{-1}$ will suffice. The latter would include ZMCG13 and ZMCG7 available from Pierce, 3747 North Meridian Road, Rockford, Ill.

Radioiodination of antibodies, hCG and hFSH was accomplished with Iodo-Gen obtained from Pierce Chemical Co, Rockford, Ill. In this procedure, 1.5 micrograms of Iodo-Gen in 50 microliters acetone were added to a small glass tube capable of holding approximately 0.75 ml of fluid and the acetone permitted to evaporate. This left the Iodo-Gen residue coating the bottom of the tube. Afterwards, 10 micrograms of B105 were added, the tube closed with a plastic cap, and 5 microliters containing 250-500 µCi of Na$^{125}$I in 0.2 M sodium phosphate buffer (pH7.2) was added by injecting the solution with a microsyringe through the cap. Twenty-thirty seconds later, 0.1 ml of 0.9% NaCl solution in 0.02M sodium phosphate buffer (pH 7.2) was added and the mixture aspirated and loaded onto a 2 ml column of BioGel P6DG (Bio-Rad, Richmond, Calif.). The free iodine and iodinated protein were separated by gel filtration. The amount of Na$^{125}$I used for iodination varied depending on the ability of the protein to retain its function following radioiodination. Antibodies and hCG were usually radioiodinated to a specific activity of 50 µCI/µg, whereas hFSH was usually radioiodinated to a specific activity of 10-25 µCi/µg.

Table 3 illustrates that the mutation did not disrupt the formation of the crosslinked hCG analog. Cells that had been transfected either with pSVL-containing coding sequences or pCI-coding sequences produced comparable amounts of crosslinked analog and hCG.

TABLE 3

Production of hCG and hCG (α31-β37) by Transfected COS-7 Cells

| hCG or Analog | Concentration |
| --- | --- |
| hCG (pSVL) | 5.07 ng/0.05 ml |
| hCG (pCL) | 4.98 ng/0.05 ml |
| hCG (α31-β37) (pSVL) | 0.94 ng/0.05 ml |
| hCG (α31-β37) (pCL) | 10.66 ng/0.05 ml | hCG and hCG(α31-β37) were measured in sandwich immunoassays relative to an hCG standard using antibodies to the α-subunit (A113) for capture and radioiodinated antibodies to the β-subunit (B105) for detection.

Antibodies A113 and B105 were used in the sandwich immunoassay to determine the production of the crosslinked hCG analog because they recognized regions of the hormone that were expected to be distant from the site of the mutation (Cosowsky et al, 1995; Moyle et al, 1995). The hCG(α31-β37) analog did not bind like hCG to A407 (FIG. 5), an antibody that recognizes an epitope that has been shown to include part of the N-terminus of the α-subunit, the site of the C7S mutation (Moyle et al, 1995). Antibody A407 was obtained from Dr. Robert E. Canfield, Columbia University, New York, N.Y. However, since A407 had been shown to recognize hCG-receptor complexes (Moyle et al, 1995), this small change in hormone conformation was not expected to interfere with the biological activity of the crosslinked hCG analogs.

The biological activities of hCG(α31-β37) and other crosslinked analogs were monitored in radioligand receptor and signal transduction assays. These employed CHO cells that had been transfected with the genes encoding the LH receptor cDNA and that therefore express functional LH receptors on their surfaces. CHO cells were obtained from the ATCC, Rockville, Md. The rat LH receptor cDNA was obtained from a rat ovarian library using the polymerase chain reaction as has been described (Bernard et al, 1990). It should be noted that these LH receptor expressing cells were used as a matter of convenience and that the radioligand receptor assay can be performed with other tissues that express LH receptors. These include homogenates of adult rat testes or homogenates of ovaries obtained from sexually immature rats that have been injected with pregnant mares serum gonadotropin and hCG (both available from Sigma, St. Louis, Mo.). To produce an ovarian preparation that can bind hCG with high affinity, female 21-day old rats would be given a subcutaneous injection of 50 i.u. pregnant mares serum gonadotropin. Approximately 65 hours later, they would be given a subcutaneous injection of 25 i.u. hCG. Seven days later they would be sacrificed, their ovaries homogenized, and aliquots of the homogenate corresponding to one-twentieth of an ovary was used for each assay tube. Cells that express rat LH receptors bind radioiodinated hCG, a tracer that can be prepared as described earlier or purchased from New England Nuclear, Boston, Mass. They also bind unlabeled hCG, a hormone that can be purchased from Sigma Co., St. Louis, Mo. LH receptor expressing CHO cells also synthesize cyclic AMP in response to hCG treatment for 10-30 minutes at 37° C. The cyclic AMP that is produced was measured by a radioimmunoassay (RIA) that is specific for cyclic AMP and that has been described (Brooker et al, 1979).

Figure 6:
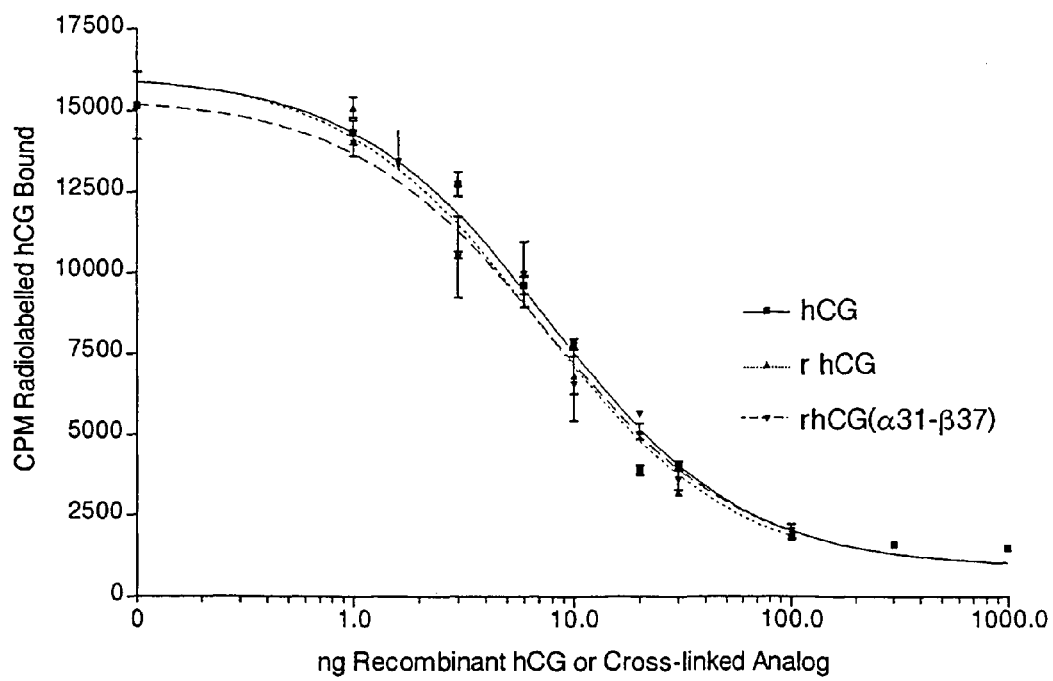
FIG. 6 shows LH receptor binding of hCG(α31-β37). This figure illustrates the abilities of rhCG prepared in cell culture (upward triangles). hCG purified from urine (squares), or hCG(α31-β37) prepared in cell culture (downward triangles) to inhibit binding $^{125}$I-hCG to 200,000 CHO cells that express LH receptors. Values on the ordinate refer to the amount of radiolabeled hCG that was bound to the cells at the end of the incubation. This assay showed that hCG(α31-β37) bound to LH receptors similar to hCG.
Figure 7:
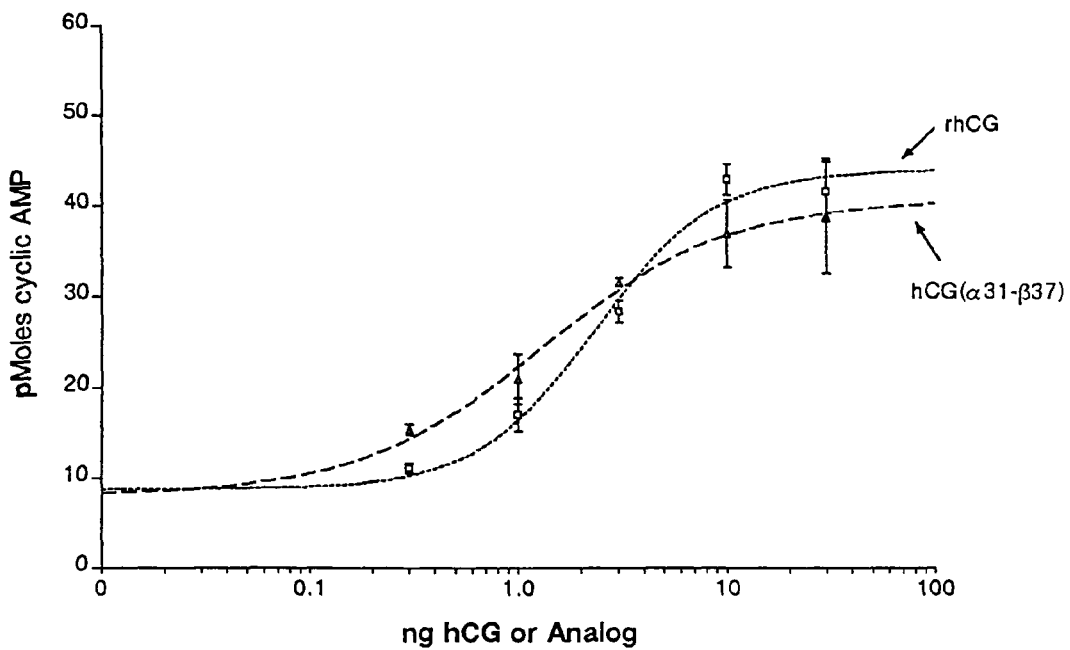
FIG. 7 shows LH receptor signal transduction activity of hCG(α31-β37) and illustrates the abilities of rhCG and hCG (α31-β37) to promote cyclic AMP accumulation in 200,000 CHO cells that express LH receptors. The production of cyclic AMP in response to hormonal stimulation is a widely recognized parameter of signal transduction. This assay showed that hCG(α31-β37) stimulated cyclic AMP accumulation similar to hCG.

The addition of an intersubunit disulfide between residues in the α- and β-subunit cysteine knots of hCG did not destroy the ability of the crosslinked heterodimer to bind to LH receptors or to elicit a cyclic AMP accumulation response. Thus, both hCG and hCG3(α31-β37) were able to block the binding of $^{125}$I-hCG to CHO cells expressing LH receptors (FIG. 6). Both hCG and hCG(α31-β37) were also able to elicit cyclic AMP accumulation in these same cells (FIG. 7). This showed that the presence of this intrasubunit disulfide bond did not disrupt the overall functional activity of hCG.

Figure 8:
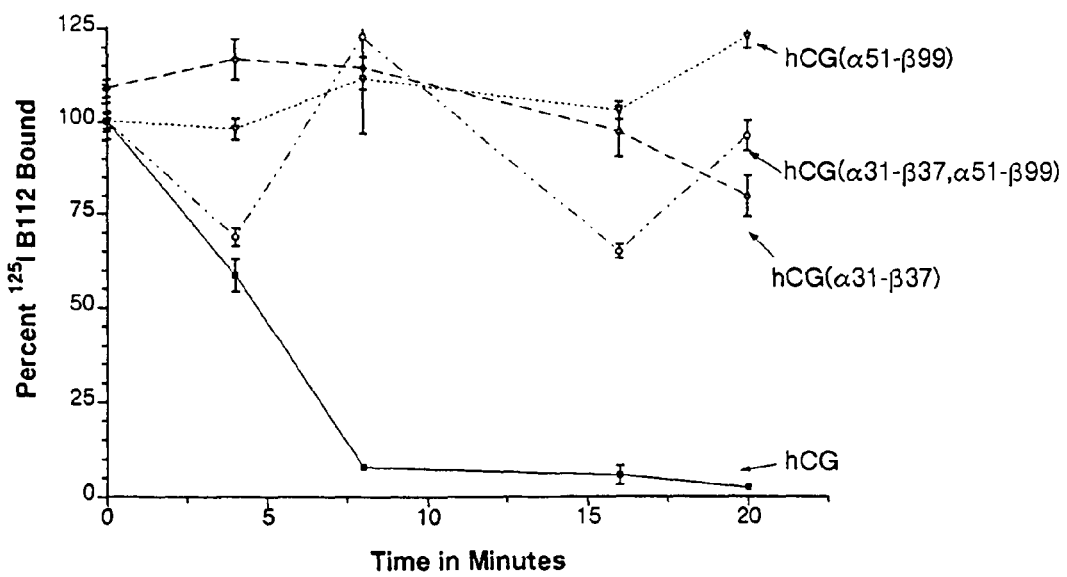
FIG. 8 shows the thermal stabilities of hCG and hCG analogs that contain an intersubunit disulfide bond. Similar amounts of hCG and analogs were incubated at 85° C. for the intervals indicated on the abscissa. The samples were cooled and subjected to a sandwich immunoassay employing anti-hCG α-subunit antibody A113 (capture) and radioiodinated anti-hCG β-subunit antibody B112 (detection) to determine the amount of heterodimer that remained. Values on the abscissa refer to the amount of activity remaining in this assay relative to the starting amount of hCG prior to heating. This assay showed that hCG is rapidly destroyed at 85° C., whereas the crosslinked analogs retained their activities for at least 20 minutes.

The presence of the intrasubunit disulfide bond enabled hCG(α31-β37) to resist treatments with acid, urea, and heat that destroyed hCG. This can be seen from the data in FIGS. 8 and 9). FIG. 8 illustrates the influence of elevated temperature on the stability of the heterodimer monitored in a sandwich immunoassay employing A113 for capture and $^{125}$I-B112 for detection. Note that B105 and B112 bind to an overlapping epitope that involves residues near the turn in the third β-subunit loop (Moyle et al, 1990; Cosowsky et al, 1995), a site distant from the mutations in either the α- or the β-subunits of hCG(α31-β37). In this assay, hCG and hCG (α31-β37) were subjected to a temperature of 85° C. varying intervals up to 20 minutes. Whereas the activity of hCG was virtually destroyed by 7-8 minutes, at least 75% of the activity of the crosslinked analog remained after 20 minutes of incubation (FIG. 8). Since this sandwich immunoassay is dimer-specific, the loss in hCG activity appeared to be due to dissociation of the subunits, a process that is prevented by the presence of the intersubunit disulfide bond.

Figure 9:
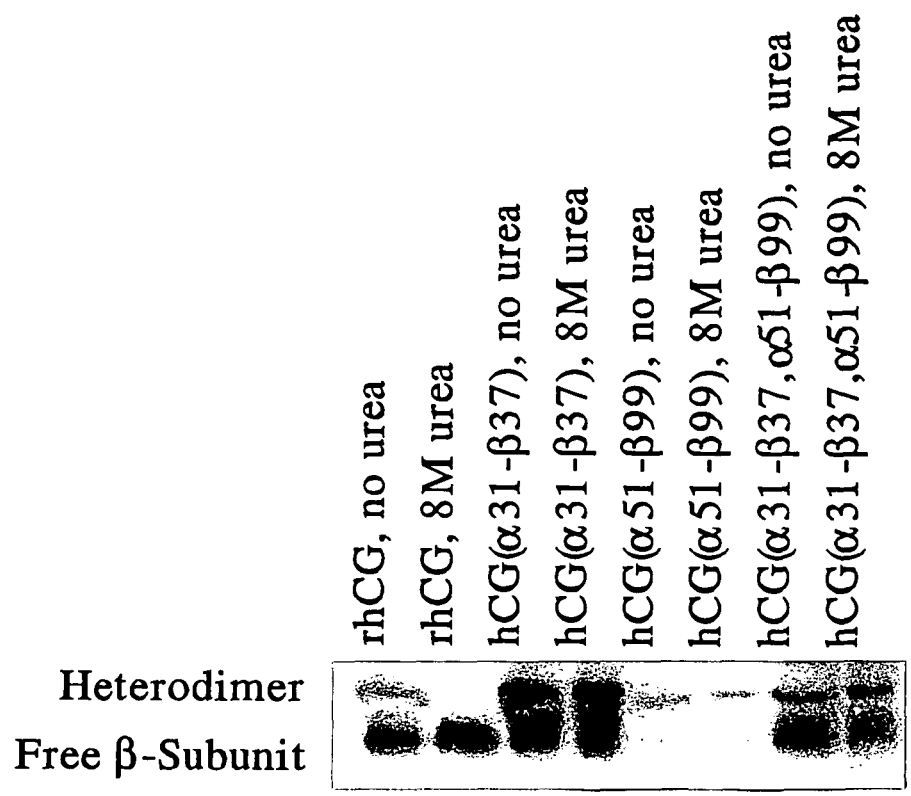
FIG. 9 shows the stability of hCG and crosslinked analogs to urea dissociation. The influence of 8M urea on rhCG and the crosslinked hCG analogs identified at the top of each lane is illustrated. Treatment of hCG with 8M urea is well-known to promote dissociation of its subunits, a finding confirmed here. As can be seen, treatment of the crosslinked analogs with 8M urea did not promote subunit dissociation which would have resulted in loss of the band corresponding to the heterodimer. The positions of the heterodimer and the free β-subunit are noted at the left side of the figure. Following electrophoresis of the untreated and urea treated samples, the proteins in the gel were electroblotted onto nitrocellulose, the remaining non-specific protein sites on the surface of the nitrocellulose were blocked, and the dimer and free β-subunit detected using radioiodinated B105.

Incubation of gonadotropins in high concentrations of urea is well-known to promote subunit dissociation (Pierce et al, 1981). Thus, when hCG was incubated in the presence of 8M urea, it dissociated into its subunits, a phenomenon readily detected with Western blotting (FIG. 9). Mammalian cells that have been transfected with genes encoding the hCG α- and β-subunits often secrete free β-subunit as well as the αβ-heterodimer into the culture media. These can readily be distinguished by sandwich immunoassays that employ an α-subunit-specific and a β-subunit-antibody. The αβ-heterodimer and the free β-subunit can also be distinguished by their sizes in Western blots. Thus, it is possible to monitor the relative amounts of hCG and the free β-subunit in culture media by separating them using polyacrylamide gel electrophoresis and then detecting them in Western blots. This is facilitated by use of a radioiodinated monoclonal antibody that binds hCG and the free hCG β-subunit as shown in FIG. 9. Analysis of culture media from cells that express both the α- and β-subunits of hCG indicated the presence of both the heterodimer (upper band) and the free β-subunit (lower band). Treatment of the culture media with 8M urea caused the heterodimer to dissociate into its subunits. Consequently, the upper band disappeared. Urea did not promote the dissociation of hCG(α31-β37), the disulfide crosslinked heterodimer into its subunits and the band corresponding to the heterodimer remained intact (FIG. 9).

Example 2

A Multi-Functional Glycoprotein Hormone Analog Stabilized by an Intersubunit Disulfide Located between the Cysteine Knots of its α- and β-Subunits The seat-belt is well-known to influence the receptor binding activity of hCG (Campbell et al, 1991; Moyle et al, 1994; Han et al, 1996). Replacement of hCG β-subunit amino acid residues 101-109 with their hFSH counterparts (i.e., hFSH β-subunit residues 95-103) led to a dramatic increase in FSH activity of the analog without impairing its LH activity (Moyle et al, 1994; Han et al, 1996). Indeed, this substitution also enhanced the TSH activity of hCG (Campbell et al, 1997) even though it did not introduce any residues specifically found in hTSH. Studying the influence of intersubunit disulfides on the activities of a related multifunctional analog showed how specific disulfides would influence the activities of lutropins, follitropins, and thyrotropins. This example illustrates how an intersubunit disulfide between the cysteine knots influenced the LH and FSH activity of the hCG analog (CFC101-114), in which hCG β-subunit residues 101-114 were replaced with their hFSH counterparts (i.e., hFSH β-subunit residues 95-108).

Figure 41:
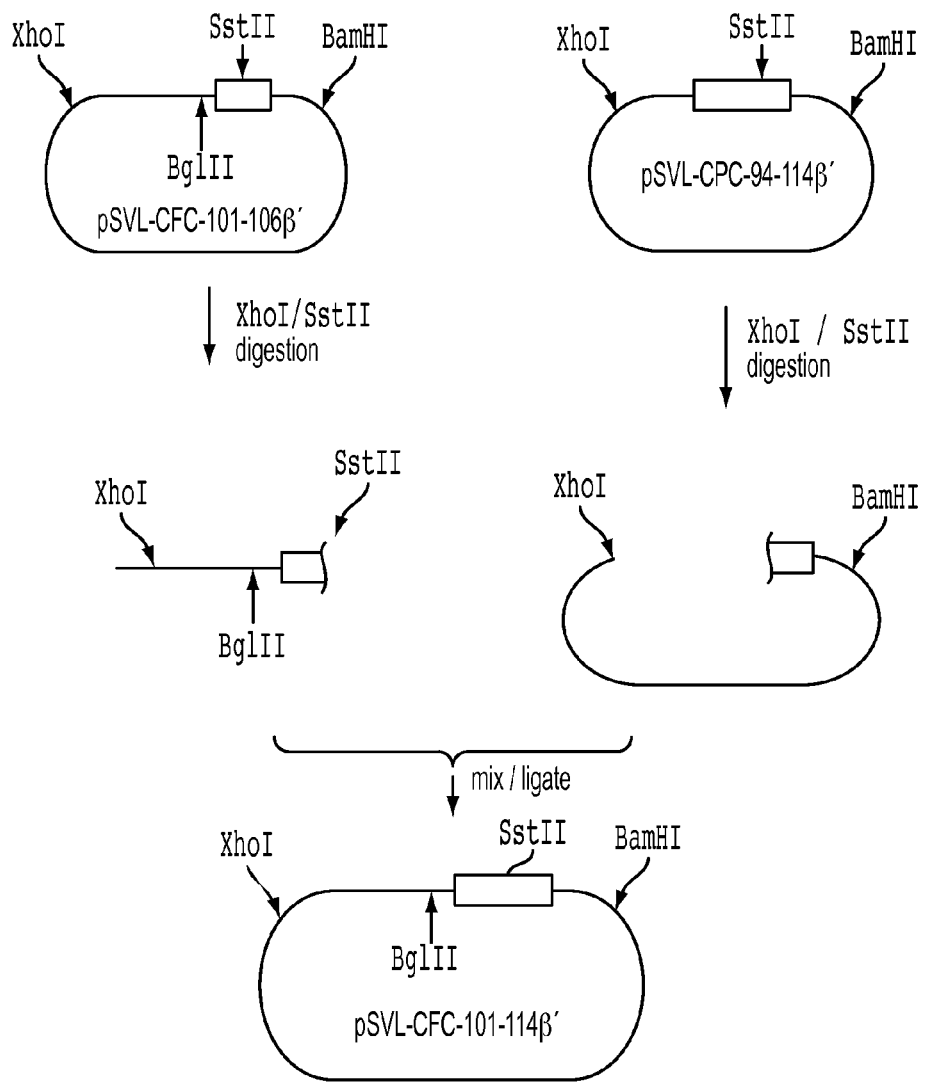
FIG. 41 schematically illustrates the construction of pSVL-CFC101-114β'.
Figure 42:
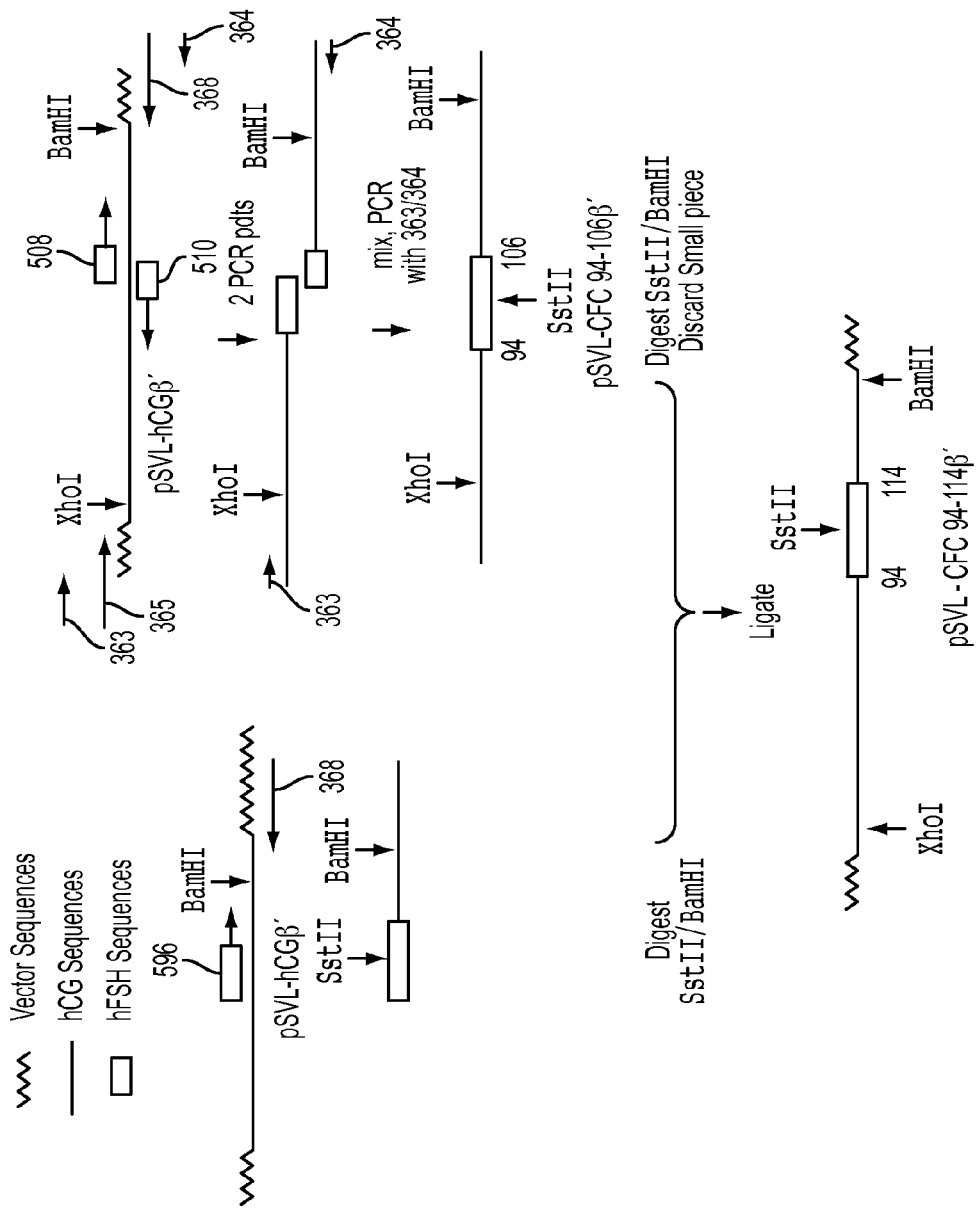
FIG. 42 schematically illustrates the construction of pSVL-CVC94-114β'.
Figure 43:
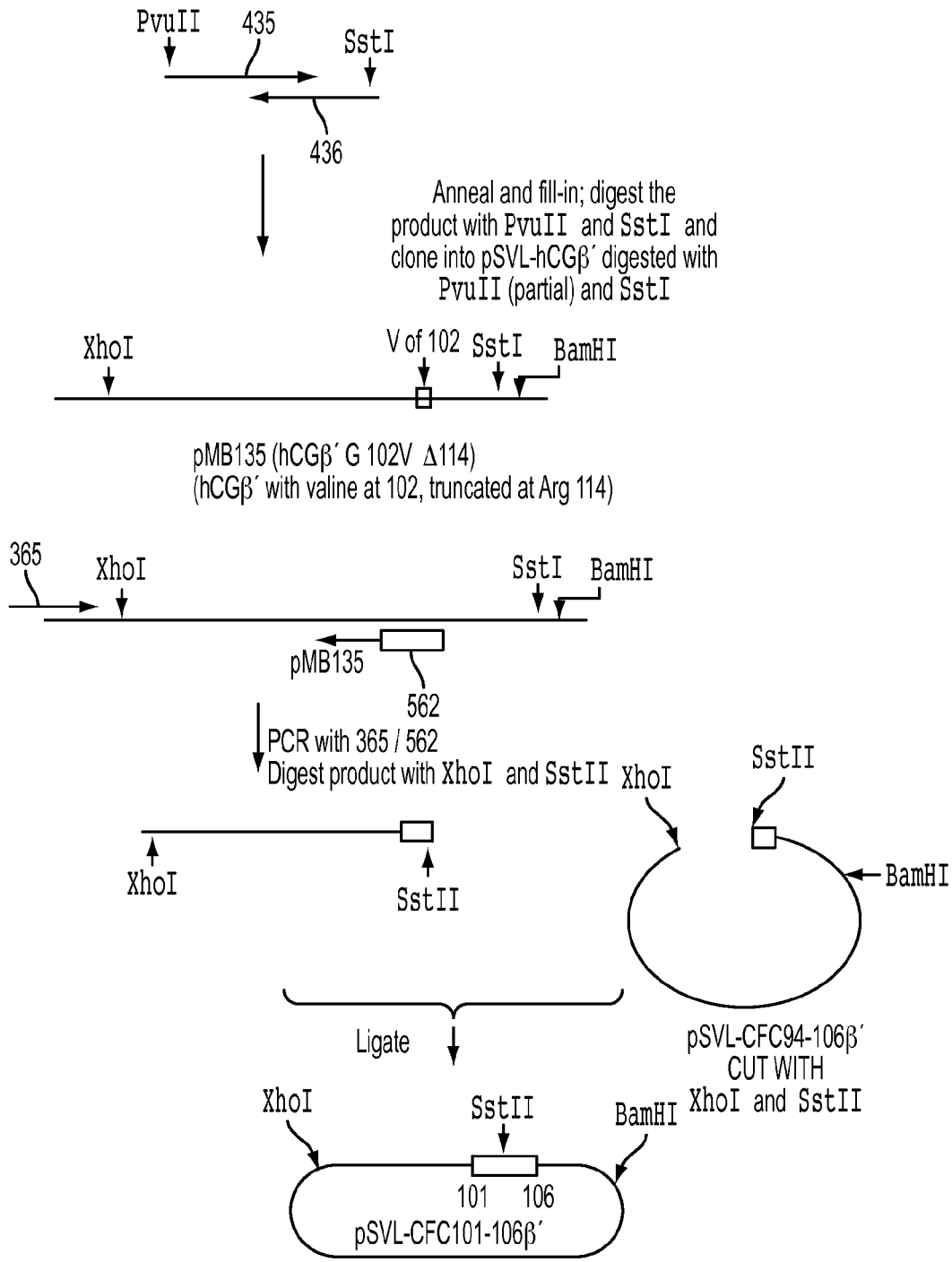
FIG. 43 schematically illustrates the construction of pSVL-CFC101-106β'.

Expression of CFC101-114(α31-β37), required that cells be transfected with vectors encoding αC7S and CFCβ'101-114Y37C. Modification of the α-subunit has been described in Example 1. The DNA sequences of the CFC101-114 β-subunit precursor used to make CFC101-114β'Y37C encoded hCG β-subunit residues 1-100, hFSH β-subunit residues 95-108, and hCG β-subunit residues 115-145 connected sequentially in that order. It had been produced by combining the coding sequences of two hCG/hFSH β-subunit chimeras at their common SstII sites (FIGS. 41-43). The XhoI-SstII fragment of pSVL-CFC101-106β' containing codons for the signal sequence and residues 1-103 of pSVL-CFC101-114β' was subcloned into the XhoI-BamHI fragment of pSVL-CFC94-114β'. This replaced the codons for hFSH β-subunit residues 88-94 found in pSVL-CFC101-114β' with their hCG β-subunit homologs (i.e., residues 94-100) and introduced a BglII site. Each of these coding vectors had been derived from the hCG β-subunit cDNA by modifying codons in the 3' half of the molecule as described next.

pSVL-CFC94-114β' was prepared by PCR mutagenesis of pSVL-CFC94-106β', a vector that encoded hCG β-subunit residues 1-93, hFSH β-subunit residues 88-100, and hCG β-subunit residues 107-145 connected sequentially in that order. The first step in making pSVL-CFC94-114β' was to prepare pSVL-CFCβ'94-106 by SOEing PCR mutagenesis (Ho et al, 1989). A PCR reaction with Oligo508 and Oligo368 (Table 2) as primers and pSVL-hCGβ' (Campbell et al, 1991) as template gave a product containing CFC94-106 β-subunit codons 101-145, the hCG β-subunit termination codon, 3'-untranslated region, a BamHI endonuclease restriction site, and part of the pSVL vector sequence 3' of the BamHI site. A second PCR reaction with Oligo510 and Oligo365 (Table 2) gave a product containing pSVL sequences 5' of its XhoI site, the 5' untranslated region of pSVL-hCGβ (Campbell et al, 1991), the 20 codons for the hCG β-subunit signal sequence, and CFC94-106 β-subunit codons 1-107.

The portions of these PCR products containing CFC94-106 β-subunit codons 101-107 were complementary, a requirement for the overlap extension during "SOEing PCR." These two PCR products were mixed with Oligo363 and Oligo364 (Table 2) and amplified in a third PCR reaction to give a PCR product that encoded the full-length sequence of the CFC94-106 β-subunit that had XhoI and BamHI restriction sites near its 5' and 3' termini, respectively. This PCR product, which also contained a SstII site at the codons for residues 102-104, was cloned into the XhoI and BamHI sites of pSVL to create pSVL-CFC94-106β'. The sequence of the coding region was confirmed by dideoxy sequencing methods.

The final step in making pSVL-CFC94-114β' β-subunit involved PCR using primers Oligo596 and Oligo368 (Table 2) and pSVL-hCGβ' template to create a product that had SstII and BamHI sites near its 5' and 3' ends, respectively. When digested with these enzymes it yielded a DNA fragment that contained codons for hFSH β-subunit residues 97-108 and hCG β-subunit codons 115-145 in that order. This was subcloned into the unique SstII-BamHI sites of pSVL-CFC94-106β' to create pSVL-CFC94-114β' and the portion of the sequence that had been amplified during PCR was confirmed by dideoxy sequencing methods.

Preparation of pSVL-CFC101-106β' began with a vector termed pMB135 that encoded an hCG β-subunit analog truncated at residue 114 and that contained a codon for valine in place of that for Gly102. pMB135 was prepared by annealing Oligo435 and Oligo436 (Table 2) and enzymatically filling-in the 3' ends to create a double stranded cassette that contained PvuII and SstI sites. The latter was 3' of the termination codon. This cassette encoded hCG β-subunit residues 87-101, valine, and hCG β-subunit residues 103-114 in that order, and contained a restriction site for BglII at codons 94-95. It was subcloned into the PvuII-SstI sites of pSVL-hCGβ' and its sequence between the PvuII and SstI sites confirmed by dideoxy sequencing methods. pMB135 was used as a template in a PCR reaction with Oligo562 and Oligo365 (Table 2) to create a PCR product that when digested with XhoI and SstII had the hCG β-subunit cDNA untranslated region and signal sequence, hCG β-subunit codons 1-100, and hFSH β-subunit codons 95-98 in that order. This PCR product was cloned into the XhoI-SstII sites of pSVL-CFC94-106β' to make pSVL-CFC101-106β' and its sequence was determined by dideoxy sequencing methods.

It was clearly not necessary to take this approach to create pSVL-CFC101-114β'. These steps were used for historical reasons. The various intermediate vectors had been made during the course of other experiments and were available for preparation of the vector encoding CFC101-114β'.

Plasmid pSVL-CFC101-114β'Y37C was prepared by combining the 5' "half" of pSVL-hCGβ'Y37C that encoded the Y37C mutation with the 3' "half" of pSVL-CFC101-114β' that encoded hFSH β-subunit amino acids 95-108. This was accomplished by ligating the small piece of pSVL-hCGβ'Y37C obtained by digestion with XhoI and Bsu36I to the large piece created by digestion of pSVL-CFC101-114β' with the same enzymes. This replaced the codons for the signal sequence and amino acids 1-54 of CFC101-114β' with those of hCGβ'Y37C, a change that resulted in the substitution of Tyr37 with cysteine. Subcloning of the XhoI-BamHI fragment into the XhoI-BamHI sites of the modified pCI construct described earlier led to the construct termed pCI-CFC101-114β'Y37C. The amino acid sequences of CFC101-114β' and CFC'101-114β'Y37C are described in FIG. 10.

Production of CFC101-114 and CFC101-114(α31-β37) was accomplished by co-expressing pSVL-α plus pSVL-CFC101-114β; pSVL-αC7S plus pSVL-CFC101-114βY37C; pCI-α plus pCI-CFC101-114β; and pCI-αC7S plus pCI-CFC101-114βY37C in COS-7 cells using methods described in Example 1. CFC101-114 and crosslinked CFC101-114(α31-β37) in the concentrated culture media were quantified using a sandwich immunoassay (Moyle et al, 1982) employing antibodies A113 for capture and either [125]I-B105 or [125]I-B112 for detection with hCG that had been purified from urine was used as a standard. As before, it should be noted that it is not necessary to use these particular antibodies for this assay; commercially available antibodies are available that are expected to work satisfactorily. Most anti-hCG α-subunit antibodies that also have high affinity for hFSH, such as A113 or anti-hFSH α-antibodies that have high affinity for hCG, can be used in this assay. However, because these analogs contain hFSH residues in the part of the seat-belt region that has a major influence on FSH activity (i.e., amino acid residues between the eleventh and twelfth β-subunit cysteines (Moyle et al, 1994)), analogs of CFC101-114 are not recognized by all anti-hCG α-subunit antibodies. This can be seen for A407 (FIG. 11), an antibody that binds hCG but not hFSH. Thus, while A407 bound hCG, it had much less ability to bind CFC101-114 and crosslinked CFC101-114 analogs. A407 also had low ability to bind CFC101-114(α31-β37).

CFC101-114 analogs can be detected by most anti-hCG β-subunit antibodies that have an affinity greater than $10^8 M^{-1}$ for hCG and free hCG β-subunit except those that recognize residues in the β-subunit near the region occupied by FSH residues. Thus, CFC101-114 and analogs were not recognized by Bill, an antibody that has been shown to be highly influenced by hCG residues 108-114 (Cosowsky et al, 1995). Nonetheless, most antibodies that recognize hCG, hLH, free hCG β-subunit, and free hLH β-subunit such as B105 can be used in this assay. In addition, many antibodies that recognize hCG and free hCG β-subunit such as B112 can also be used in this assay. The B105/B112 epitope region is one of the most antigenic regions of hCG in mice and antibodies to this region are commercially available as noted in Example 1.

Figure 12:
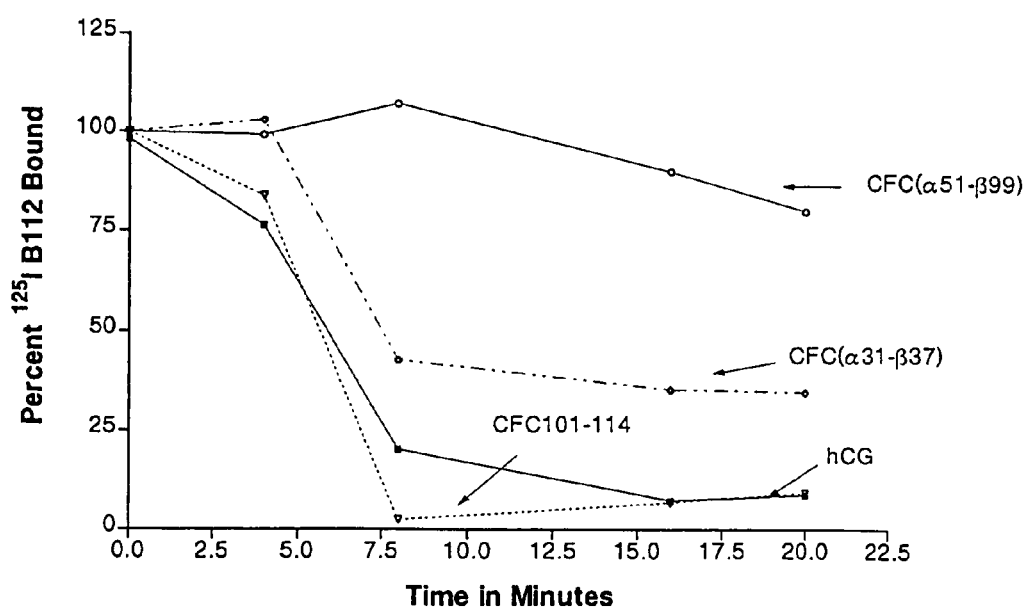
FIG. 12 shows the thermal stabilities of hCG, CFC101-114, and CFC101-114 analogs that contain an intersubunit disulfide bond. hCG, CFC101-114, and CFC101-114 analogs were incubated at 85° C. for the intervals indicated on the abscissa. The samples were cooled and subjected to a sandwich immunoassay employing anti-hCG α-subunit antibody A113 (capture) and radioiodinated anti-hCG β-subunit antibody B112 (detection) to determine the amount of heterodimer that remained. Values on the abscissa refer to the amount of activity remaining in this assay relative to the starting amount of hCG prior to heating. This assay showed that hCG and CFC101-114 are rapidly destroyed at 85° C. whereas the crosslinked analogs retained substantial activity for at least 20 minutes.

The presence of a disulfide crosslink in CFC101-114(α31-β37) increased its thermal stability relative to that of CFC101-114 (FIG. 12). Sandwich immunoassays showed that the activities of hCG and CFC101-114 were nearly destroyed by 7.5 minutes and 15 minutes of heating at 85° C., respectively. However, a substantial amount of CFC101-114 (α31-β37) remained after 20 minutes at the same temperature. This showed that the presence of a disulfide enhanced the stability of this analog. Since this and other analogs that have FSH residues between the eleventh and twelfth β-subunit have both FSH and TSH activities (Campbell et al, 1997), this disulfide bond would also be expected to increase the stability of FSH and TSH.

Figure 13:
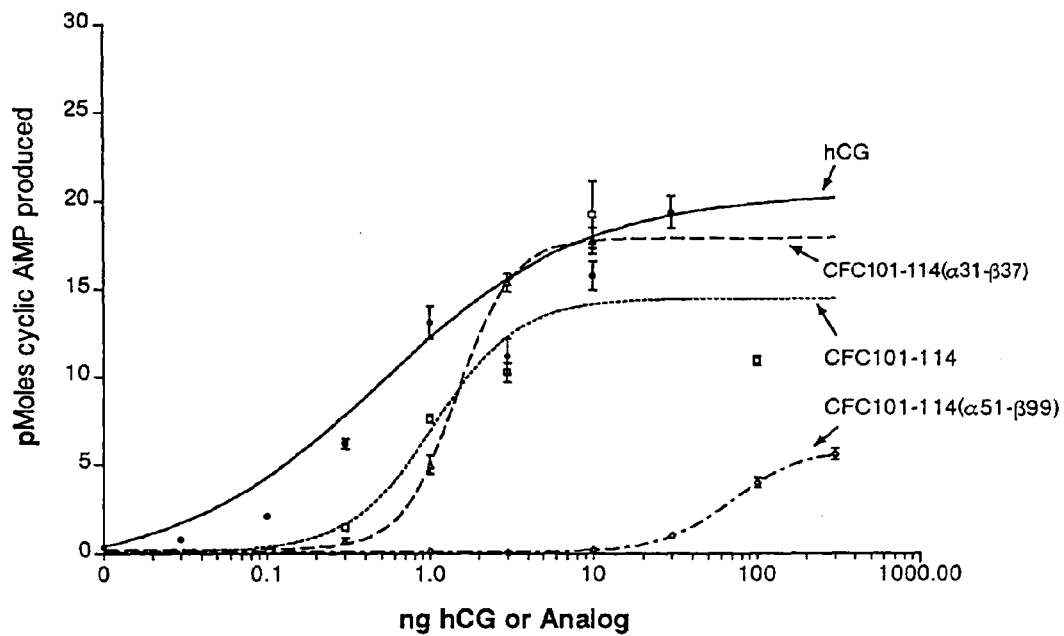
FIG. 13 shows the abilities of hCG, CFC101-114, and CFC101-114 to stimulate cyclic-AMP accumulation in cells expressing LH receptors. This figure illustrates that the potency of CFC101-114(α31-β37) (closed triangles) was at least as great as that of CFC101-114 (open symbols) in assays designed to compare their abilities to stimulate LH receptor signal transduction. While CFC101-114(α51-β99) also stimulated signal transduction, its potency was lower than that of CFC101-114 or CFC101-114(α51-β99). Thus, in contrast to mutations required to prepare the α51-β99 disulfide, mutations needed to prepare the α31-β37 disulfide did not influence signal transduction. The seat-belt is well-known to influence receptor binding specificity. Thus, the data in this figure support the idea that introduction of disulfides into hormone regions thought not to not participate in receptor contacts or binding specificity will have minimal influence on receptor binding or signal transduction. Thus, regions of the hormone that do not contact the receptor and/or do not contribute to specificity of receptor binding will be preferred sites for preparation of disulfide bond crosslinked heterodimers.

CFC101-114 can stimulate signal transduction at LH receptors. Addition of the α31-β37 intersubunit disulfide between the cysteine knots of CFC101-114 did not reduce its activity in this assay (FIG. 13). Thus, both CFC101-114 and CFC101-114(α31-β37) had approximately the same high ability to stimulate cyclic AMP accumulation in assays employing CHO cells that had been engineered to express LH receptors. Thus, the presence of this disulfide bond does not appear to influence the activity of molecules with lutropin activity. The ability of this bond to stabilize these molecules would be expected to confer useful therapeutic properties to lutropins.

Figure 14:
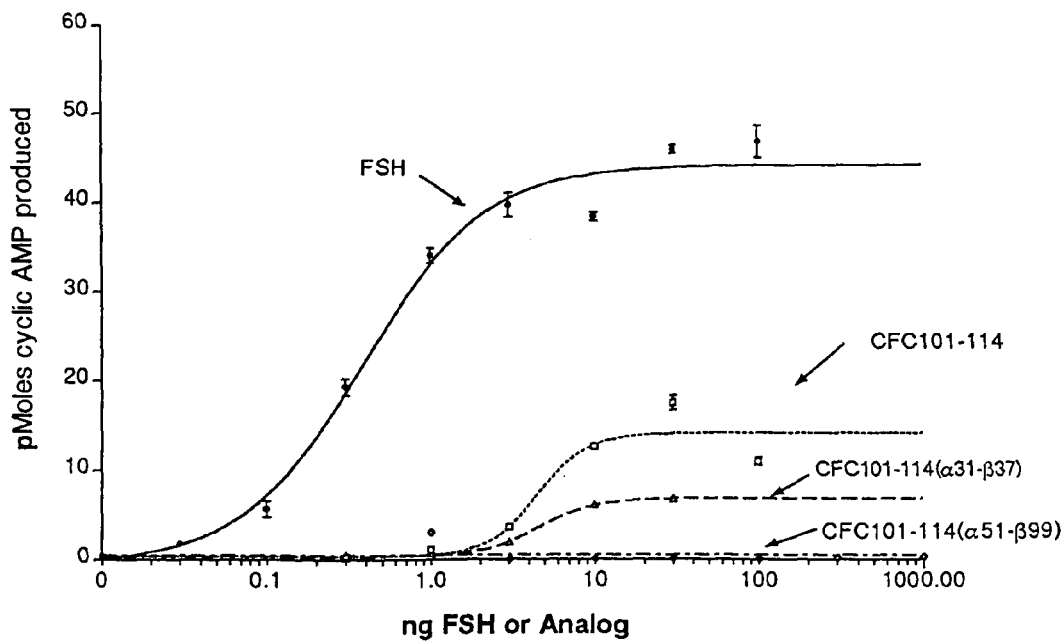
FIG. 14 shows the abilities of hFSH, CFC101-114, and CFC101-114(α31-β37) to stimulate cyclic-AMP accumulation in cells expressing FSH receptors. This figure illustrates that the half-maximal response to CFC101-114(α31-β37) (closed triangles) was similar to that of CFC101-114 (open symbols) in assays designed to compare their abilities to stimulate FSH receptor signal transduction. The activity of CFC101-114(α51-β99) was much lower than that of CFC101-114 or CFC101-114(α51-β99). Thus, in contrast to mutations required to prepare the α51-β99 disulfide, mutations needed to prepare the α31-β37 disulfide had a minimal influence on FSH-induced signal transduction. The seat-belt is well-known to influence receptor binding specificity. Thus, the data in this figure support the idea that introduction of disulfides into hormone regions thought not to not participate in receptor contacts or binding specificity will have minimal influence on FSH receptor binding or signal transduction. Thus, regions of the hormone that do not contact the receptor and/or do not contribute to specificity of receptor binding will be preferred sites for preparation of disulfide bond crosslinked heterodimers.

Although the amino acid sequence of CFC101-114 is much closer to that of hCG than hFSH, CFC101-114(α31-β37) has a much greater FSH activity than hCG, a hormone known to be almost devoid of activity in this assay. Addition of the α31-β37 intersubunit disulfide bond between the cysteine knots of CFC101-114 had only a small influence on its ability to stimulate cyclic AMP accumulation in CHO cells expressing FSH receptors (FIG. 14). Thus, the presence of this disulfide bond would not appear to negatively impact the activity of molecules with follitropin activity and the ability of this bond to stabilize these molecules would be expected to confer useful therapeutic properties to follitropins.

Example 3 hCG Stabilized by an Intersubunit Disulfide Between the Seat-Belt and α-Subunit Loop 2

The distances between the Cα and Cβ carbon atoms of residues in the α- and β-subunits of hCG (Table 1B) suggest that it would be possible to prepare many other additional dimers in which the subunits were tethered by one or more disulfide bonds. Crosslinking of hCG and CFC101-114 between α-subunit residue 31 and β-subunit residue 37 significantly enhanced the stability of the resulting analogs and had minimal influence on their biological activities. To learn if the introduction of a disulfide crosslink in a part of the molecule previously shown to influence receptor binding would alter its stability and activity, disulfide bonds were engineered into hCG and CFC101-114 between α-subunit loop 2 and the seat-belt. These studies showed that introduction of a disulfide into this region of the glycoprotein hormones increased their stability. However, the substitutions that were required to create the disulfide influenced their abilities to interact with receptors and elicit signal transduction. This showed that introduction of a disulfide bond into a part of the hormone that does not participate in receptor interactions or receptor specificity is preferable to maintain high endocrine activity. Since both types of disulfide crosslinked analogs retained their immunological activities, the position of the disulfide may be less important in designing immunogens. The influence of this disulfide on signal transduction may be useful for developing hormone antagonists or immunogens.

Figure 44:
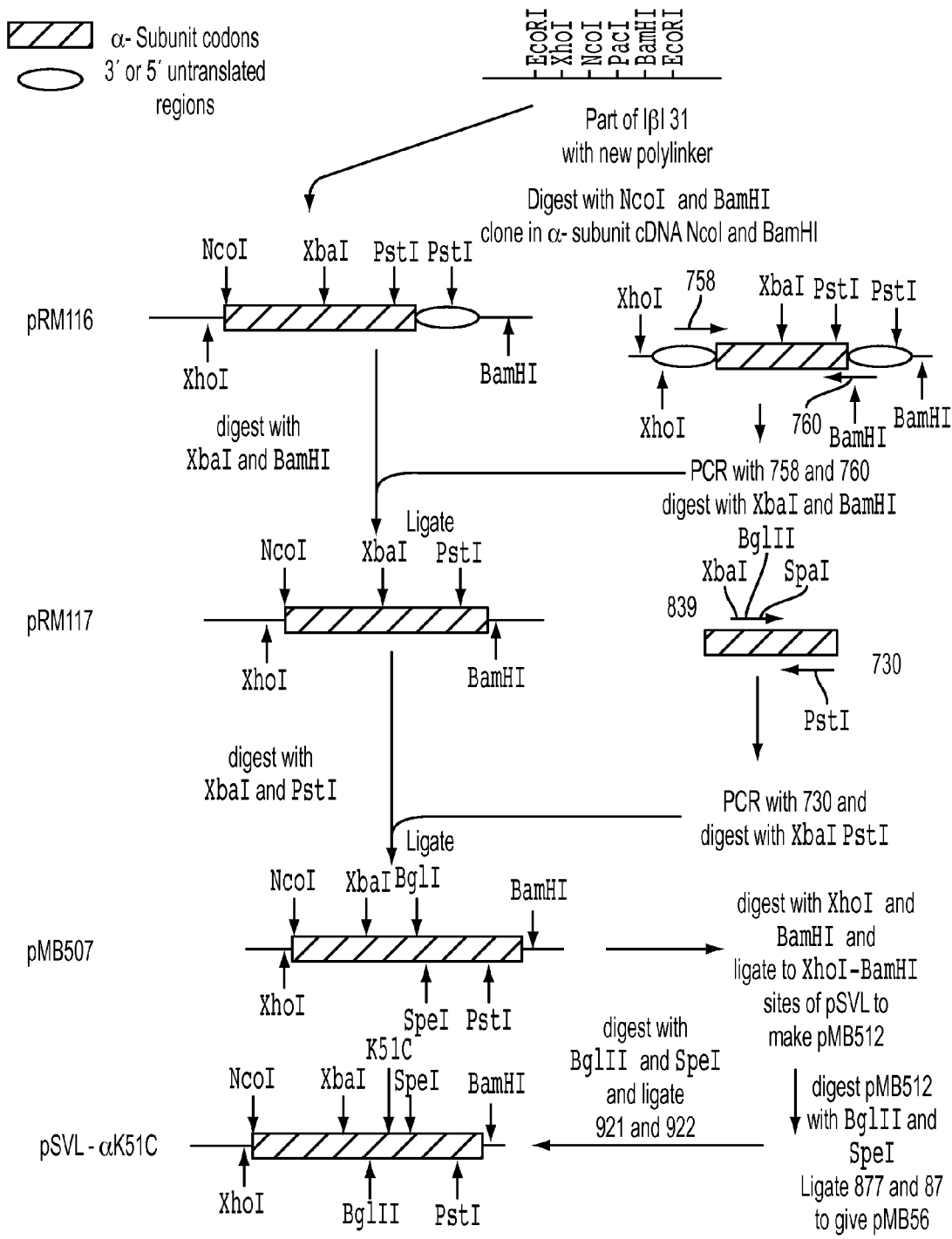
FIG. 44 schematically illustrates the construction of pSVL-αK51C.

To prepare an hCG analog stabilized by an intersubunit disulfide between α-subunit loop 2 and the seat-belt, Lys51 of α-subunit loop 2 and Asp99 of the β-subunit seat-belt were replaced with cysteines. The change in the α-subunit involved cassette mutagenesis of existing vectors that have not been described previously. Therefore, the construction of these intermediate vectors will be described here (FIG. 44).

The polylinker of pIBI31, a cloning vector purchased from International Biotechnologies, Inc. (New Haven, Conn.) was replaced with a polylinker containing restriction enzyme sites EcoRI-XhoI-NcoI-PacI-BamHI-EcoRl to make a vector termed pRM102. pKBM-α was digested with NcoI and BamHI and cloned into the NcoI-BamHI sites of pRM102 to create pRM116 thereby eliminating its 5' untranslated leader sequence and an unwanted 5' XbaI site that had been introduced during the cloning of pKBM-α. Thus, the only XbaI site in pRM116 corresponded to the codons for α-subunit amino acids 34-35. The XbaI-BamHI fragment of pRM116 was replaced with the XbaI-BamHI fragment of a vector that had been created by PCR of the α-subunit cDNA with Oligo758 and Oligo760 (Table 2) to create pRM117. This eliminated the 3' untranslated region found in the α-subunit cDNA, a process that also eliminated the unwanted PstI restriction sites in this region. The only PstI site remaining in pRM17 was located at the codons for residues 83-85. Cloning of the product obtained from PCR of the α-subunit cDNA with Oligo730 and Oligo839 (Table 2) into the unique XbaI-PstI sites of pRM117 led to pMB507. This introduced BglII and SpeI sites into the α-subunit coding sequence at codons 42-43 and 54-55, respectively. Subcloning of the XhoI-BamHI fragment of pMB507 into the XhoI-BamHI sites of pSVL led to pMB512. The fragment of pMB512 between the BglII and SpeI sites was replaced with Oligo877 and Oligo878 (Table 2) to create pMB561. Finally, the BglII-SpeI fragment of pMB512 was replaced with a cassette made by annealing Oligo921 and Oligo922 (Table 2) to create pSVL-αK51C (FIG. 15). This strategy would not be required to make pSVL-αK51C and was used only for historical reasons due to the availability of the various vector intermediates that had been created during other experiments.

The β-subunit analog hCGβ'D99C was prepared by PCR mutagenesis using the pSVL-hCGβ' as template and Oligo368 and Oligo925 (Table 2) as primers. Oligo368 is a reverse primer complementary to a site in pSVL 3' of the BamHI endonuclease restriction site. Oligo925 contains the desired mutation and also creates the BglII site. The PCR product was digested with BglII and BamHI and subcloned into the BglII-BamHI sites of pSVL-CFC101-114β'. This removed the hFSH codons from pSVL-CFC101-114β' and changed Asp99 to cysteine (FIG. 15).

Plasmids pSVL-αK51C and pSVL-hCGβ'D99C were co-expressed in COS-7 cells as described in Example 1. hCG and hCG(α51-β99) were measured in sandwich immunoassays relative to an hCG standard using antibodies to the α-subunit (A113) for capture and radioiodinated antibodies to the β-subunit (B105) for detection. It is not necessary to use these particular antibodies for this assay. Nearly any antibody that recognizes hCG α-subunit in the heterodimer and any β-subunit antibody that recognizes hCG and its free β-subunit with affinities greater than $10^8 M^{-1}$ can be used in this assay. This production of hCG and hCG(α51-β99) by transfected COS-7 cells led to the accumulation of a crosslinked protein analog in the cell culture media readily detected by A113/$^{125}$IB105 or A113/$^{125}$IB112 sandwich immunoassay (Table 4), showing that the mutations needed to introduce the disulfide did not prevent subunit combination.

TABLE 4

Production of hCG and hCG
(α51-β99) by Transfected COS-7 Cells

| hCG or Analog | Concentration |
|---|---|
| hCG (pSVL) | 19.50 ng/0.05 ml |
| hCG (α51-β99) | 4.85 ng/0.05 ml |

Figure 16:
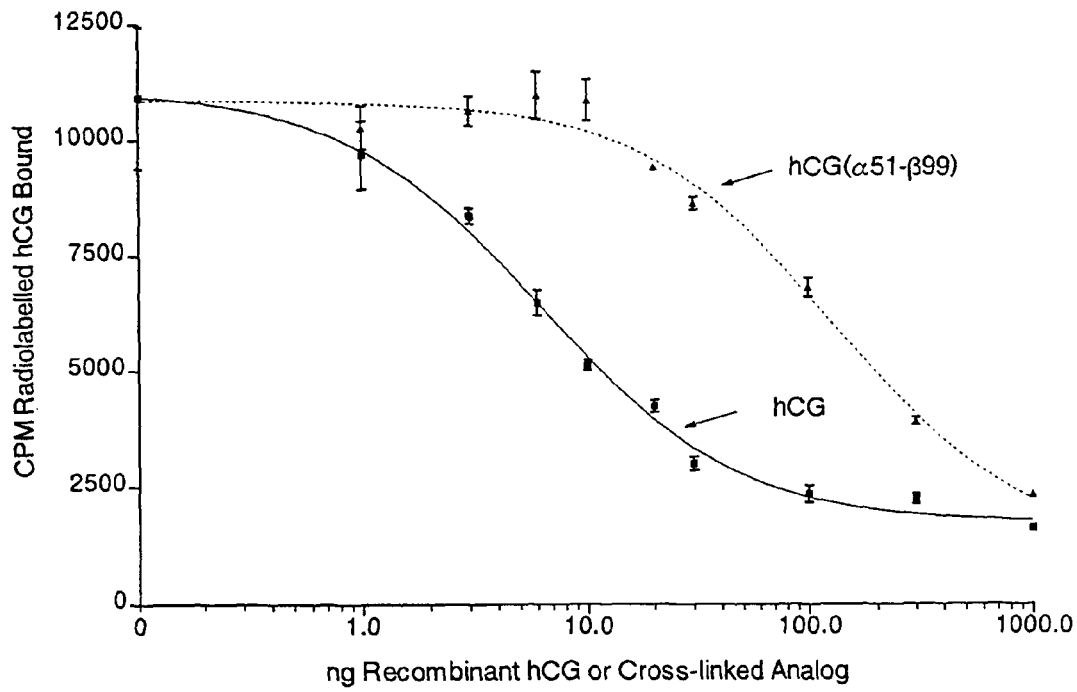
FIG. 16 shows the relative abilities of hCG represented as a solid line with circles, and hCG(α51-β99), represented as a broken line with upward triangles, to inhibit the binding of radiolabeled hCG to CHO cells expressing LH receptors.
Figure 17:
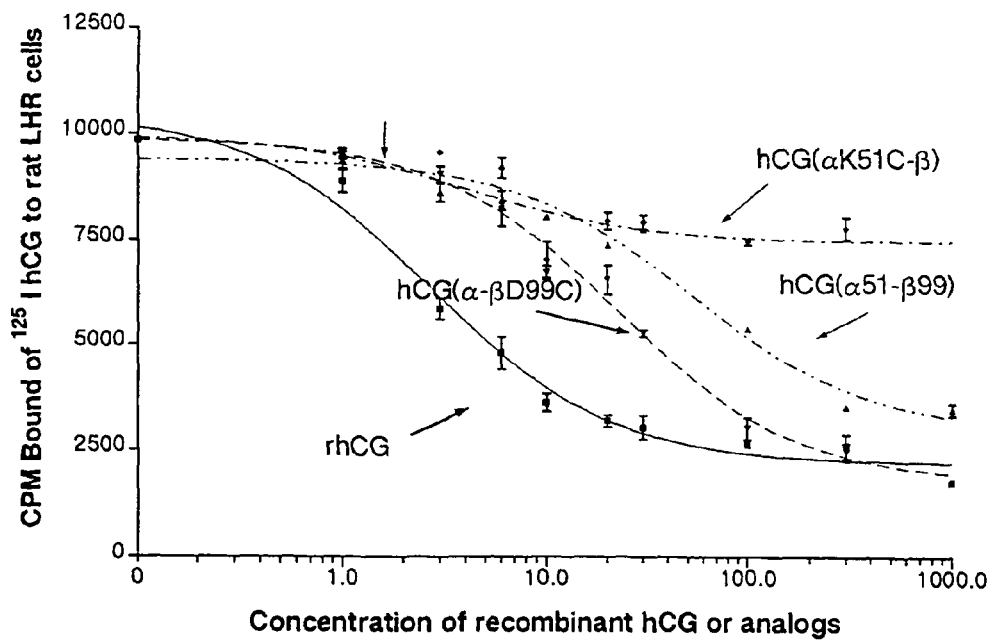
FIG. 17 shows the relative abilities of hCG, represented as a solid line with squares, hCG(α-βD99C), represented as a broken line with downward triangles, hCG(α51-β99), represented as a broken line with upward triangles; and hCG (αK51c-β), represented as a broken line with diamonds, to inhibit the binding of radiolabeled hCG to CHO cells expressing LH receptors.
Figure 18:
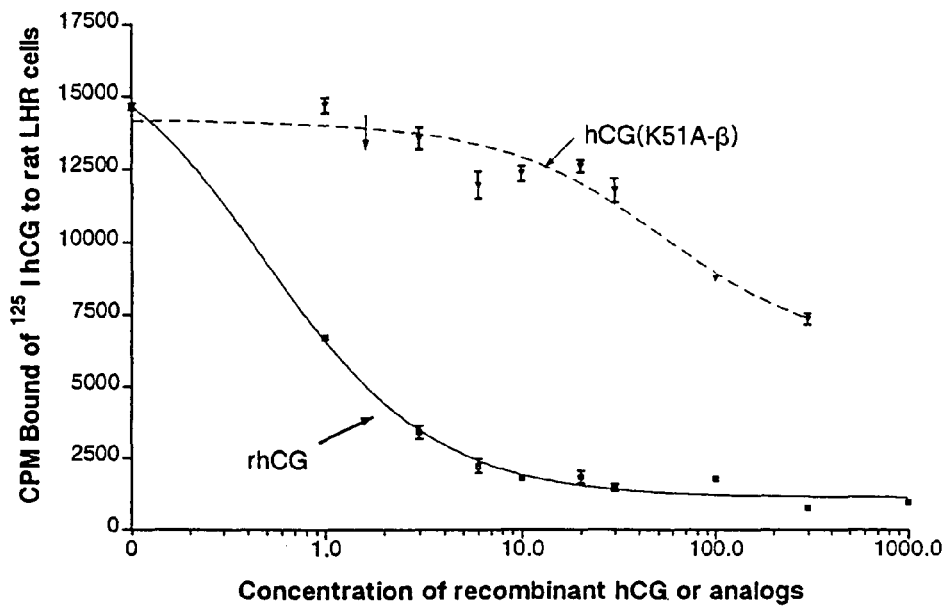
FIG. 18 shows the relative abilities of hCG, represented as a solid line with circles, and hCG(αK51A-β), represented as a broken line with downward facing triangles, to compete with radiolabeled hCG for binding to CHO cells expressing LH receptors.

The biological activity of hCG(α51-β99) was measured in LH receptor binding and signal transduction assays using methods outlined in Example 1. hCG(α51-β99) was able to inhibit the binding of $^{125}$I-hCG to CHO cells expressing LH receptors, albeit with only 5-10% the potency of hCG (FIG. 16). The reduction in affinity for LH receptors caused by the disulfide bond could have been due to 1) the replacement of α-subunit residue Lys51 by cysteine (i.e., substitution of a charged amino acid by a neutral amino acid), 2) the replacement of β-subunit residue Asp99 by cysteine (i.e., substitution of a negatively charged amino acid by a neutral amino acid), or 3) the constraints added by the presence of a covalent bond between the two subunits. Modifications of Asp99 have been shown to reduce or eliminate the LH activity of hCG (Chen et al, 1991). By comparing the LH receptor binding activities of hCG analogs containing an unmodified β-subunit and an α-subunit in which Lys51 had been changed to cysteine (hCG(αK51C-β)) and hCG analogs containing an unmodified α-subunit and a β-subunit in which Asp99 was changed to cysteine (hCG(α-βD99C)) with those of hCG and hCG(α51-β99), it was possible to distinguish the influence of the cysteine substitutions from the influence of the disulfide bond (FIG. 17). These analyses showed that substitution of α-subunit Lys51 with cysteine had a substantial inhibitory influence on the ability of analogs to inhibit $^{125}$I-hCG binding to LH receptors. The activities of hCG(α51-β99) and hCG (α-β99) were similar, demonstrating that the substitution of β-subunit Asp99 with cysteine accounted for most of the reduced LH receptor binding activity of hCG(α51-β99). Changing Lys51 to alanine also reduced the activity of hCG (FIG. 18).

Figure 19:
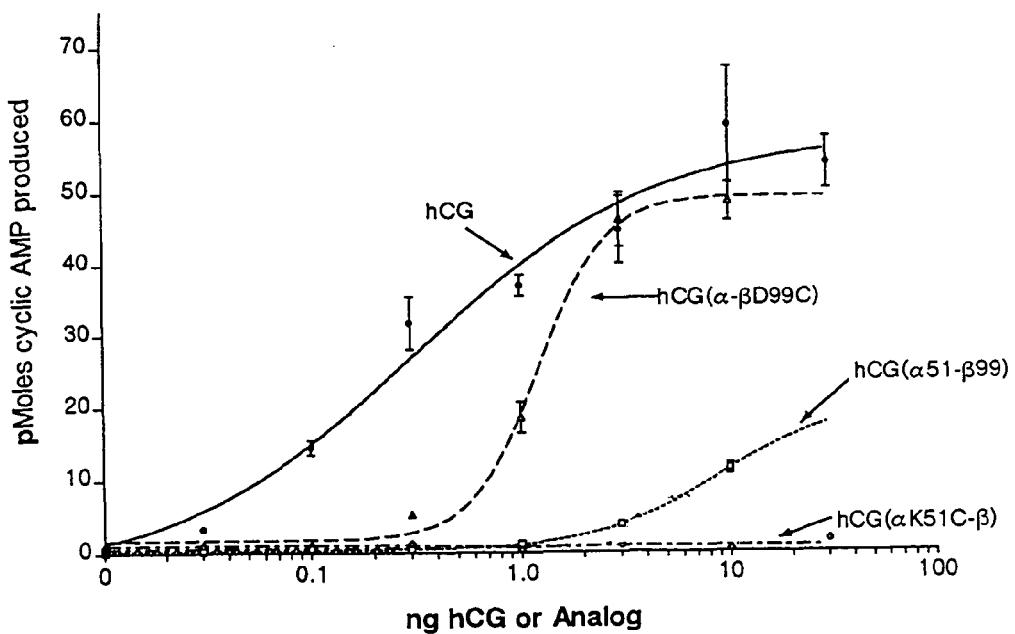
FIG. 19 shows the relative LH receptor signal transduction activities of hCG, represented as a solid line with circles hCG(α51-β99), represented as a broken line with open squares, hCG(α-βD99C), represented as a broken line with upward triangles; and hCG(αK51C-β), represented as a broken line with circles.
Figures 20, 21:
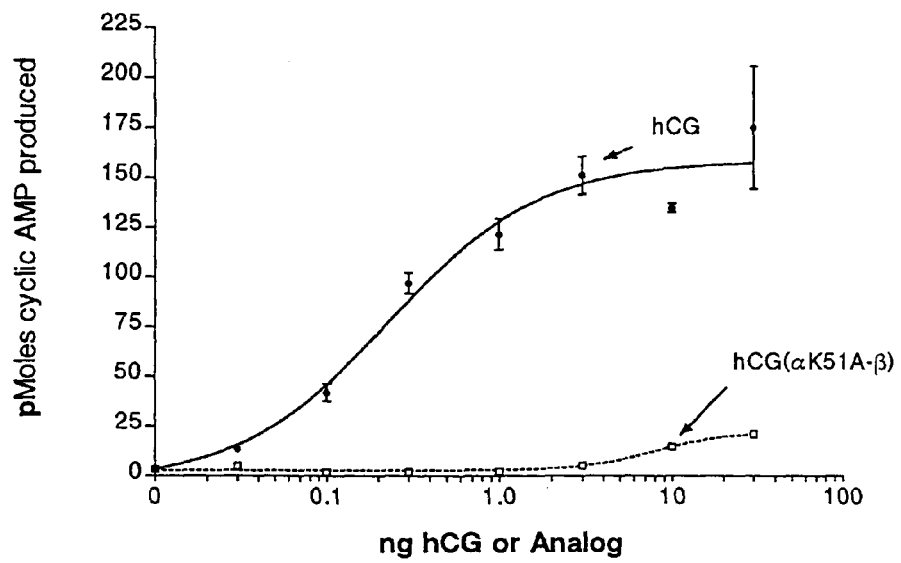
FIG. 20 shows the relative LH receptor signal transduction activities of hCG, represented as a solid line with circles; and hCG(αK51A-β), represented as a broken line with open squares.
FIG. 21 shows the translated amino acid sequence encoded by plasmid pSVL-CFC101-114β'D99C (SEQ ID NO:11). Since this translated protein has the same signal sequence as hCG β-subunit, it is expected to be processed in the same fashion and lead to a secreted protein of 145 amino acids having an N-terminal amino acid sequence SKE. The upper case letter refers to the location of the mutation that was made to introduce the disulfide bond.

The abilities of these hCG analogs to stimulate signal transduction (cyclic AMP accumulation) were also tested. Replacing α-subunit residue Lys51 with either cysteine or alanine caused nearly a complete loss in the ability of the hormone to stimulate cyclic AMP accumulation (FIGS. 19 and 20). Addition of cysteines to both subunits to create hCG(α51-β99) restored significant amounts of activity relative to the analog containing only the single cysteine substitution for α-subunit Lys51 (FIG. 19). Replacement of the β-subunit residue at Asp99 with cysteine by itself had a much lower influence on LH receptor signal transduction. This suggested that the disulfide reduced the relative efficacy of the hCG analogs, a property that may be useful in the design of antagonists.

The presence of an intersubunit disulfide between the seatbelt and α-subunit loop 2 increased the thermal stability of hCG (FIG. 8). It also prevented the subunits from dissociating in the presence of 8M urea (FIG. 9). These observations confirm the beneficial effect of an intersubunit disulfide bond on the stability of the glycoprotein hormones.

Example 4

A Bifunctional Glycoprotein Hormone Analog Stabilized by an Intersubunit Disulfide Between the Seat-Belt and α-Subunit Loop 2

A disulfide bond was created between the seat-belt and the α-subunit loop 2 of CFC101-114, the glycoprotein hormone analog that had the abilities to interact with all three major glycoprotein hormone receptors. This enabled characterization of the relative influence of this region of the protein on interactions with LH and FSH receptors.

The β-subunit expression vector needed for the production of CFC101-114β'(α51-β99), (i.e., pSVL-CFC101-114β'D99C) was prepared by cassette mutagenesis of pSVL-CFC101-114β'. This vector contains a BglII endonuclease restriction site in the codons for amino acids 95-96 and an SstII site in the codons for amino acids 102-104. pSVL-CFC101-114β'D99C was prepared by digesting pSVL-CFC101-114β' with BglII and SstII and replacing the small fragment with a synthetic oligonucleotide cassette obtained by annealing Oligo924 and Oligo923 (Table 2). This also introduced a BsrGI site that was used for selecting recombinant clones. The sequence of the bases changed in the resulting vector, pSVL-CFC101-114β'D99C was confirmed by dideoxy sequencing methods. The amino acid sequence of CFC101-114β'(α51-β99) encoded by this vector is illustrated in FIG. 21.

The co-expression of pSVL-αK51C and pSVL-CFC101-114β'D99C from COS-7 cells was performed as described in Example 1. The dimer was measured in sandwich immunoassays using A113 for capture, radioiodinated B112 for detection, and purified urinary hCG as standard. As in the case of the other analogs, it would not be necessary to use these specific antibodies to detect CFC101-114(α51-β99) in the culture media. Most α-subunit antibodies that were capable of binding to both hCG and hFSH could be used for capture. Most antibodies capable of binding to hCG and free β-subunit, except those that recognized residues involving the sequence that had been changed to FSH, could be used for detection. An example of an antibody that could not be used is B111 (Cosowsky et al, 1995).

Figure 5:
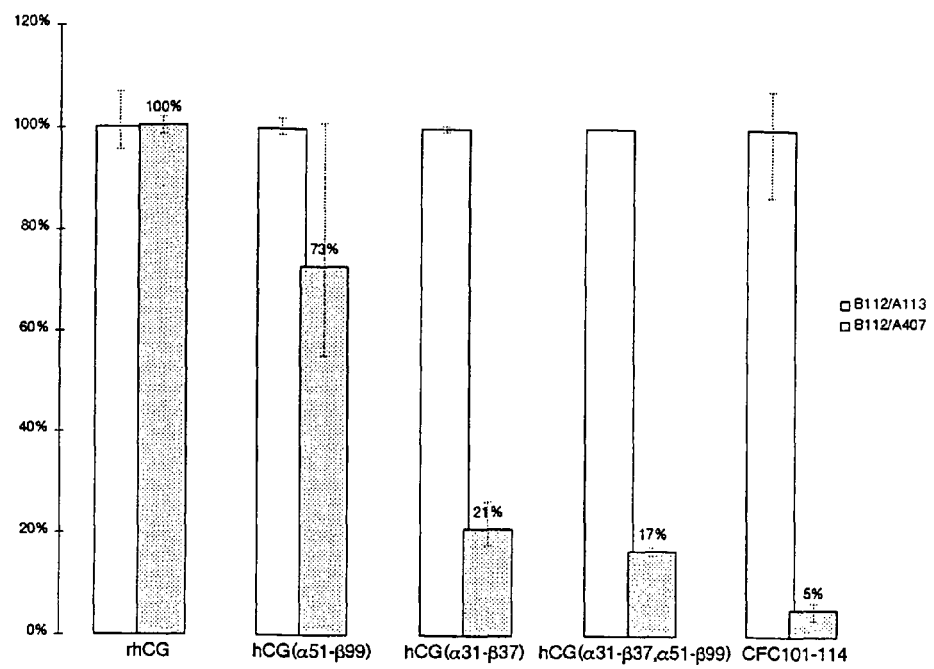
FIG. 5 shows the influence of C7S mutation in α-subunit on binding of α-subunit monoclonal antibodies A113 and A407. Recombinant hCG prepared in cell structure (rhCG) and the analogs indicated below each pair of bars and whose structures are described in the Examples were subjected to sandwich immunoassays employing B112 as capture antibody and either radioiodinated A113 or A407 as detection antibodies. B112 recognizes an epitope that contains residues in β-subunit loop 3; A113 recognizes epitopes that involve residues in α-subunit loop 1; and A407 recognizes epitopes that involve residues in the N-terminus of the α-subunit and a different part of a α-subunit loop 1. The epitopes for A407 and A113 do not overlap since both can bind to hCG at the same time. The bar at the right of each pair refers to the B112/A407 assay. The bar at the left refers to the B112/A113 assay. As seen here, the mutation of C7S had a much greater effect on binding of A407 than on the binding of A113.
Figure 11:
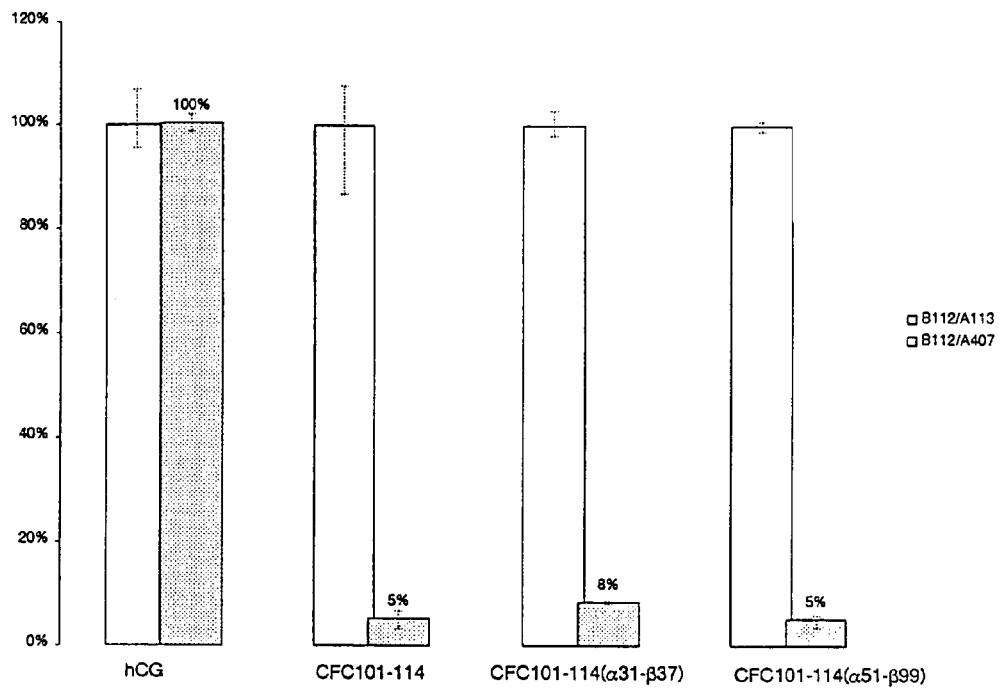
FIG. 11 shows the influence of the α31-β37 and α51-β99 disulfides on the binding α-subunit monoclonal antibodies A113 and A407 to a bifunctional hCG/hFSH chimeric analog. hCG and the CFC101-114 analogs indicated below each pair of bars and whose structures are described in the Examples were subjected to sandwich immunoassays employing B112 as capture antibody and either radioiodinated A113 or A407 as detection antibodies. B112 recognizes an epitope that contains residues in β-subunit loop 3; A113 recognizes epitopes that involve residues in α-subunit loop 1; and A407 recognizes epitopes that involve residues in the N-terminus of the α-subunit and a different part of α-subunit loop 1. The epitopes for A407 and A113 do not overlap since both can bind to hCG at the same time. The bar at the right of each pair refers to the B112/A407 assay. The bar at the left refers to the B112/A113 assay. As seen here, neither the α31-β37 nor the α51-β99 disulfide restored binding activity of A407 to CFC101-114.

A407, an α-subunit monoclonal antibody that recognized a determinant on the N-terminal portion of the α-subunit in hCG (Moyle et al, 1995) does not recognize CFC101-114 nearly as well as it binds hCG (FIG. 5). It was thought that this was due to the influence of the seat-belt on the overall interaction of the glycoprotein hormone α- and β-subunits that may be involved in the control of receptor binding specificity. Addition of the disulfide between α-subunit residue 51 and β-subunit residue 99 did not enable the resulting analog to be recognized by A407 (FIG. 11).

Like the other disulfide crosslinked analogs, CFC101-114 (α51-β99) was also found to be more stable than its parental precursors (i.e., CFC101-114 and hCG) in thermal denaturation assays (FIG. 12). Indeed, it appeared that the presence of the disulfide between α-subunit residue 51 and β-subunit residue 99 increased the stability of the protein more than the disulfide between α-subunit residue 31 and β-subunit residue 37.

Figure 22:
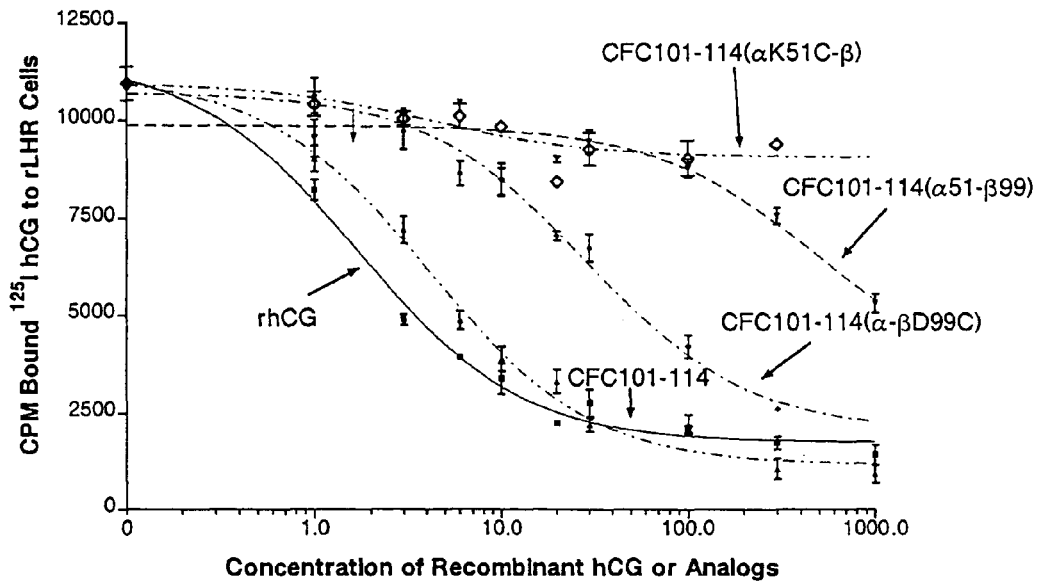
FIG. 22 illustrates the relative LH receptor binding activities of hCG, represented as a solid line, CFC101-114, represented as a broken line with upward triangles, CFC101-114 (α51-β99), represented as a broken line with downward facing triangles, CFC101-114(α-βD99C), represented as a broken line with closed diamonds, and CFC101-114(βK51C-β), represented as a broken line with open diamonds.
Figure 23:
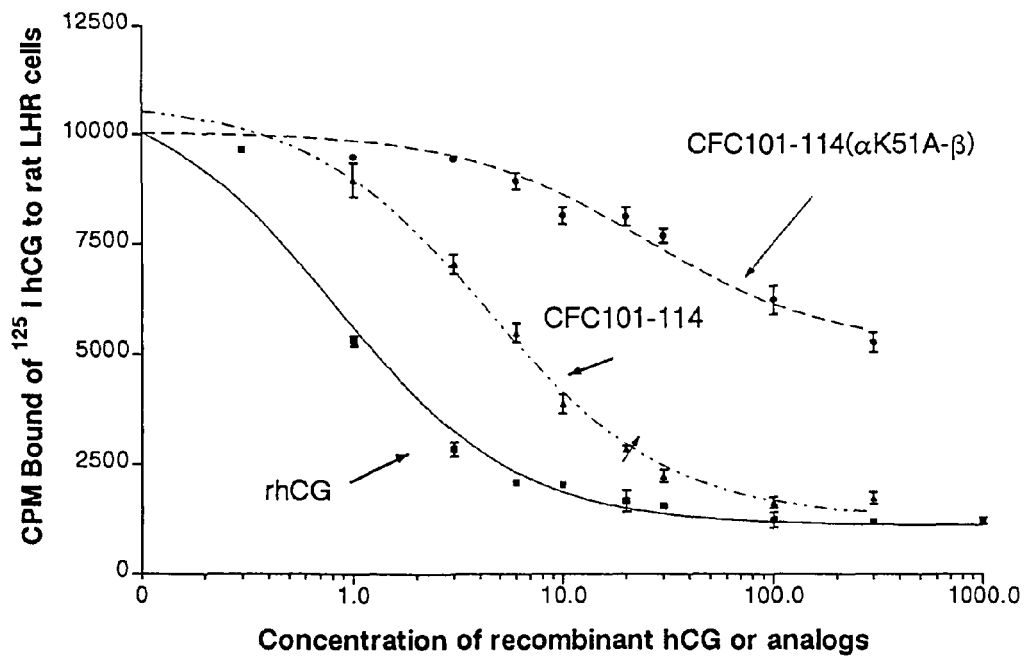
FIG. 23 illustrates the relative LH receptor binding activities of rhCG, represented as a solid line with squares; CFC101-114, represented as a broken line with upward facing triangles; and CFC101-114(αK51A-β), represented as a broken line with circles.

The presence of the disulfide bond between the seat-belt and α-subunit loop 2 of CFC101-114(α51-β99) reduced its ability to bind to LH receptors (FIG. 22). Thus, whereas CFC101-114 was nearly as effective as recombinant hCG in inhibiting the binding of radiolabeled hCG to LH receptors, CFC101-114(α51-β99) was approximately 100-fold less active. The relative importance of the individual subunit mutations and the disulfide bond were compared by monitoring the activities of CFC101-114, CFC101-114(α51-β99), CFC101-114(αK51C-β), CFC101-114(αK51A-β), and CFC101-114(α-βD99C). This comparison showed that substitution of α-subunit Lys51 with cysteine or alanine per se had a substantial inhibitory influence on receptor binding (FIGS. 22 and 23). Thus, the activity of CFC101-114 (αK51C-β) was relative to that of CFC101-114(α51-β99). Unlike its effect on the LH activity of hCG, substitution of CFC101-114 β-subunit Asp99 with cysteine accounted for only a part of the reduced ability of CFC101-114 (α51-β99) to bind LH receptors. Nonetheless, CFC101-114(α51-β99) was substantially more active than CFC101-114 (αK51C-β), an effect that could not be explained by presence of cysteine in the α-subunit in place of Lys51.

Figure 24:
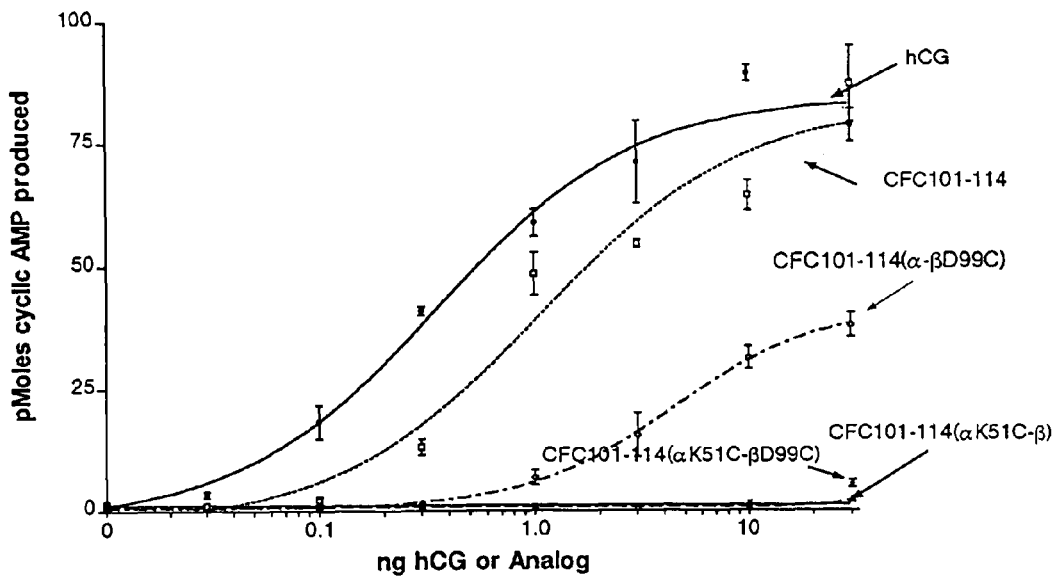
FIG. 24 illustrates the relative LH receptor signal transduction activities of hCG, represented as a solid line with closed circles; CFC101-114, represented as a broken line with open squares; CFC101-114(α-βD99C), represented as a broken line with diamonds, CFC101-114(αK51C-β99C), represented as a solitary point; and CRC101-114(αK51C-β), represented as a line closest to abscissa.
Figure 25:
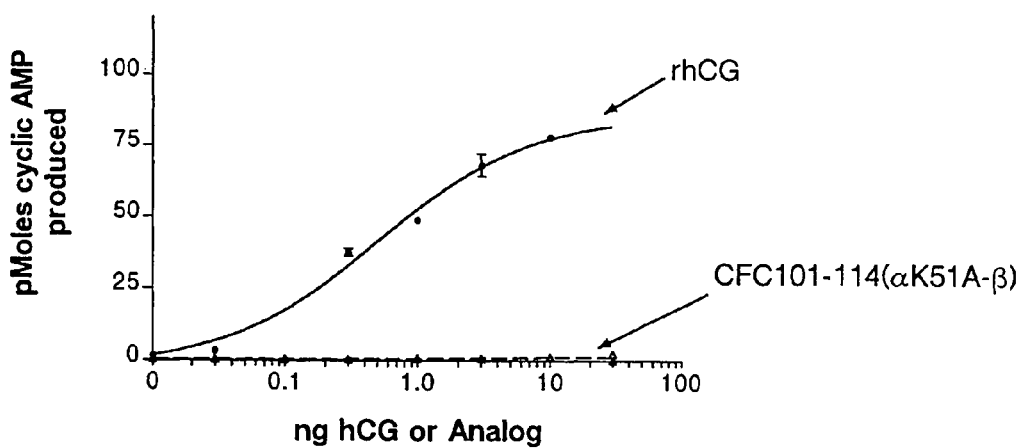
FIG. 25 illustrates the relative LH receptor signal transduction activities of rhCG, represented as a solid line with circles; and CFC101-114(αK51A-β), represented as a broken line with upward facing triangles.

Studies were also performed to determine the influence of the seat-belt-α-subunit disulfide bond on the signal transduction activities of CFC101-114 (FIGS. 24 and 25). CFC101-114 was only slightly less potent in stimulating signal transduction at LH receptors than hCG (FIG. 24). However, CFC101-114(α51-β99), the disulfide crosslinked analog was active only at the highest concentration tested. In confirmation of studies discussed earlier, this appeared primarily due to the change of α-subunit Lys51 to cysteine the analog in which only β-subunit Asp99 was converted to cysteine (i.e., CFC101-114(α51-β99)) retained substantial activity. As in the case of the binding assays, where the disulfide was able to offset some of the loss in activity caused by the replacement of α-subunit Lys51 by cysteine or alanine, the intersubunit disulfide bond restored some signal transduction (FIG. 24).

Figure 26:
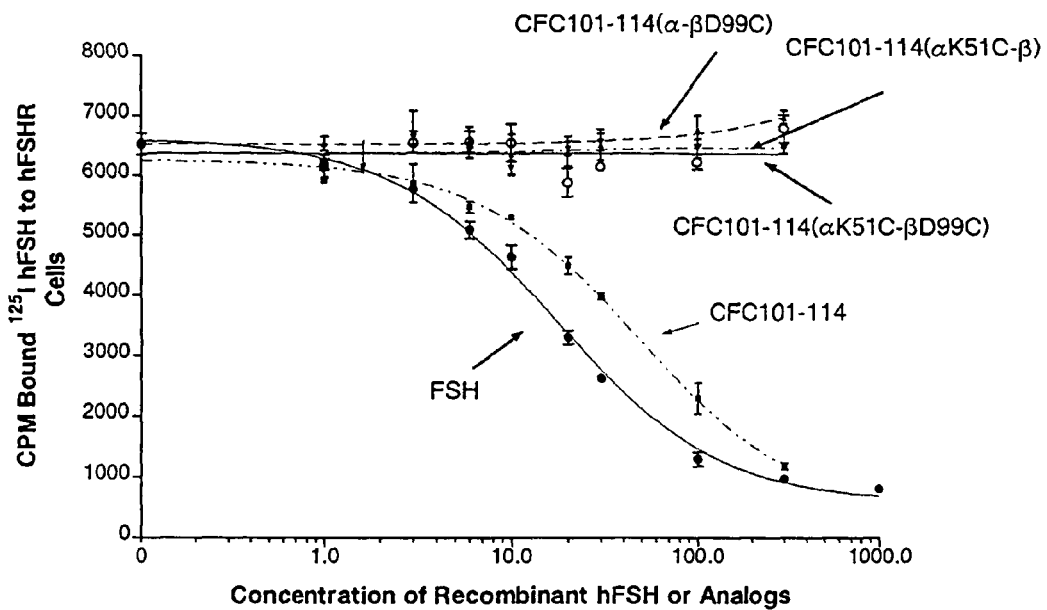
FIG. 26 illustrates the relative abilities of hFSH, represented as a solid line with circles; CFC101-114, represented as a broken line with squares; CFC101-114(α-βD99C), represented as a broken line with upward triangles; CFC101-114 (αK51C-β99C), represented as a solid line with downward triangles; and CFC101-114(αK51C-β), represented as a solid line with open symbols, to inhibit binding of $^{125}$I-hFSH to CHO cells expressing hFSH receptors.
Figure 27:
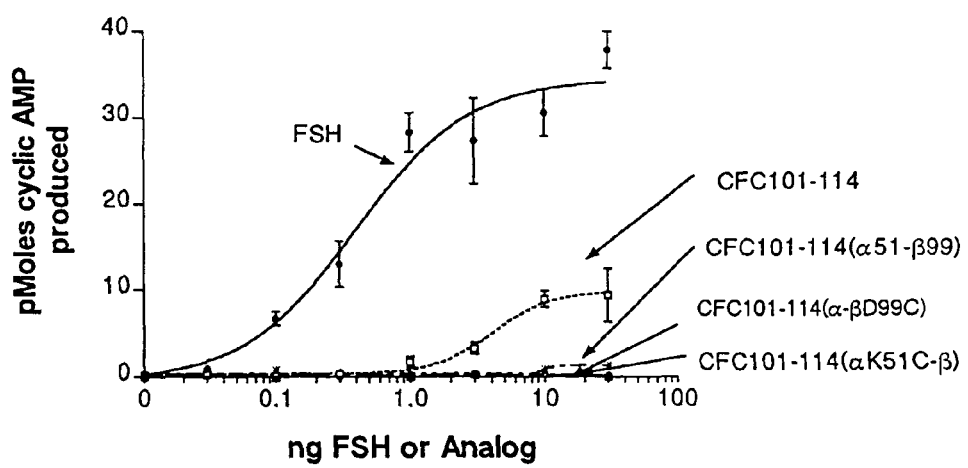
FIG. 27 illustrates the relative abilities of hFSH, represented as a solid line with circles and CFC101-114, represented as a broken line with open symbols to stimulate signal transduction in CHO cells bearing hFSH receptors. The signal transduction activities of CFC101(α51-β99), CFC101-114(α-βD99C) and CFC101-114(αK51C-β) were too low to be detected at the concentrations of analogs employed.
Figure 28:
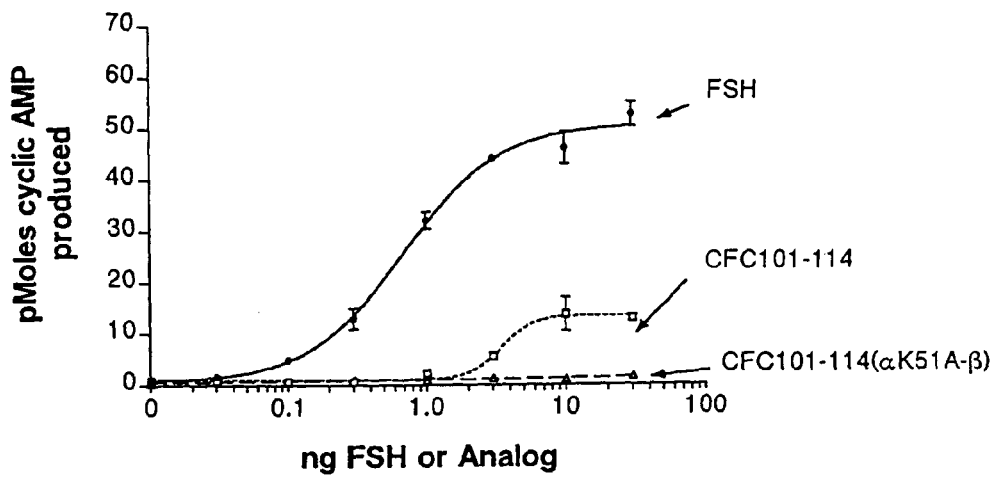
FIG. 28 illustrates the relative abilities of hFSH, represented as a solid line with circles, CFC101-114, represented as a broken line with open squares, and CFC101-114 (αK51A-β), represented as a broken line with upward triangles, to stimulate signal transduction in CHO cells expressing hFSH receptors.

CFC101-114 had substantial activities in FSH assays. However, the cysteine substitutions needed to create the seat-belt-α-subunit loop 2 disulfide crosslink had a greater effect on the FSH activity of CFC101-114 than on its LH activity (FIGS. 26, 27, and 28) and it was not possible to distinguish the influence of the disulfide bond per se. Thus, analogs in which only α-subunit Lys51 or β-subunit Asp99 had been changed lost most of their FSH activities. The finding that mutations of β-subunit Asp99 had a greater influence on FSH activity than on LH activity supports previous observations on the role of the seat-belt in LH and FSH activity (Han et al, 1996; Baird et al, 1993). These reports suggest the region of the seat-belt that influences LH receptor binding is near amino acids 94-96 whereas that which influences FSH receptor binding is near amino acids 101-109.

Example 5 hCG Stabilized by Disulfides from Examples 1 and 3

To learn how the introduction of multiple disulfides into the glycoprotein hormones would influence their biological activities, analogs of hCG were made that contained the disulfides shown in Examples 1 and 3. These analogs were prepared by exchanging portions of the expression vectors that have been described in Examples 1 and 3. pCI-α(C7S, K51C) was prepared by digestion of pSVL-αC7S and pSVL-αK51C with BsmI, separating the small and large fragments produced in each digestion by agarose electrophoresis, and ligating the large fragment from pSVL-αC7S to the small fragment obtained from pSVL-αK51C. The resulting construct was digested with XhoI and BamHI and ligated into pCI that had a modified polylinker and that was described in Example 1. pCI-hCGβ'(Y31C,D99C) was prepared by digesting pSVL-hCGβ'D99C and pCI-hCGβ'Y37C with AocI (an isochizamer of Bsu36I) and BamHI, separating the small and large pieces by agarose electrophoresis, and ligating the small piece derived from pSVL-hCGβ'D99C to the large piece derived from pCI-hCGβ'Y37C. The amino acid sequences of the analogs encoded by these vectors are illustrated in FIG. 31.

pCI-α(C7S,K51C) and pCI-hCGβ'(Y31C,D99C) were co-expressed in COS-7 cells as described in Example 1. Protein secreted into the culture media were concentrated and monitored by sandwich immunoassay, also as described in Example 1 except that radioiodinated B112 was used in place of B105. The presence of multiple disulfide bonds did not prevent the glycoprotein hormone from folding or being secreted from the cells as shown by the presence of analog in the culture media (Table 5). hCG(α31-β37,α51-β99) were measured in sandwich immunoassays relative to an hCG standard using antibodies to the α-subunit (A113) for capture and radioiodinated antibodies to the β-subunit (B112) for detection. The analog was not recognized well by antibody A407, a probable consequence of the mutation near the N-terminus of the α-subunit. Since this region of the protein is not required for hormone activity, lack of this epitope appeared to be of little consequence. The upper case letters in FIG. 31 refer to the locations of the mutations that were introduced to form the disulfide bonds.

TABLE 5

Production of hCG and hcG
(α31-β37, α51-β99) by Transfected COS-7 Cells

| hCG or Analog (pCL) | Concentration |
| --- | --- |
| hCG | 35.33 ng/0.05 ml |
| hCG (α31-β37, α51-β99) | 36.60 ng/0.05 ml |

Figure 29:
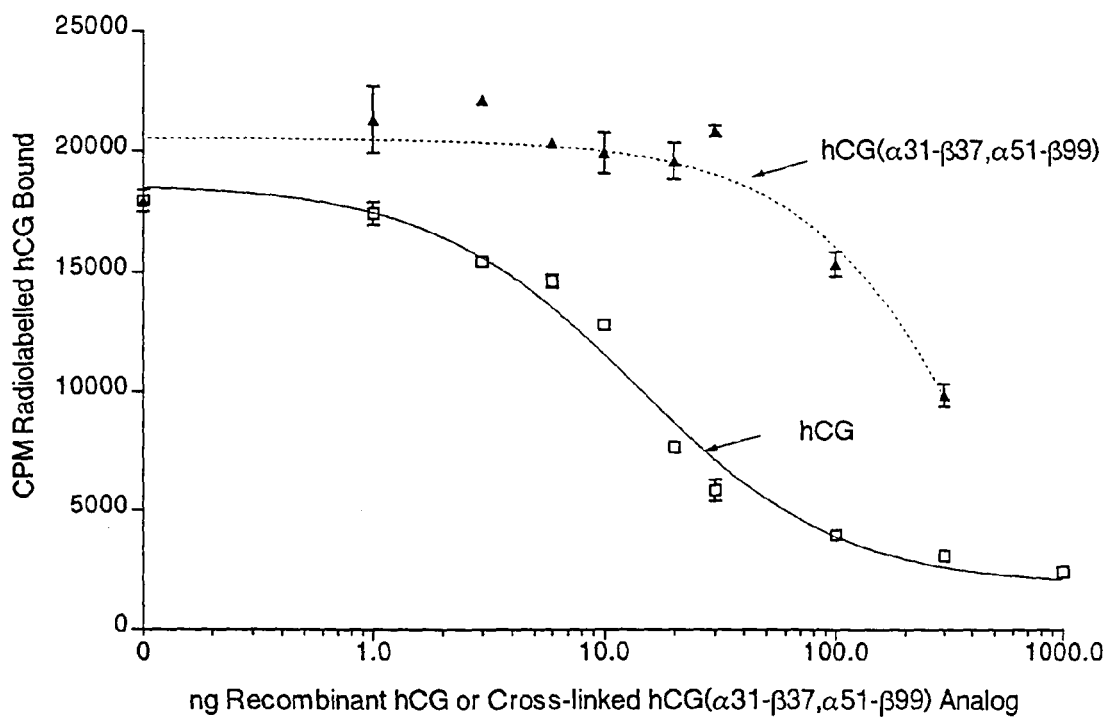
FIG. 29 illustrates the abilities of hCG, represented as a solid line with downward triangles, and hCG(α31-β37, α51-β99), represented as a solid line with circles to stimulate signal transduction in CHO cells expressing LH receptors.
Figures 30, 31A, 31B:
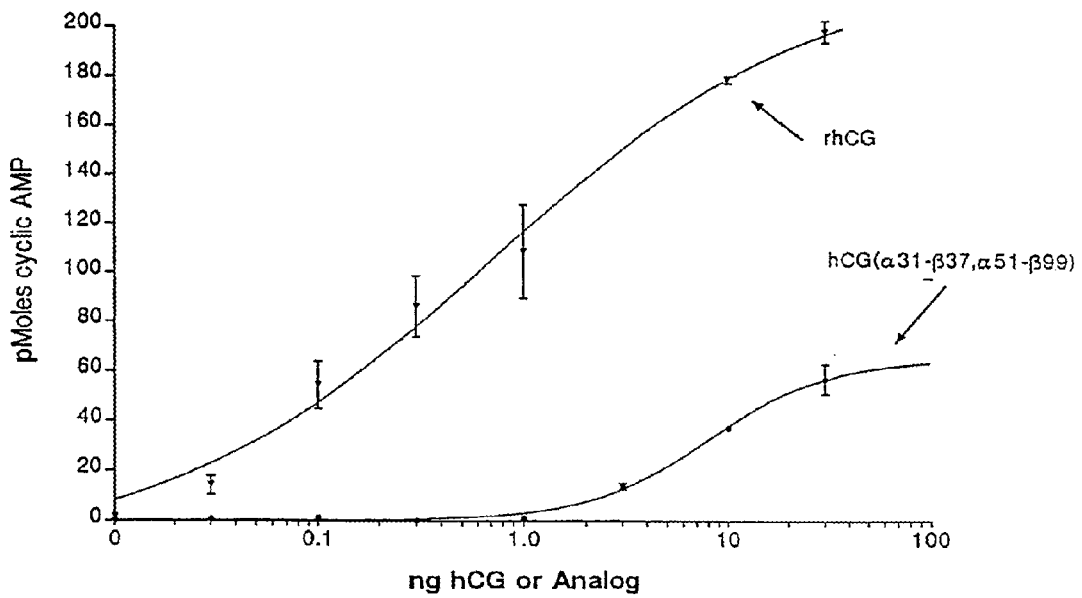
FIG. 30 illustrates the abilities of hCG, represented as a solid line with open symbols, and hCG(α31-β37, α51-β99), represented as a broken line with closed symbols, to inhibit the binding of $^{125}$I-hCG to CHO cells expressing LH receptors.
FIGS. 31A and 31B show the amino acid sequences of αC7S,K51C (FIG. 29A) (SEQ 10 NO:12) and hcGβ'Y37C, D99C (FIG. 29B) (SEQ 10 NO:13) in lower case letters representing the single letter amino acid code. The serine in FIG. 29A, which replaces Cys7, and the cysteines in FIG. 29B, which replace Tyr37 and Asp99, are shown in upper case.

The presence of two disulfide bonds in hCG(α31-β37,α51-β99) increased its stability relative to hCG in thermal denaturation assays (FIG. 8). In addition, hCG(α31-β37,α51-β99) was more stable than hCG to urea denaturation (FIG. 9). This suggested that the presence of more than one disulfide bond did not destabilize the molecule.

hCG(α31-β37,α51-β99) was able to bind to LH receptors and to stimulate cyclic AMP accumulation (FIGS. 29 and 30). Its activities in these assays were similar to that of hCG(α51-β99), again showing that the intersubunit disulfide between α-subunit residue 31 and β-subunit residue 37 had little, if any, detrimental influence on receptor binding or signal transduction. Thus, α31-β37 intercysteine knot site would be preferred for engineering a disulfide bond to stabilize glycoprotein hormones when retention of endocrine activity is desired.

Example 6

An Analog of hFSH Stabilized by an Intercysteine Knot Disulfide Between its α- and β-Subunits The discovery that hCG and CFC101-114 could be stabilized by an intersubunit disulfide between their cysteine knots without disrupting their LH and/or FSH activities strongly suggests that this region is not required for hormonal activity. Thus, it is expected that the engineering of a similar disulfide into FSH would result in an hFSH analog having increased stability and potent FSH activity. This analog would also be expected to bind antibodies that recognize hCG and hFSH α-subunits such as A113. It would also be expected to bind antibodies that recognize a region of hFSH β-subunit loops 1 and/or 3 distant from the site of the mutation such as B602.

The sequence of one α-subunit analog needed to prepare an hFSH analog crosslinked between α-subunit residue 31 and β-subunit residue 31 has been described in FIG. 3. The amino acid sequence of a less polar α-subunit that should also be useful for preparing this analog (αC7A) is illustrated in FIG. 32. The amino acid sequence of hFSH βY31C expected to form an intercysteine knot disulfide with αC7A or αC7S is also shown in FIG. 32. Nucleic acid sequences needed to prepare vectors that encode these proteins could be prepared from the human α-subunit and the hFSH β-subunit cDNAs by one skilled in the art of cloning using the genetic code illustrated in FIG. 33. These sequences could also be purchased from one of the suppliers listed in Example 1.

Vectors capable of driving the expression of αC7S and hFSHβY31C or αC7A and hFSHβY31C transiently or stably would be introduced into COS-7 or other eukaryotic cells by any means well known in the art such as that referenced in Example 1. Protein produced would be measured in a sandwich immunoassay using hFSH as a standard and capture antibodies that recognized epitopes of hFSH distant from the α-subunit N-terminus and detection antibodies that recognized epitopes of hFSH at sites in β-subunit loops 1 and/or 3.

The crosslinked analog of hFSH would be expected to be more stable than hFSH in thermal or urea denaturation assays as performed for crosslinked hCG analogs in Example 1. The crosslinked FSH analog would also be expected to compete with radioiodinated hFSH for binding to CHO cells that had been transfected with human FSH receptors. It would also be expected to stimulate cyclic AMP accumulation in these cells. In vitro assays can successfully predict the biological activities of fully glycosylated glycoprotein hormone analogs in vivo. Since the mutations that would be introduced to crosslink the glycoprotein hormone analogs are not expected to alter their overall glycosylation patterns relative to recombinant glycoprotein hormones, the crosslinked FSH analog would also be expected to be active in vivo.

Example 7

An Analog of hCG Stabilized by a Disulfide Between the N-Terminal Portions of the α- and β-Subunits Examples 1-4 teach that a single intersubunit disulfide bond between the subunits of glycoprotein hormones and their analogs can enhance their stability. These examples also show that the effect of the disulfide bond on the receptor binding and signal transduction activities of the molecule will be small, provided it does not involve residues that are important for receptor binding, receptor binding specificity, or contort the protein into an inappropriate conformation. The N-terminal portions of both the α- and β-subunits can be changed substantially without destroying hormonal activity, an indication that this part of the protein does not participate in key receptor contacts. Therefore, it is anticipated that introduction of a disulfide bond at the N-termini of the glycoprotein hormones at sites that are shown to be favorable in Table 1B will stabilize them without seriously disrupting their biological activities.

Table 1B shows that α-subunit Gln5 and hCG β-subunit Arg8 are favorably positioned such that replacing each with cysteine residues would lead to formation of a disulfide crosslinked analog. This analog would be expected to have enhanced stability relative to hCG and to retain the ability to bind and stimulate LH receptors.

The amino acid sequences needed to prepare vectors that would be useful for expressing this analog are illustrated in FIGS. 34A and 34B.

Example 8

An Analog of hFSH Stabilized by a Disulfide Between the N-Terminal Portions of the α- and β-Subunits As noted earlier, Examples 1-4 teach that an intersubunit disulfide bond between the subunits of glycoprotein hormones and their analogs can enhance their stability. These examples also show that the effect of the disulfide bond on receptor binding and signal transduction, provided it does not involve residues that are important for receptor binding or receptor binding specificity. Therefore, according to the present invention, it is expected that introduction of a disulfide bond at the N-termini of the hFSH will stabilize it and lead to an analog that will have useful therapeutic properties.

Based on data in Table 1B showing the favorable positions of α-subunit Gln5 and hCG β-subunit Arg8 and data in Table 2 showing "equivalent" residues in hCG and hFSH, replacing α-subunit Gln5 and hFSH β-subunit Ser2 with cysteine residues would be expected to create disulfide crosslinked hFSH analogs. These analogs would be expected to have enhanced stability relative to hFSH and would retain the ability to bind and stimulate FSH receptors. The amino acid sequences needed to prepare a vector that would be useful for expressing this analog are illustrated in FIG. 35.

Example 9

An Analog of hLH Stabilized by an Intercysteine Knot Disulfide Between the α- and β-Subunits or an Intersubunit Disulfide Between the N-Terminal Portions of the α and β-subunits The most closely related human lutropins are hCG and hLH. Thus, it would be expected that mutations needed to prepare active disulfide crosslinked hCG analogs would also be useful for preparation of active disulfide crosslinked hLH analogs. hLH is the least stable of the gonadotropins and it is also expected that the intersubunit disulfides will significantly increase the stability of hLH. The amino acid sequences of the β-subunit needed to prepare intercysteine knot disulfide crosslinked hLH and hLH that is crosslinked near its N-terminus are illustrated in FIGS. 36 and 37, respectively.

Example 10 hTSHβY30C, a β-Subunit Analog Expected to be Useful for Preparing hTSH Analogs Stabilized by an Intercysteine Knot Disulfide Between the α- and β-Subunits or an Intersubunit Between the N-Terminal Portions of the α- and β-subunits As noted earlier, Examples 1-4 teach that an intersubunit disulfide bond between the subunits of glycoprotein hormones and their analogs can enhance their stability. These examples also show that the effect of the disulfide bond on receptor binding and signal transduction, provided it does not involve residues that are important for receptor binding or receptor binding specificity. Therefore, it is anticipated that introduction of a disulfide bond between residues in the cysteine knots of the hTSH α- and β-subunits or in the N-termini of hTSH α- and β-subunits will stabilize the heterodimer leading to an analog that will have useful therapeutic properties such as stimulating the thyroid gland prior to radioiodine ablation therapy.

Based on data in Table 1B showing the favorable positions of α-subunit Cys31 and hCG β-subunit Tyr37 and data in FIG. 47 showing "equivalent" residues in hCG and hTSH, cells expressing αC7S or αC7A and a hTSH β-subunit analog in which Tyr30 is replaced by cysteine residue would be expected to create disulfide crosslinked hTSH analogs. Similarly, based on data in Table 1B showing the favorable positions of α-subunit Gln5 and hCG β-subunit Arg8 and data in FIG. 47 showing "equivalent" residues in hCG and hTSH, replacing α-subunit Gln5 and hTSH β-subunit Phe1 with cysteine residues would be expected to create disulfide crosslinked hTSH analogs. These analogs would be expected to have enhanced stability relative to hTSH and would retain the ability to bind and stimulate TSH receptors.

The amino acid sequences needed to prepare a vector that would be useful for expressing these analogs are illustrated in FIGS. 38 and 39.

Example 11

Preparation of Disulfide Crosslinked Hormone Antagonists

It is well-known that deglycosylation of the glycoprotein hormones reduces their abilities to elicit a biological signal (Moyle et al, 1975; Matzuk et al, 1989). However, due to their instability, the deglycosylated hormones are not therapeutically useful. It is expected that introduction of a disulfide crosslink into genetically deglycosylated hormones will increase their utility as hormone antagonists. An antagonist of LH or hCG would have both profertility and antifertility uses. Thus, when administered to women who are infertile because they have inappropriately high LH levels, an LH antagonist would potentiate fertility. When administered to women who were in the early stages of pregnancy, an hCG antagonist would terminate pregnancy. An antagonist of a bifunctional LH/FSH molecule such as CFC101-114 or CF101-109 (Moyle et al, 1994) would also be useful. Transient use of such an antagonist could be used to terminate inappropriate ovarian function, thereby causing the resetting the menstrual cycle. This would have a potential profertility effect. Use of such an antagonist during early pregnancy would be expected to suppress the production of both progesterone and estradiol and terminate pregnancy.

Besides introducing an intersubunit disulfide crosslink, the preparation of the crosslinked antagonists would involve changing the N-linked glycosylation signals on the α-subunit or on the α- and the β-subunits of the analogs that have been described or that could be produced by reference to Table 1B. This would involve changing the sequence Asn-X-Ser/Thr found in the α- and β-subunits of the glycoprotein hormones to either replace the Asn with another amino acid, change the Ser or Thr to another amino acid, or change the amino acid between Asn or Ser/Thr (represented as an X) to proline.

Example 12

Other disulfide crosslinked analogs of the gonadotropins that are expected to be more stable than the parental hormones are presented in Tables 6-12. These would be prepared by co-transfecting cells with vectors that can express the α-subunit and β-subunit constructs as indicated in Examples 1-5.

TABLE 6

Additional Analogs of the Human α-subunit that Can Be Used to Prepare Disulfide Crosslinked Analogs of hCG, hLH, hFSH, and hTSH αC31A   SEQ ID NO: 93
mdyyrkyaaiflvtlsvflhvlhsapdvqdcpectlqenpffsqpgapilqcmgAcfsrayptplrskktmlvqk
nvtsestccvaksynrvtvmggfkvenhtachcstcyyhks αQ27C   SEQ ID NO: 94
mdyyrkyaaiflvtlsvflhvlhsapdvqdcpectlqenpffsqpgapilCcmgccfsrayptplrskktmlvqk
nvtsestccvaksynrvtvmggfkvenhtachcstcyyhks αM29C   SEQ ID NO: 95
mdyyrkyaaiflvtlsvflhvlhsapdvqdcpectlqenpffsqpgapilqcCgccfsrayptplrskktmlvqk
nvtsestccvaksynrvtvmggfkvenhtachcstcyyhks αS34C   SEQ ID NO: 96
mdyyrkyaaiflvtlsvflhvlhsapdvqdcpectlqenpffsqpgapilqcmgccfCrayptplrskktmlvqk
nvtsestccvaksynrvtvmggfkvenhtachcstcyyhks αR35C   SEQ ID NO: 97
mdyyrkyaaiflvtlsvflhvlhsapdvqdcpectlqenpffsqpgapilqcmgccfsCayptplrskktmlvqk
nvtsestccvaksynrvtvmggfkvenhtachcstcyyhks

TABLE 6-continued

Additional Analogs of the Human α-subunit that Can Be Used to Prepare
Disulfide Crosslinked Analogs of hCG, hLH, hFSH, and hTSH αY37C  SEQ ID NO: 98
mdyyrkyaaiflvtlsvflhvlhsapdvqdcpectlqenpffsqpgapilqcmgccfsraCptplrskktmlvqk
nvtsestccvaksynrvtvmggfkvenhtachcstcyyhks αS55C  SEQ ID NO: 99
mdyyrkyaaiflvtlsvflhvlhsapdvqdcpectlqenpffsqpgapilqcmgccfsrayptplrskktmlvqk
nvtCestccvaksynrvtvmggfkvenhtachcstcyyhks αS57C  SEQ ID NO: 100
mdyyrkyaaiflvtlsvflhvlhsapdvqdcpectlqenpffsqpgapilqcmgccfsrayptplrskktmlvqk
nvtseCtccvaksynrvtvmggfkvenhtachcstcyyhks αC87A  SEQ ID NO: 101
mdyyrkyaaiflvtlsvflhvlhsapdvqdcpectlqenpffsqpgapilqcmgccfsrayptplrskktmlvqk
nvtsestccvaksynrvtvmggfkvenhtachcstAyyhks αV61C  SEQ ID NO: 102
mdyyrkyaaiflvtlsvflhvlhsapdvqdcpectlqenpffsqpgapilqcmgccfsrayptplrskktmlvqk
nvtsestccCaksynrvtvmggfkvenhtachcstcyyhks αK75C  SEQ ID NO: 103
mdyyrkyaaiflvtlsvflhvlhsapdvqdcpectlqenpffsqpgapilqcmgccfsrayptplrskktmlvqk
nvtsestccvaksynrvtvmggfCvenhtachcstcyyhks αV76C  SEQ ID NO: 104
mdyyrkyaaiflvtlsvflhvlhsapdvqdcpectlqenpffsqpgapilqcmgccfsrayptplrskktmlvqk
nvtsestccvaksynrvtvmggfkCenhtachcstcyyhks αC59A  SEQ ID NO: 105
mdyyrkyaaiflvtlsvflhvlhsapdvqdcpectlqenpffsqpgapilqcmgccfsrayptplrskktmlvqk
nvtsestAcvaksynrvtvmggfkvenhtachcstcyyhks (Note: mutation is in upper case)

TABLE 7

Additional Analogs of the hFSH β-subunit Useful for Preparing Disulfide
crosslinked Analogs of hFSH when Combined with the Appropriate α-subunit Analogs hFSHβR35C  SEQ ID NO: 106
mktlqffflfccwkaiccnsceltnitiavekegcgfcitinttwcagycytCdlvykdparpkiqktctfkelv
yetvrvpgcahhadslytypvatqchcgkcdsdstdctvrglgpsycsfgemke hFSHβA29C  SEQ ID NO: 107
mktlqffflfccwkaiccnsceltnitiavekegcgfcitinttwcCgycytrdlvykdparpkiqktctfkelv
yetvrvpgcahhadslytypvatqchcgkcdsdstdctvrglgpsycsfgemke hFSHβW27C  SEQ ID NO: 108
mktlqffflfccwkaiccnsceltnitiavekegcgfcitinttCcagycytrdlvykdparpkiqktctfkelv
yetvrvpgcahhadslytypvatqchcgkcdsdstdctvrglgpsycsfgemke hFSHβT92C  SEQ ID NO: 109
mktlqffflfccwkaiccnsceltnitiavekegcgfcitinttwcagycytrdlvykdparpkiqktctfkelv
yetvrvpgcahhadslytypvatqchcgkcdsdsCdctvrglgpsycsfgemke hFSHβT50C  SEQ ID NO: 110
mktlqffflfccwkaiccnsceltnitiavekegcgfcitinttwcagycytrdlvykdparpkiqkCctfkelv
yetvrvpgcahhadslytypvatqchcgkcdsdstdctvrglgpsycsfgemke hFSHβT34C  SEQ ID NO: 111
mktlqffflfccwkaiccnsceltnitiavekegcgfcitinttwcagycyCrdlvykdparpkiqktctfkelv
yetvrvpgcahhadslytypvatqchcgkcdsdstdctvrglgpsycsfgemke hFSHβD36C  SEQ ID NO: 112
mktlqffflfccwkaiccnsceltnitiavekegcgfcitinttwcagycytrClvykdparpkiqktctfkelv
yetvrvpgcahhadslytypvatqchcgkcdsdstdctvrglgpsycsfgemke hFSHβK40C  SEQ ID NO: 113
mktlqffflfccwkaiccnsceltnitiavekegcgfcitinttwcagycytrdlvyCdparpkiqktctfkelv
yetvrvpgcahhadslytypvatqchcgkcdsdstdctvrglgpsycsfgemke TABLE 7-continued Additional Analogs of the hFSH β-subunit Useful for Preparing Disulfide crosslinked Analogs of hFSH when Combined with the Appropriate α-subunit Analogs hFSHβV38C  SEQ ID NO: 114
mktlqffflfccwkaiccnsceltnitiavekegcgfcitinttwcagycytrdlCykdparpkiqktctfkelv
yetvrvpgcahhadslytypvatqchcgkcdsdstdctvrglgpsycsfgemke hFSHβBQ48C  SEQ ID NO: 115
mktlqffflfccwkaiccnsceltnitiavekegcgfcitinttwcagycytrdlvykdparpkiCktctfkelv
yetvrvpgcahhadslytypvatqchcgkcdsdstdctvrglgpsycsfgemke (Note: mutation is in upper case)

TABLE 8

Additional Analogs of the hCG β-subunit Useful for Preparing Disulfide Crosslinked Analogs of hCG when Combined with the Appropriate α-subunit Analogs hCGβM41C  SEQ ID NO: 116
memfqglllllllsmggtwaskeplrprcrpinatlavekegcpvcitvntticagycptCtrvlqgvlpalpqv
vcnyrdvrfesirlpgcprgvnpvvsyavalscqcalcrrsttdcggpkdhpltcddprfqdsssskapppslps
psrlpgpsdtpilpq hCGβV56C  SEQ ID NO: 117
memfqglllllllsmggtwaskeplrprcrpinatlavekegcpvcitvntticagycptmtrvlqgvlpalpqv
Ccnyrdvrfesirlpgcprgvnpvvsyavalscqcalcrrsttdcggpkdhpltcddprfqdsssskapppslps
psrlpgpsdtpilpq hCGβA35C  SEQ ID NO: 118
memfqglllllllsmggtwaskeplrprcrpinatlavekegcpvcitvntticCgycptmtrvlqgvlpalpqv
vcnyrdvrfesirlpgcprgvnpvvsyavalscqcalcrrsttdcggpkdhpltcddprfqdsssskapppslps
psrlpgpsdtpilpq hCGβI33C  SEQ ID NO: 119
memfqglllllllsmggtwaskeplrprcrpinatlavekegcpvcitvnttCcagycptmtrvlqgvlpalpqv
vcnyrdvrfesirlpgcprgvnpvvsyavalscqcalcrrsttdcggpkdhpltcddprfqdsssskapppslps
psrlpgpsdtpilpq hCGβT98C  SEQ ID NO: 120
memfqglllllllsmggtwaskeplrprcrpinatlavekegcpvcitvntticagycptmtrvlqgvlpalpqv
vcnyrdvrfesirlpgcprgvnpvvsyavalscqcalcrrstCdcggpkdhpltcddprfqdsssskapppslps
psrlpgpsdtpilpq hCGβT40C  SEQ ID NO: 121
memfqglllllllsmggtwaskeplrprcrpinatlavekegcpvcitvntticagycpCmtrvlqgvlpalpqv
vcnyrdvrfesirlpgcprgvnpvvsyavalscqcalcrrsttdcggpkdhpltcddprfqdsssskapppslps
psrlpgpsdtpilpq hCGβT42C  SEQ ID NO: 122
memfqglllllllsmggtwaskeplrprcrpinatlavekegcpvcitvntticagycptmCrvlqgvlpalpqv
vcnyrdvrfesirlpgcprgvnpvvsyavalscqcalcrrsttdcggpkdhpltcddprfqdsssskapppslps
psrlpgpsdtpilpq hCGβQ46C  SEQ ID NO: 123
memfqglllllllsmggtwaskeplrprcrpinatlavekegcpvcitvntticagycptmtrvlCgvlpalpqv
vcnyrdvrfesirlpgcprgvnpvvsyavalscqcalcrrsttdcggpkdhpltcddprfqdsssskapppslps
psrlpgpsdtpilpq hCGβV44C  SEQ ID NO: 124
memfqglllllllsmggtwaskeplrprcrpinatlavekegcpvcitvntticagycptmtrClqgvlpalpqv
vcnyrdvrfesirlpgcprgvnpvvsyavalscqcalcrrsttdcggpkdhpltcddprfqdsssskapppslps
psrlpgpsdtpilpq hCGβQ54C  SEQ ID NO: 125
memfqglllllllsmggtwaskeplrprcrpinatlavekegcpvcitvntticagycptmtrvlqgvlpalpCv
vcnyrdvrfesirlpgcprgvnpvvsyavalscqcalcrrsttdcggpkdhpltcddprfqdsssskapppslps
psrlpgpsdtpilpq (Note: mutation is in upper case)

TABLE 9

Additional Analogs of the hLH β-subunit Useful for Preparing Disulfide Crosslinked Analogs of hLH when combined with the Appropriate α-subunit Analogs hLHβV44C  SEQ ID NO: 126
memlqglllllllsmggawasreplrpwchpinailavekegcpvcitvntticagycptmmrClqavlpplpqv
vctyrdvrfesirlpgcprgvdpvvsfpvalscrcgpcrrstsdcggpkdhpltcdhpqlsgllfl

TABLE 9-continued

Additional Analogs of the hLH β-subunit Useful for Preparing Disulfide
Crosslinked Analogs of hLH when combined with the Appropriate α-subunit Analogs

```
hLHβM41C                                                              SEQ ID NO: 127
memlqglllllllsmggawasreplrpwchpinailavekegcpvcitvntticagycptCmrvlqavlpplpqv
vctyrdvrfesirlpgcprgvdpvvsfpvalscrcgpcrrstsdcggpkdhpltcdhpqlsgllfl hLHβV56C                                                              SEQ ID NO: 128
memlqglllllllsmggawasreplrpwchpinailavekegcpvcitvntticagycptmmrvlqavlpplpqv
Cctyrdvrfesirlpgcprgvdpvvsfpvalscrcgpcrrstsdcggpkdhpltcdhpqlsgllfl hLHβA35C                                                              SEQ ID NO: 129
memlqglllllllsmggawasreplrpwchpinailavekegcpvcitvnttiCgycptmmrvlqavlpplpqv
vctyrdvrfesirlpgcprgvdpvvsfpvalscrcgpcrrstsdcggpkdhpltcdhpqlsgllfl hLHβI33C                                                              SEQ ID NO: 130
memlqglllllllsmggawasreplrpwchpinailavekegcpvcitvnttCcagycptmmrvlqavlpplpqv
vctyrdvrfesirlpgcprgvdpvvsfpvalscrcgpcrrstsdcggpkdhpltcdhpqlsgllfl hLHβS98C                                                              SEQ ID NO: 131
memlqglllllllsmggawasreplrpwchpinailavekegcpvcitvntticagycptmmrvlqavlpplpqv
vctyrdvrfesirlpgcprgvdpvvsfpvalscrcgpcrrstCdcggpkdhpltcdhpqlsgllfl hLHβT40C                                                              SEQ ID NO: 132
memlqglllllllsmggawasreplrpwchpinailavekegcpvcitvntticagycpCmmrvlqavlpplpqv
vctyrdvrfesirlpgcprgvdpvvsfpvalscrcgpcrrstsdcggpkdhpltcdhpqlsgllfl hLHβM42C                                                              SEQ ID NO: 133
memlqglllllllsmggawasreplrpwchpinailavekegcpvcitvntticagycptmCrvlqavlpplpqv
vctyrdvrfesirlpgcprgvdpvvsfpvalscrcgpcrrstsdcggpkdhpltcdhpqlsgllfl hLHβQ46C                                                              SEQ ID NO: 134
memlqglllllllsmggawasreplrpwchpinailavekegcpvcitvntticagycptmmrylCavlpplpqv
vctyrdvrfesirlpgcprgvdpvvsfpvalscrcgpcrrstsdcggpkdhpltcdhpqlsgllfl hLHβQ54C                                                              SEQ ID NO: 135
memlqglllllllsmggawasreplrpwchpinailavekegcpvcitvntticagycptmmrvlqavlpplpCv
vctyrdvrfesirlpgcprgvdpvvsfpvalscrcgpcrrstsdcggpkdhpltcdhpqlsgllfl
```

(Note: mutation is in upper case)

TABLE 10

Heterodimers of hFSH that Contain Intersubunit Disulfide Bonds that Increase its Stability

| α-subunit Construct | β-subunit Construct | Intersubunit Disulfide |
|---|---|---|
| αC31A | hFSHβY31C* | α7-β31 |
| αQ27C | hFSHβV38C* | α27-β38 |
| αM29C | hFSHβR35C | α29-β35 |
| αS34C | hFSHβT50C | α34-β50 |
| αR35C | hFSHβA29C | α35-β29 |
| αY37C | hFSHβW27C | α37-β27 |
| αS55C | hFSHβT92C | α55-β92 |
| αS57C | hFSHβT50C | α57-β50 |
| αC87A | hFSHβT34C | α59-β34 |
| αV61C | hFSHβD36C | α61-β36 |
| αK75C | hFSHβK40C | α75-β40 |
| αV76C | hFSHβV38C | α76-β38 |
| αC59A | hFSHβQ48C | α87-β48 |

Note:
Those expected to retain substantial biological activity are indicated by an asterisk. This is calculated based on the role of the residues that involved in receptor binding or receptor binding specificity as shown in Examples 1-4. The cross-linked heterodimers would be prepared by co-transfection of the indicated α- and β-subunit analog cDNA into mammalian cells using the methods described in Example 1.

TABLE 11

Heterodimers of hCG that Contain Intersubunit Disulfide Bonds that Increase its Stability

| α-subunit Construct | β-subunit Construct | Intersubunit Disulfide |
|---|---|---|
| αC31A | hCGβY37C* | α7-β37 |
| αC31A | hCGβR6C* | α7-β6 |
| αQ27C | hCGβV44C* | α27-β44 |
| αM29C | hCGβM41C | α29-β41 |
| αS34C | hCGβV56C | α34-β56 |
| αR35C | hCGβA35C | α35-β35 |
| αY37C | hCGβI33C | α37-β33 |
| αS55C | hCGβT98C | α55-β98 |
| αS57C | hCGβV56C | α57-β56 |
| αC87A | hCGβT40C | α59-β40 |
| αV61C | hCGβT42C | α61-β42 |
| αK75C | hCGβQ46C | α75-β46 |
| αV76C | hCGβV44C | α76-β44 |
| αC59A | hCGβQ54C | α87-β54 |

Note:
Those expected to retain substantial biological activity are indicated by an asterisk. This is calculated based on the role of the residues that involved in receptor binding or receptor binding specificity as shown in Examples 1-4. The cross-linked heterodimers would be prepared by co-transfection of the indicated α- and β-subunit analog cDNA into mammalian cells using the methods described in Example 1.

TABLE 12

Heterodimers of hLH that Contain Intersubunit Disulfide Bonds that Increase its Stability

| α-subunit Construct | β-subunit Construct | Intersubunit Disulfide |
|---|---|---|
| αC31A | hLHβY37C* | α7-β37 |
| αC31A | hLHβR6C* | α7-β6 |
| αQ27C | hLHβV44C* | α27-β44 |
| αM29C | hLHβM41C | α29-β41 |
| αS34C | hLHβV56C | α34-β56 |

TABLE 12-continued

Heterodimers of hLH that Contain Intersubunit
Disulfide Bonds that Increase its Stability

| α-subunit Construct | β-subunit Construct | Intersubunit Disulfide |
|---|---|---|
| αR35C | hLHβA35C | α35-β35 |
| αY37C | hLHβI33C | α37-β33 |
| αS55C | hLHβT98C | α55-β98 |
| αS57C | hLHβV56C | α57-β56 |
| αC87A | hLHβT40C | α59-β40 |
| αV61C | hLHβT42C | α61-β42 |
| αK75C | hLHβQ46C | α75-β46 |
| αV76C | hLHβV44C | α76-β44 |
| αC59A | hLHβQ54C | α87-β54 |

Note:
Those expected to retain substantial biological activity are indicated by an asterisk. This is calculated based on the role of the residues that involved in receptor binding or receptor binding specificity as shown in Examples 1-4. The cross-linked heterodimers would be prepared by co-transfection of the indicated α- and β-subunit analog cDNA into mammalian cells using the methods described in Example 1.

Example 13

An hCG Analog Containing a Disulfide Between β-Subunit Loop 2 and α-Subunit Loop 3

The residues that create this disulfide are in a region of hCG proposed not to participate in the high affinity receptor contacts (Moyle et al, 1995). Neither the second β-subunit loop nor the third β-subunit loop of hCG are needed for lutropin activity and active analogs of hCG can be made in which both have been deleted (Moyle et al, 1998). In addition, analogs of hCG that have full activity have been prepared in which β-subunit loop 2 has been replaced with its hFSH counterpart (Campbell et al, 1991). Thus, addition of an intrasubunit disulfide between these portions of the protein would not be expected by the present inventor to disrupt its biological activity. This analog would be prepared by modifying vectors that encoded the α- and β-subunits of hCG and co-expressing them in mammalian cells. The α-subunit construct encoded a protein having the amino acid sequence termed αV76C as shown in Table 6. This construct was prepared by PCR mutagenesis using oligonucleotides 1131 and 1132 as primers (Table 2) and pMB589 as a template. Plasmid pMB589 is a construct in pCI' that encodes an analog of the human α-subunit in which the codon for Asn52 was changed to aspartic acid and in which the codons for Arg42 and Ser43 were modified to create a silent BglII site.

pMB589 was made by subcloning the XhoI-BamHI insert from pMB532 into the pCI' vector between the XhoI-BamHI sites, and pBM532 was made from pMB507, a construct described previously, by PCR using oligonucleotides 850 and 851 as primers (Table 2) and pMB507 as template. The PCR product was digested with BglII and SpeI and subcloned into the BglII and SpeI sites of pMB507 and sequenced to give pMB532.

The PCR product was digested with BglII and PstI and the insert was cloned into the BglII and PstI sites of pMB507 to create pMB910. Positive clones were identified by the presence of an extra DraI site that had been introduced into the construct. After the DNA sequence of pMB910 was confirmed by the dideoxy method, the DNA fragment that encoded the entire α-subunit analog was removed from pMB910 by XhoI and BamHI digestion and subcloned into the XhoI and BamHI sites of the pCI' vector to create pMB926. pMB926 encodes αV76C.

To create the hCG β-subunit partner for αV76C, a vector that encoded hCGβ'V44C was prepared. This is an analog of hCG β-subunit expected to form a disulfide crosslinked heterodimer with αV76C when expressed in the same cells as pMB926. Oligonucleotides 1133 and 1134 (Table 2) were synthesized and ligated into the NgoMI-PstI site of pKMB-β' to create pMB909. The XhoI-BamHI fragment from pMB909 was transferred into pCI' to create pMB941. The hCGβV44C amino acid sequence encoded by pMB941 is shown in Table 8.

Example 14

An hFSH Analog Containing a Disulfide Between β-Subunit Loop 2 and α-Subunit Loop 3

Based on the similarity of the amino acid sequences of hCG and hFSH β-subunits, notably the cysteines (Table 4), both proteins would be expected to have similar architectures. The relative positions of Val44 in the hCG β-subunit loop 2 and Val76 in the α-subunit loop 3 suggested that changing these residues to cysteines would create an intersubunit disulfide between β-subunit loop 2 and α-subunit loop 3. Val38 occupies a similar position in the hFSH β-subunit as Val 44 of the hCG β-subunit. Therefore, changing hFSHβVal38 to cysteine and expressing the resulting construct with αV76C was thought to result in a disulfide crosslinked heterodimer. To change Val38 in the hFSH β-subunit to cysteine, the present inventor started with pMB603, a construct that contains the hFSHβ cDNA coding sequence minus the untranslated 3' and 5' ends in the pCI' vector between the XhoI and BamHI restriction sites. The small DNA fragment between the BstXI and PpuMI sites of pMB603 was replaced with an oligonucleotide cassette prepared by annealing oligonucleotides 1154 and 1155 (Table 2).

Figure 45:
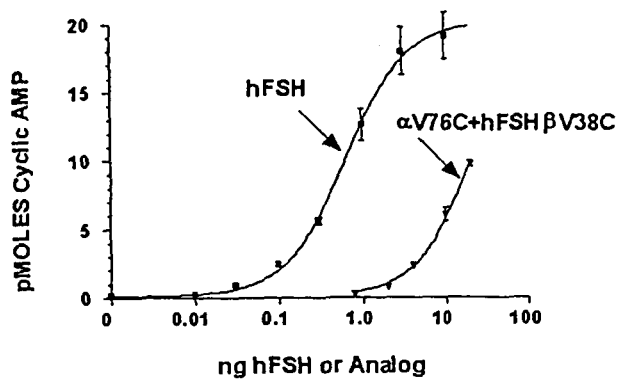
FIG. 45 shows the abilities of hFSH and the analog, αV76C+hFSHβV38C, to stimulate cyclic-AMP accumulation in CHO cells expressing the human FSH receptor.

The resulting construct, termed pMB920, was screened for the lack of a BstXI site and the presence of a PpuMI site. After DNA sequencing confirmed the presence of the desired change, pMB920 was co-transfected into COS-7 cells with pMB926, the vector that drives expression of αV76C. The cells secreted a heterodimer into the medium that was readily detected in a sandwich immunoassay using anti-α-subunit monoclonal antibody A113 for capture and radiolabeled anti-hFSHβ-subunit monoclonal antibody B602. The hFSHβ38C amino acid sequence encoded by pMB920 is shown in Table 7. The heterodimer composed of αV76C and hFSHβV38C stimulated cyclic AMP accumulation in CHO cells expressing the human FSH receptor (FIG. 45).

Example 15

Figure 46:
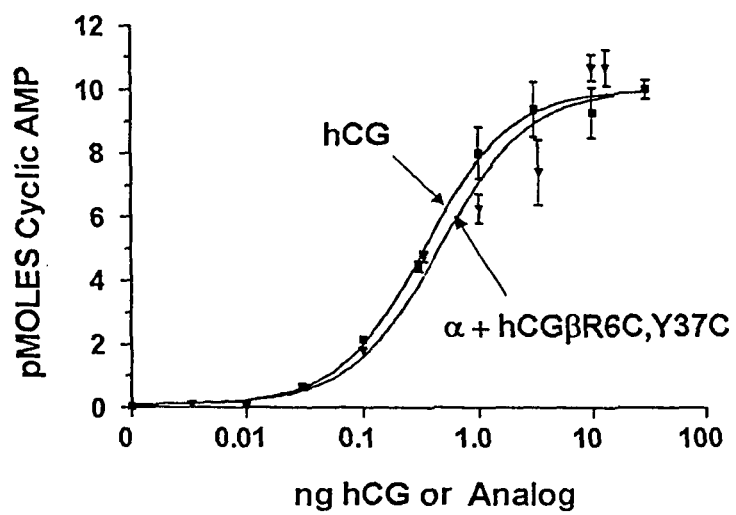
FIG. 46 shows the abilities of hCG and the analog, α+hCGβR6C,Y37C, to stimulate cyclic-AMP accumulation in CHO cells expressing LH receptors.

An hCG Analog Containing a Disulfide Between the N-Termini of Each Subunit and Between the Cysteine Knots The preceding disulfide crosslinked heterodimers were prepared by modifying each subunit to create a free thiol that could participate in an intersubunit disulfide. It is shown here that it is possible to prepare a disulfide crosslinked hCG analog by modifying only the β-subunit of hCG. The crystal structure of hCG showed that α-subunit Cys31 was located near β-subunit Tyr 37, and the sidechains of both subunits were pointed towards one another. This observation was used previously to insert an intersubunit disulfide bond between hCG α-subunit residue 31 and β-subunit residue 37. The crystal structure of hCG also shows that α-subunit residue Cys7 is located near hCG β-subunit residue Arg6. In fact, α-subunit residues Cys7 and Cys31 are positioned near β-subunit residues Arg6 and Tyr37 such that converting Arg6 and Tyr37 might promote the formation of a heterodimer containing αCys7-αCys31 and βCys6-βCys37 intrasubunit disulfides, a heterodimer containing αCys7-βCys6 and αCys31-βCys37 intersubunit disulfides, or a heterodimer containing αCys7-βCys37 and αCys31-βCys6 intersubunit disulfides. Computer simulations showed that each of these disulfide bonds could be formed without undue strain on the protein. The formation of multiple disulfides should be useful to create a group of isomers or isoforms that have different half-lives. These might have novel therapeutic uses, particularly when a biological response needs to be "jump-started". In using these, one would administer a large bolus of analog to initiate a hormonal response. The fraction of the heterodimer that was not crosslinked would be expected to be cleared faster than that of the crosslinked heterodimer. Consequently, the large initial injection would be sufficient to start the response, but its activity would dissipate to a lower level that would be sustained for a longer time to maintain the response. This analog would also be expected to serve as an intermediate for the preparation of PEGylated analogs. Cysteine residues have unique reactivities, and it is often desirable to add a free cysteine to a protein surface. However, due to the reactivity of cysteine, this type of protein can be difficult to create. It is known that the α-subunit Cys7-Cys31 disulfide is readily reduced to a state that would create a free cysteine. Introduction of a cysteine in the β-subunit between residues 6 and 37 would be expected to create a similar type of disulfide. It is expected that the cysteines in these disulfides would be more active than others in the protein, particularly since they are in a location that would facilitate disulfide exchange. Thus, the present inventor would expect that it would be possible to react the existing α-subunit cysteine at residue Cys7 and an added cysteine at β-subunit residue Cys6 with agents that would modify the protein. These could include those capable of PEGylating the protein and stabilizing its biological half-life. The cysteines that are "freed" in this process would be able to form an intersubunit disulfide that would stabilize the protein. Preparation of this analog required adding a second cysteine to the analog known as hCGβ'Y37C.

pMB940, a construct encoding analog hCGβ' was prepared by PCR mutagenesis using oligonucleotides 1161 and 1163 (Table 2) as primers and pCI'-hCGβ' as template. Oligonucleotide 1161 primes off sequences that are located in the pCI' vector and oligonucleotide 1163 encodes the mutation. The PCR product was digested with XhoI and BanI and ligated with the BanI-BamHI fragment obtained from pSVL-hCGβ'Y37C into the large XhoI-BamHI fragment of pCI' to create pMB941. The DNA sequence of the coding sequence of pMB941 was confirmed by the dideoxy method. pMB941 encodes the amino acid sequence shown below:

hCGβ'R6C,Y37C:
(SEQ ID NO: 136)
memfqglllllllsmggtwaskeplCprcrpinatlavekegcpvcitvn tticagCcptmtrvlqgvlpalpqvvcnyrdvrfesirlpgcprgvnpvv syavalscqcalcrrsttdcggpkdhpltcddprfqdssssk pMB940 and pSV2Neo were co-transfected into CHO cells and a stable line was selected by its resistance to the toxic drug G418. The protein harvested from the medium was quantified using a sandwich immunoassay employing anti-α-subunit antibody A113 for capture and radioiodinated anti-β-subunit antibody B112 for detection. This assay confirmed the presence of heterodimer in the culture medium. The biological activity of the heterodimer was measured in a cyclic AMP accumulation assay using CHO cells that express the rat LH receptor. The results of this assay are illustrated in FIG. 46.

Example 16

An hFSH Analog Containing a Disulfide Between the N-Termini of Each Subunit and Between the Cysteine Knots As noted earlier, formation of multiple disulfides might be useful to create a group of protein isoforms having different half-lives. A similar analog would offer an improved approach to stimulating follicle development. The fraction of the heterodimer containing no intersubunit disulfide and that was not crosslinked should be cleared faster than the fraction of heterodimer containing an intersubunit crosslink. Consequently, a large initial injection would be sufficient to stimulate initial follicle development, but its activity would dissipate to a lower level that would be sustained for a longer time. This would more closely mimic the type of FSH stimulation seen during the follicular phase and may reduce the chance of hyperstimulation. It would be expected that addition of a cysteine to the N-terminus of the hFSH β-subunit or that addition of the hCG β-subunit amino terminus to the N-terminus of the hFSH β-subunit would facilitate formation of the heterodimer and the intersubunit crosslink. An hFSH β-subunit analog expected to form a heterodimer similar to that of the analog in Example 15 would have the amino acid sequence shown below:

hFSH'βR-2C,Y31C:
(SEQ ID NO: 137)
memfqglllllllsmggtwaskeplCnsceltnitiavekegcgfcitin ttwcagCcytrdlvykdparpkiqktctfkelvyetvrvpgcahhadsly typvatqchcgkcdsdstdctvrglgpsycsfgemke Example 17

An hCG Analog Having Potent hFSH Activity Containing a Disulfide Arrangement Similar to the Analog in Example 15 hCG analogs in which β-subunit amino acids 94-110 are replaced with their hFSH counterparts have high FSH activity. Chimeras of hCG and hFSH containing hFSH β-subunit residues 95-103 in place of hCG β-subunit residues 101-109 and having cysteines at β-subunit residues 6 and 37 would be expected to form a similar disulfide arrangement as that in Example 15. These would also be expected to have high FSH activity. The amino acid sequence of the β-subunit of one such analog would be:

CFC94-117βR6C,Y37C:
(SEQ ID NO: 138)
memfqglllllllsmggtwaskeplCprcrpinatlavekegcpvcitvn tticagCcptmtrvlqgvlpalpqvvcnyrdvrfesirlpgcprgvnpvv syavalscqcalcdsdstdctvrglgpsycsfgemkesssskapppslps psrlpgpsdtpilpq

Having now fully described this invention, it will be appreciated by those skilled in the art that the same can be performed within a wide range of equivalent parameters, con- centrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adachi et al, *J. Biol. Chem.* 264:8537-41 (1989)
Alber et al, *Biochemistry* 26:3751-3758 (1987)
Ausubel et al, *Current Protocols in Molecular Biology*, Greene Publications and Wiley Interscience (New York, 1987-1997)
Baenziger et al, *Biochim. Biophys. Acta* 947:287-306 (1988)
Baenziger et al, *Proc. Natl. Acad. Sci., USA* 89:334-338 (1992)
Baird et al, *Oxf. Rev. Reprod. Biol.* 15:191-232 (1993)
Bedows et al, *J. Biol. Chem.* 268:11655-11662 (1993)
Berger et al, *Molecular and Cellular Endocrinology* 125:33-43 (1996)
Bernard et al, *Mol. Cell. Endocrinol.* 71:R19-R23 (1990)
Birken et al, *J. Biol. Chem.* 261:10719-10727 (1986)
Birken et al, *Endocrinology* 129:1551-1558 (1991)
Blithe et al, *Endocrinology* 129:2257-2259 (1991)
Blowmick et al, *Mol. Endocrinol.* 10:1147-1159 (1996)
Bo et al, *J. Biol. Chem.* 267:3179-3184 (1992)
Braun et al, *EMBO. J.* 10:1885-1890 (1991)
Braustein et al, *Endocrinology* 91:1030-1036 (1972)
Brooker et al, *Adv. Cyclic Nucl. Res.* 10:1-33 (1979)
Campbell et al, *Proc. Natl. Acad. Sci., USA* 88:760-764 (1991)
Campbell et al, *Mol. Cell. Endocrinol.* 83:195-200 (1992)
Campbell et al, *Nature Biotech.* 15:439-443 (1997)
Chen et al, *J. Biol. Chem.* 266:19357-19361 (1991)
Cole et al, *Cancer. Res.* 41:1615-1619 (1981)
Cole et al, *Endocrinology* 129:1559-1567 (1991)
Cole et al, *J. Biol. Med.* 64:627-637 (1991)
Cole et al, *J. Clin. Endocrinol. Metab.* 76:704-710 (1993)
Cosowsky et al, *J. Biol. Chem.* 270:20011-20019 (1995)
Cosowsky et al, *J. Biol. Chem.* 272:3309-3314 (1997)
DeBeer et al, *Eur. J. Biochem.* 241:229-242 (1996)
Fiddes et al, in *Recent Progress in Hormone Research*, Vol 40; R. O. Greep, ed., Academic Press, New York (1984), pp. 43-78.
Fiete et al, *Cell* 67:1103-1110 (1991)
Forastieri et al, *J. Biol. Chem.* 257:7976-7981 (1982)
Furuhashi et al, *J. Biol. Chem.* 269:25543-25548 (1994)
Galway et al, *Endocrinology* 127:3023-3028 (1990)
Gast, M. J., *Am. J. Obstet. Gynecol.* 172:753-759 (1995)
Gennaro, A., Ed., *Remington's Pharmaceutical Sciences*, 18th Ed., Mack Publishing Co. (Easton, Pa., 1990)
Han et al, *Mol. Cell. Endocrinol.* 124:151-161 (1996)
Ho et al, *Gene* 77:51-59 (1989)
Huang et al, *J. Biol. Chem.* 268:9311-9315 (1993)
Imai et al, *Bioconjug. Chem.* 1:144-148 (1990)
Ji et al, *Endocrinology* 128:2648-2650 (1991)
Jia et al, *Mol. Endocrinol.* 5:759-768 (1991)
Jiang et al, *Structure* 3:1341-1353 (1995)
Kardana et al, *Endocrinology* 129:1541-1550 (1991)
Kobe et al, *Nature* 366:751-756 (1993)
Kobe et al, *Nature* 374:183-186 (1995)
Kriegler, M., *Gene Transfer and Expression: A Laboratory Manual*, Stockton Press, New York (1990)
Lapthorn et al, *Nature* 369:455-461 (1994)
Lim et al, *Nature* 339:31-36 (1989)
Lim et al, *Biochemistry* 31:4324-4333 (1992)
Loosfelt et al, *Science* 245:525-528 (1989)
Maniatis et al, *Molecular Cloning: A Laboratory Manual*, Cold Spring Harbor Laboratory, Cold Spring Harbor, N.Y. (1989)
Matsumura et al, *Nature* 342:291-293 (1989)
Matthews, B. W., *Biochemistry* 26:6885-6888 (1987)
Matzuk et al, *J. Biol. Chem.* 264:2409-2414 (1989)
McFarland et al, *Science* 245:494-499 (1989)
McIntosh et al, *J. Biomolecular Structure and Dynamics* 5:21-33 (1987)
Mise et al, *J. Biol. Chem.* 255:8516-8522 (1980)
Mise et al, *J. Biol. Chem.* 256:6587-6592 (1981)
Moudgal et al, *J. Clin. Endocrinol. Metab.* 32:579-581 (1971)
Moudgal et al, *J. Clin. Endocrinol. Metab.* 35:113-116 (1972)
Moudgal, N. R., in *Immunization with Hormones in Reproduction Research*, E. Nieschlag, ed., North-Holland, Amsterdam (1976), p. 233
Moudgal et al, *Fertility & Sterility* 30:223-229 (1978)
Moyle et al, *J. Biol. Chem.* 250:9163-9169 (1975)
Moyle et al, *Proc. Natl. Acad. Sci., USA* 79:2245-2249 (1982)
Moyle et al, *J. Biol. Chem.* 265:8511-8518 (1990)
Moyle et al, *J. Biol. Chem.* 266:10807-10812 (1991)
Moyle et al, *Nature* 368:251-255 (1994)
Moyle et al, *Endocrinology*, L. J. DeGroot, ed., Saunders, Philadelphia (1995), pp. 230-241.
Moyle et al, *J. Biol. Chem.* 270:20020-20031 (1995)
Moyle et al, *Chemistry & Biology* 5:241-254 (1998)
Murphy et al, *Endocr. Rev.* 12:27-44 (1991)
Nagayama et al, *Biochem. Biophys. Res. Commun.* 165:1184-1190 (1989)

Nagayama et al, *Proc. Natl. Acad. Sci., USA* 88:902-905 (1991)
Pal et al, *Am. J. Reprod. Immunol.* 22:124-126 (1990)
Okayama, *Mol. Cel. Biol.* 3:280 (1983)
Olive, D. L., *Am. J. Obstet. Gynecol.* 172:759-765 (1995)
Overington et al, *Protein Science* 1:216-226 (1992)
Pierce et al, *Ann. Rev. Biochem.* 50:465-495 (1981)
Ravindranath et al, *J. Reprod. Fertil.* 88:25-30 (1990)
Reddy et al, *Proc. Natl. Acad. Sci., USA* 82:3644-3648 (1985)
Remy et al, *Molecular and Cellular Endocrinology* 125:79-91 (1996)
Rosa et al, *J. Clin. Endocrinol. Metab.* 59:1215-1219 (1984)
Segaloff et al, *Recent. Prog. Horm. Res.* 46:261-301, disc. (1990)
Shoham et al, *Fertil. Steril.* 56:1048-1053 (1991)
Singh et al, *Fertil. Steril.* 52:739-744 (1989)
Smith et al, *J. Biol. Chem.* 268:795-802 (1993)
Sprengel et al, *Mol. Endocrinol.* 4:525-530, (1990)
Sugahara et al, *Proc. Natl. Acad. Sci., USA* 92:2041-2045 (1995)
Suganuma et al, *J. Biol. Chem.* 264:19302-19307 (1989)
Sun et al, *Annu. Rev. Biophys. Biomol. Struct.* 24:269-291 (1995)
Talwar et al, *Fertil. Steril.* 46:120-126 (1986)
Talwar et al, *Indian. Journal. of Experimental. Biology.* 30:947-950 (1992)
van Dijk et al, *Endocrinology* 132:534-538 (1993)
Wang et al, in *Ovulation Induction: Basic Science and Clinical Advances*, M. Filicori and C. Flamigni, editors, Excerpta. Medica. Int'l. Congr. Series 1046, Elsevier Science B.V. Amsterdam (1994), pp. 191-196
Weare et al, *J. Biol. Chem.* 254:6964-6971 (1979)
Weare et al, *J. Biol. Chem.* 254:6972-6979 (1979)
Wehmann et al, *Ann. Endocrinol.* (Paris) 45:291-295 (1984)
Wu et al, *Structure* 2:545-558 (1994)
Xie et al, *J. Biol. Chem.* 265:21411-21414 (1990)
Yanisch-Perron et al, *Gene* 33:103-119 (1985)

What is claimed is:

1. A glycoprotein hormone consisting of an α-subunit and a β-subunit, wherein said glycoprotein hormone is a gonadotropin, wherein the amino acid sequence of one or both of said gonadotropin subunits is modified so as to create one or more intersubunit disulfide bonds, each between an α-subunit cysteine and a β-subunit cysteine, said gonadotropin retaining at least a portion of the activity of stimulating the corresponding native gonadotropin receptor, and wherein the disulfide bond does not involve residues that are important for receptor binding or receptor binding specificity, and does not contort the protein into a non-active conformation.

2. The glycoprotein hormone in accordance with claim 1, wherein each of the cysteines that create the intersubunit bonds is either a native cysteine or a cysteine disposed within two residues of a native cysteine residue position in said gonadotropin.

3. The glycoprotein hormone in accordance with claim 2, wherein the amino acid sequences of said gonadotropin subunits are modified so as to create an intersubunit disulfide bond between a cysteine residue located within a cysteine knot of said α-subunit and a cysteine residue located within a cysteine knot of said β-subunit.

4. The glycoprotein hormone in accordance with claim 2, wherein said intersubunit disulfide bond is between a native cysteine residue and a residue which is modified so as to be replaced by a cysteine residue.

5. The glycoprotein hormone in accordance with claim 4, wherein said intersubunit disulfide bond is between a native cysteine residue of said α-subunit and a residue of said β-subunit which is modified so as to be replaced by a cysteine residue.

6. The glycoprotein hormone in accordance with claim 5, wherein the glycoprotein hormone is hCG or hLH and wherein the amino acid sequence of the hCG or hLH β-subunit is modified to replace residue Tyr37 with a cysteine to form an intersubunit disulfide bond between a native Cys31 residue of said human α-subunit and residue 37 of said hCG or hLH β-subunit which is replaced with a cysteine residue.

7. The glycoprotein hormone in accordance with claim 5, wherein the glycoprotein hormone is hFSH and wherein the amino acid sequence of the hFSH β-subunit is modified to replace residue Tyr31 with a cysteine to form an intersubunit disulfide bond between a native Cys31 residue of said human α-subunit and residue 31 of said hFSH β-subunit which is replaced with a cysteine residue.

8. The glycoprotein hormone in accordance with claim 5, wherein the glycoprotein hormone is hTSH and wherein the amino acid sequence of the hTSH β-subunit is modified to replace Tyr30 with a cysteine to form an intersubunit disulfide bond between a native Cys31 residue of said human α-subunit and residue 30 of said hTSH β-subunit which is replaced with a cysteine residue.

9. The glycoprotein hormone in accordance with claim 2, wherein the amino acid sequences of said gonadotropin subunits are modified so as to create an intersubunit disulfide bond between a cysteine residue located within loop 2 of said α-subunit and a cysteine residue located within loop 2 of said β-subunit.

10. The glycoprotein hormone in accordance with claim 2, wherein the amino acid sequences of said gonadotropin subunits are modified so as to create an intersubunit disulfide bond between a cysteine residue located within eight residues of the C-terminus of said α-subunit and a cysteine residue located within loop 2 of said β-subunit.

11. The glycoprotein hormone of claim 2, wherein said gonadotropin is selected from the group consisting of human chorionic gonadotropin (hCG), human luteinizing hormone (hLH), human follicle stimulating hormone (hFSH), and functional muteins thereof.

12. The glycoprotein hormone in accordance with claim 1, which is selected from the group of functional glycoprotein hormones consisting of human chorionic gonadotropin (hCG), human luteinizing hormone (hLH), human follicle stimulating hormone (hFSH), human thyroid stimulating hormone (hTSH), and functional muteins thereof, wherein the amino acid sequence of one or both of said glycoprotein hormone subunits is modified so as to create an intersubunit disulfide bond between loop 3 of said α-subunit and loop 2 of said β-subunit.

13. The glycoprotein hormone in accordance with claim 12, wherein the glycoprotein hormone is hFSH in which the amino acid sequence of said α-subunit is modified to replace Val76 with a cysteine and the amino acid sequence of said hFSH β-subunit is modified to replace Val38 with cysteine so as to create an intersubunit disulfide bond between residue 76 of said α-subunit and residue 38 of said hFSH β-subunit.

14. The glycoprotein hormone in accordance with claim 1, which is selected from the group of functional glycoprotein hormones consisting of human chorionic gonadotropin (hCG), human luteinizing hormone (hLH), human follicle stimulating hormone (hFSH), human thyroid stimulating hormone (hTSH), and functional muteins thereof, wherein the amino acid sequence of one or both of said glycoprotein hormone subunits is modified so as to create an intersubunit disulfide bond between loop 1 of said α-subunit and loop 2 of said β-subunit.

15. The glycoprotein hormone in accordance with claim 1, wherein said glycoprotein hormone comprises an intersubunit disulfide bond between the N-terminus of an α-subunit and the N-terminus of a β-subunit.

16. The glycoprotein hormone in accordance with claim 1, wherein said β-subunit is selected from the group of β-subunits consisting of hCG and hLH.

17. The glycoprotein in accordance with claim 16, wherein said glycoprotein hormone comprises an intersubunit disulfide bond between one or more amino acid pairs (α5-β8), (α51-β99), (α31-β37), (α31-β6) and (α27-β44).

18. The glycoprotein hormone in accordance with claim 1, wherein said β-subunit is hFSH β-subunit.

19. The glycoprotein hormone in accordance with claim 18, wherein said glycoprotein hormone comprises an intersubunit disulfide bond between one or more amino acid pairs (α5-β2), (α29-β35), (α37-β27), (α55-β92), (α31-β31), (α27-β38), (α76-β38), (α59-β34), (α34-β50), (α57-β50), (α87-β48), (α61-β36) and (α75-β40).

20. A pharmaceutical composition comprising an effective amount of the glycoprotein hormone according to claim 1 and a pharmaceutically acceptable excipient.

21. The pharmaceutical composition in accordance with claim 20 which is a liquid.

22. A method of treating infertility comprising administering a therapeutically effective amount of a pharmaceutically composition according to claim 20 to a patient in need thereof, wherein the infertility is treated.

23. A recombinant DNA molecule comprising a nucleotide sequence encoding an α-subunit of the glycoprotein hormone according to claim 1, wherein the sequence of the α-subunit of said glycoprotein hormone is modified so as to create said one or more intersubunit disulfide bonds.

24. The recombinant DNA molecule in accordance with claim 23, which is an expression vector.

25. A eukaryotic host cell transformed with the recombinant DNA molecule according to claim 20, wherein said host cell is capable of expressing the α-subunit of a glycoprotein hormone.

26. A recombinant DNA molecule comprising a nucleotide sequence encoding a β-subunit of the glycoprotein hormone according claim 1, wherein the sequence of the β-subunit of said glycoprotein hormone is modified so as to create said one or more intersubunit disulfide bonds.

27. The recombinant DNA molecule in accordance with claim 26, which is an expression vector.

28. A eukaryotic host cell transformed with the recombinant DNA molecule according to claim 27, wherein said host cell is capable of expressing the β-subunit of a glycoprotein hormone.

29. A process for preparing a glycoprotein hormone in accordance with claim 1, comprising the steps of:
   culturing a eukaryotic host cell transformed with nucleotide sequences of the α- and β-subunits carried on the same expression vector or on separate expression vectors to express the glycoprotein hormone; and
   recovering the expressed glycoprotein hormone.

30. A method of improving the stability of glycoprotein hormone heterodimers, comprising the steps of:
   identifying a residue on each subunit of a glycoprotein or functional mutein thereof that has the potential to form an intersubunit disulfide bond with or without modification of one or more of the identified residues; and
   modifying one or more of the identified residues to form an analog of a glycoprotein hormone in accordance with claim 1, wherein said glycoprotein hormone has improved stability and retains at least a portion of the activity of stimulating the corresponding glycoprotein hormone receptor.

31. A gonadotropin having an α-subunit and a β-subunit, wherein the amino acid sequence of one or both of said glycoprotein hormone subunits is modified to create an intersubunit disulfide bond between an α-subunit cysteine and a β-subunit cysteine selected from the group consisting of hCG α31-β37, hCG α5-α8, hCG α29-β41, hCG α35-β35, hCG α37-β33, and hCG α51-β99.

32. A gonadotropin having an α-subunit and a β-subunit, wherein the amino acid sequence of one or both of said glycoprotein hormone subunits is modified to create an intersubunit disulfide bond between an α-subunit cysteine and a β-subunit cysteine selected from the group consisting of hLH α31-β37, hLH α5-β8, hLH α29-β41, hLH α35-β35, hLH α37-β33, and hLH α51-β99.

33. The glycoprotein hormone in accordance with claim 2, wherein the amino acid sequence of one or both of said gonadotropin subunits is modified so as to create an intersubunit disulfide bond between a cysteine residue located within two residues of a cysteine knot of said α-subunit and a cysteine residue located within two residues of a cysteine knot of said β-subunit.

34. A glycoprotein hormone consisting of an α-subunit and a β-subunit, wherein said glycoprotein hormone comprises an intersubunit disulfide bond between an amino acid pair selected from the group consisting of hCG α31-β37, hLH α31-β37, hFSH α31-β31, hTSH α31-β30, hCG α51-β99, and hLH α51-β99.

* * * * *

```
                        SEQUENCE LISTING (1) GENERAL INFORMATION:

(iii) NUMBER OF SEQUENCES: 138

(2) INFORMATION FOR SEQ ID NO:1:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

(2) INFORMATION FOR SEQ ID NO:2:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30
```

Ile Cys Ala Gly Tyr Cys Pro Thr Met Thr Arg Val Leu Gln Gly Val
                35                  40                  45

Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Pro Ser Leu
            115                 120                 125

Pro Ser Pro Ser Arg Leu Pro Gly Pro Ser Asp Thr Pro Ile Leu Pro
    130                 135                 140

Gln
145

(2) INFORMATION FOR SEQ ID NO:3:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Asp Tyr Tyr Arg Lys Tyr Ala Ala Ile Phe Leu Val Thr Leu Ser
 1                   5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
                 35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
        115

(2) INFORMATION FOR SEQ ID NO:4:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Asp Tyr Tyr Arg Lys Tyr Ala Ala Ile Phe Leu Val Thr Leu Ser
 1                   5                  10                  15

Val Phe Leu His Val Leu His Ser Ala Pro Asp Val Gln Asp Ser Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
            100                 105                 110

Tyr His Lys Ser
            115

(2) INFORMATION FOR SEQ ID NO:5:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Met Glu Met Phe Gln Gly Leu Leu Leu Leu Leu Leu Ser Met Gly
 1                   5                  10                  15

Gly Thr Trp Ala Ser Lys Glu Pro Leu Arg Pro Arg Cys Arg Pro Ile
                 20                  25                  30

Asn Ala Thr Leu Ala Val Glu Lys Glu Gly Cys Pro Val Cys Ile Thr
             35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
            165

(2) INFORMATION FOR SEQ ID NO:6:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Met Glu Met Phe Gln Gly Leu Leu Leu Leu Leu Leu Ser Met Gly
 1                   5                  10                  15

```
Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Cys Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:7:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Thr Val Arg Gly Leu Gly Pro Ser
                115                 120                 125

Tyr Cys Ser Phe Gly Glu Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:8:
```

(i) SEQUENCE CHARACTERISTICS:
    (A) LENGTH: 165 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

```
Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Cys Cys Pro Thr Met Thr Arg Val
 50                      55                      60

Leu Gln Gly Val Leu Pro Ala Leu Pro Gln Val Val Cys Asn Tyr Arg
 65                      70                      75              80

Asp Val Arg Phe Glu Ser Ile Arg Leu Pro Gly Cys Pro Arg Gly Val
            85                      90                      95

Asn Pro Val Val Ser Tyr Ala Val Ala Leu Ser Cys Gln Cys Ala Leu
            100                     105                     110

Cys Arg Arg Ser Thr Thr Asp Cys Thr Val Arg Gly Leu Gly Pro Ser
            115                     120                     125

Tyr Cys Ser Phe Gly Glu Phe Gln Asp Ser Ser Ser Lys Ala Pro
            130                 135                 140

Pro Pro Ser Leu Pro Ser Pro Ser Arg Leu Pro Gly Pro Ser Asp Thr
 145                 150                     155                     160

Pro Ile Leu Pro Gln
                165
```

(2) INFORMATION FOR SEQ ID NO:9:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
 50                  55                      60

Leu Arg Ser Lys Lys Thr Met Leu Val Gln Cys Asn Val Thr Ser Glu
 65                      70                      75              80

Ser Thr Cys Cys Val Ala Lys Ser Tyr Asn Arg Val Thr Val Met Gly
            85                      90                      95

Gly Phe Lys Val Glu Asn His Thr Ala Cys His Cys Ser Thr Cys Tyr
            100                     105                     110

Tyr His Lys Ser
            115
```

(2) INFORMATION FOR SEQ ID NO:10:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Cys Cys Gly Gly Pro Lys Asp His Pro Leu
            115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165
```

(2) INFORMATION FOR SEQ ID NO:11:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110
```

```
Cys Arg Arg Ser Thr Thr Cys Cys Thr Val Arg Gly Leu Gly Pro Ser
            115                 120                 125

Tyr Cys Ser Phe Gly Glu Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
            165

(2) INFORMATION FOR SEQ ID NO:12:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Ser Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Cys Asn Val Thr Ser Glu
65                  70                  75                  80

Ser Thr Cys Cys Val Ala Lys Ser Tyr Asn Arg Val Thr Val Met Gly
            85                  90                  95

Gly Phe Lys Val Glu Asn His Thr Ala Cys His Cys Ser Thr Cys Tyr
            100                 105                 110

Tyr His Lys Ser
        115

(2) INFORMATION FOR SEQ ID NO:13:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Cys Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
            85                  90                  95
```

```
Asn Pro Val Val Ser Tyr Ala Val Ala Leu Ser Cys Gln Cys Ala Leu
            100                 105                 110

Cys Arg Arg Ser Thr Thr Cys Cys Gly Gly Pro Lys Asp His Pro Leu
            115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
            165

(2) INFORMATION FOR SEQ ID NO:14:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Asp Tyr Tyr Arg Lys Tyr Ala Ala Ile Phe Leu Val Thr Leu Ser
1               5                   10                  15

Val Phe Leu His Val Leu His Ser Ala Pro Val Gln Asp Ala Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
            85                  90                  95

Gly Phe Lys Val Glu Asn His Thr Ala Cys His Cys Ser Thr Cys Tyr
            100                 105                 110

Tyr His Lys Ser
            115

(2) INFORMATION FOR SEQ ID NO:15:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Met Lys Thr Leu Gln Phe Phe Phe Leu Phe Leu Leu Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Cys Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80
```

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu (2) INFORMATION FOR SEQ ID NO:16:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Met Asp Tyr Tyr Arg Lys Tyr Ala Ala Ile Phe Leu Val Thr Leu Ser
1               5                   10                  15

Val Phe Leu His Val Leu His Ser Ala Pro Val Cys Asp Cys Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

(2) INFORMATION FOR SEQ ID NO:17:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Met Glu Met Phe Gln Gly Leu Leu Leu Leu Leu Leu Ser Met Gly Gly
1               5                   10                  15

Gly Thr Trp Ala Ser Lys Glu Pro Leu Arg Pro Cys Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
            85                  90                  95

Asn Pro Val Val Ser Tyr Ala Val Ala Leu Ser Cys Gln Cys Ala Leu

```
                            100                 105                 110
Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:18:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Met Lys Thr Leu Gln Phe Phe Leu Phe Leu Leu Trp Lys Ala Ile
1               5                   10                  15

Cys Cys Asn Cys Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu (2) INFORMATION FOR SEQ ID NO:19:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Cys Cys Pro Thr Met Met Arg Val
50                  55                  60

Leu Gln Ala Val Leu Pro Pro Leu Pro Gln Val Val Cys Thr Tyr Arg
65                  70                  75                  80
```

```
Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
    130                 135                 140
```

(2) INFORMATION FOR SEQ ID NO:20:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Met Glu Met Leu Gln Gly Leu Leu Leu Leu Leu Leu Ser Met Gly
1               5                   10                  15

Gly Ala Trp Ala Ser Arg Glu Pro Leu Arg Pro Cys Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
    130                 135                 140
```

(2) INFORMATION FOR SEQ ID NO:21:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Met Thr Ala Leu Phe Leu Met Ser Met Leu Phe Gly Leu Ala Cys Gly
1               5                   10                  15

Gln Ala Met Ser Phe Cys Ile Pro Thr Glu Tyr Met Thr His Ile Glu
            20                  25                  30

Arg Arg Glu Cys Ala Tyr Cys Leu Thr Ile Asn Thr Thr Ile Cys Ala
        35                  40                  45

Gly Cys Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Ile Tyr Arg
65                  70                  75                  80
```

Thr Val Glu Ile Pro Gln Cys Pro Leu His Val Ala Pro Tyr Phe Ser
                85                  90                  95

Tyr Pro Val Ala Leu Ser Cys Lys Cys Gly Lys Cys Asn Thr Asp Tyr
            100                 105                 110

Ser Asp Cys Ile His Glu Ala Ile Lys Thr Asn Tyr Cys Thr Lys Pro
        115                 120                 125

Gln Lys Ser Tyr
    130

(2) INFORMATION FOR SEQ ID NO:22:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Met Thr Ala Leu Phe Leu Met Ser Met Leu Phe Gly Leu Ala Cys Gly
1               5                   10                  15

Gln Ala Met Ser Cys Cys Ile Pro Thr Glu Tyr Met Thr His Ile Glu
            20                  25                  30

Arg Arg Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Ile Tyr Arg
65                  70                  75                  80

Thr Val Glu Ile Pro Gln Cys Pro Leu His Val Ala Pro Tyr Phe Ser
                85                  90                  95

Tyr Pro Val Ala Leu Ser Cys Lys Cys Gly Lys Cys Asn Thr Asp Tyr
            100                 105                 110

Ser Asp Cys Ile His Glu Ala Ile Lys Thr Asn Tyr Cys Thr Lys Pro
        115                 120                 125

Gln Lys Ser Tyr
    130

(2) INFORMATION FOR SEQ ID NO:23:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80

```
Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
               100                 105                 110

Pro Gln Leu Ser Gly Leu Leu Phe Leu
           115                 120

(2) INFORMATION FOR SEQ ID NO:24:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Asn Ser Cys Glu Leu Thr Asn Ile Thr Ile Ala Val Glu Lys Glu Gly
1               5                  10                  15

Cys Gly Phe Cys Ile Thr Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
               100                 105                 110

(2) INFORMATION FOR SEQ ID NO:25:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Phe Cys Ile Pro Thr Glu Tyr Met Thr His Ile Glu Arg Arg Glu Cys
1               5                  10                  15

Ala Tyr Cys Leu Thr Ile Asn Thr Thr Ile Cys Ala Gly Tyr Cys Met
                20                  25                  30

Thr Arg Asp Ile Asn Gly Lys Leu Phe Leu Pro Lys Tyr Ala Leu Ser
                35                  40                  45

Gln Asp Val Cys Thr Tyr Arg Asp Phe Ile Tyr Arg Thr Val Glu Ile
           50                  55                  60

Pro Gln Cys Pro Leu His Val Ala Pro Tyr Phe Ser Tyr Pro Val Ala
65                  70                  75                  80

Leu Ser Cys Lys Cys Gly Lys Cys Asn Thr Asp Tyr Ser Asp Cys Ile
                85                  90                  95

His Glu Ala Ile Lys Thr Asn Tyr Cys Thr Lys Pro Gln Lys Ser Tyr
               100                 105                 110

(2) INFORMATION FOR SEQ ID NO:26:
```

```
    (i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Phe Pro Asp Gly Glu Phe Thr Met Gln Gly Cys Pro Glu Cys Lys Leu
1               5                  10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

(2) INFORMATION FOR SEQ ID NO:27:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Phe Pro Asp Gly Glu Phe Thr Met Gln Gly Cys Pro Glu Cys Lys Leu
1               5                  10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

(2) INFORMATION FOR SEQ ID NO:28:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Phe Pro Asp Gly Glu Phe Thr Met Gln Gly Cys Pro Glu Cys Lys Leu
1               5                  10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
```

-continued

```
                35                  40                  45
Lys Thr Met Leu Val Pro Lys Asn Ile Thr Ser Glu Ala Thr Cys Cys
 50                  55                  60

Val Ala Lys Ala Phe Thr Lys Ala Thr Val Met Gly Asn Val Arg Val
 65                  70                  75                  80

Glu Asn His Thr Glu Cys His Cys Ser Thr Cys Tyr Tyr His Lys Ser
                 85                  90                  95

(2) INFORMATION FOR SEQ ID NO:29:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Phe Pro Asp Gly Glu Phe Thr Thr Gln Asp Cys Pro Glu Cys Lys Leu
 1               5                  10                  15

Arg Glu Asn Lys Tyr Phe Phe Lys Leu Gly Val Pro Ile Tyr Gln Cys
                20                  25                  30

Lys Gly Cys Cys Phe Ser Arg Ala Tyr Pro Thr Pro Ala Arg Ser Arg
                35                  40                  45

Lys Thr Met Leu Val Pro Lys Asn Ile Thr Ser Glu Ser Thr Cys Cys
 50                  55                  60

Val Ala Lys Ala Phe Ile Arg Val Thr Val Met Gly Asn Ile Lys Leu
 65                  70                  75                  80

Glu Asn His Thr Gln Cys Tyr Cys Ser Thr Cys Tyr His His Lys Ile
                85                  90                  95

(2) INFORMATION FOR SEQ ID NO:30:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Leu Pro Asp Gly Asp Leu Ile Ile Gln Gly Cys Pro Glu Cys Lys Leu
 1               5                  10                  15

Lys Glu Asn Lys Tyr Phe Ser Lys Leu Gly Ala Pro Ile Tyr Gln Cys
                20                  25                  30

Met Gly Cys Cys Phe Ser Arg Ala Tyr Pro Thr Pro Ala Arg Ser Lys
                35                  40                  45

Lys Thr Met Leu Val Pro Lys Asn Ile Thr Ser Glu Ala Thr Cys Cys
 50                  55                  60

Val Ala Lys Ser Phe Thr Lys Ala Thr Val Met Gly Asn Ala Arg Val
 65                  70                  75                  80

Glu Asn His Thr Lys Cys His Cys Ser Thr Cys Tyr Tyr His Lys Ser
                85                  90                  95

(2) INFORMATION FOR SEQ ID NO:31:

(i) SEQUENCE CHARACTERISTICS:
        (A) LENGTH: 96 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:31:

Leu Pro Asp Gly Asp Phe Ile Ile Gln Gly Cys Pro Glu Cys Lys Leu
1               5                   10                  15

Lys Glu Asn Lys Tyr Phe Ser Lys Leu Gly Ala Pro Ile Tyr Gln Cys
                20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
        50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

(2) INFORMATION FOR SEQ ID NO:32:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Phe Pro Asp Gly Glu Phe Ala Met Gln Gly Cys Pro Glu Cys Lys Leu
1               5                   10                  15

Lys Glu Asn Lys Tyr Phe Ser Lys Leu Gly Ala Pro Ile Tyr Gln Cys
                20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Gly Cys Cys
        50                  55                  60

Val Ala Lys Ala Phe Thr Lys Ala Thr Val Met Gly Asn Ala Lys Val
65                  70                  75                  80

Glu Asn His Thr Glu Cys His Cys Ser Thr Cys Tyr Tyr His Lys Ser
                85                  90                  95

(2) INFORMATION FOR SEQ ID NO:33:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Phe Pro Asp Gly Glu Phe Leu Met Gln Gly Cys Pro Glu Cys Lys Leu
1               5                   10                  15

Lys Glu Asn Arg Phe Phe Ser Lys Pro Gly Ala Pro Ile Tyr Gln Cys
                20                  25                  30

Thr Gly Cys Cys Phe Ser Arg Ala Tyr Pro Thr Pro Met Arg Ser Lys
            35                  40                  45

Lys Thr Met Leu Val Pro Lys Asn Ile Thr Ser Glu Ala Thr Cys Cys
        50                  55                  60

```
Val Ala Lys Ala Phe Thr Lys Ile Thr Leu Lys Asp Asn Val Arg Ile
 65                  70                  75                  80

Glu Asn His Thr Glu Cys His Cys Ser Thr Cys Tyr Tyr His Tyr Ser
                 85                  90                  95
```

(2) INFORMATION FOR SEQ ID NO:34:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Tyr Pro Arg Asn Asp Met Asn Asn Phe Gly Cys Glu Glu Cys Lys Leu
 1               5                  10                  15

Lys Glu Asn Asn Ile Phe Ser Lys Pro Gly Ala Pro Val Tyr Gln Cys
                 20                  25                  30

Met Gly Cys Cys Phe Ser Arg Ala Tyr Pro Thr Pro Leu Arg Ser Lys
                 35                  40                  45

Lys Thr Met Leu Val Pro Lys Asn Ile Thr Ser Glu Ala Thr Cys Cys
 50                  55                  60

Val Ala Lys Glu Val Lys Lys Ile Leu Val Asn Asp Val Lys Leu Val
 65                  70                  75                  80

Asn His Thr Asp Cys His Cys Ser Thr Cys Tyr Tyr His Lys Ser
                 85                  90                  95
```

(2) INFORMATION FOR SEQ ID NO:35:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Tyr Pro Arg Asn Tyr Met Asn Asn Phe Gly Cys Glu Glu Cys Thr Leu
 1               5                  10                  15

Lys Glu Asn Asn Ile Phe Ser Lys Pro Gly Ala Pro Val Tyr Gln Cys
                 20                  25                  30

Met Gly Cys Cys Phe Ser Arg Ala Tyr Pro Thr Pro Leu Arg Ser Lys
                 35                  40                  45

Lys Thr Met Leu Val Pro Lys Asn Ile Thr Ser Glu Ala Thr Cys Cys
 50                  55                  60

Val Ala Lys Glu Phe Lys Gln Val Leu Val Asn Asp Ile Lys Leu Val
 65                  70                  75                  80

Asn His Thr Asp Cys His Cys Ser Thr Cys Tyr Tyr His Lys Ser
                 85                  90                  95
```

(2) INFORMATION FOR SEQ ID NO:36:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Tyr Pro Asn Asn Glu Met Ala Arg Gly Gly Cys Asp Glu Cys Arg Leu
1               5                   10                  15

Gln Glu Asn Lys Ile Phe Ser Lys Pro Ser Ala Pro Ile Phe Gln Cys
                20                  25                  30

Val Gly Cys Cys Phe Ser Arg Ala Tyr Pro Thr Pro Leu Arg Ser Lys
            35                  40                  45

Lys Thr Met Leu Val Pro Lys Asn Ile Thr Ser Glu Ala Thr Cys Cys
        50                  55                  60

Val Ala Arg Glu Val Thr Arg Leu Asp Asn Met Lys Leu Glu Asn His
65                  70                  75                  80

Thr Asp Cys Gly Cys Ser Thr Cys Tyr Tyr His Lys Phe
                85                  90
```

(2) INFORMATION FOR SEQ ID NO:37:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Tyr Pro Asn Asn Glu Ile Ser Arg Gly Gly Cys Asp Glu Cys Arg Leu
1               5                   10                  15

Lys Asp Asn Lys Phe Phe Ser Lys Pro Ser Ala Pro Ile Phe Gln Cys
                20                  25                  30

Val Gly Cys Cys Phe Ser Arg Ala Tyr Pro Thr Pro Leu Arg Ser Lys
            35                  40                  45

Lys Thr Met Leu Val Pro Lys Asp Ile Thr Ser Glu Ala Thr Cys Cys
        50                  55                  60

Val Ala Arg Glu Val Thr Lys Leu Asp Asn Met Lys Leu Glu Asn His
65                  70                  75                  80

Thr Asp Cys His Cys Ser Thr Cys Tyr Tyr His Lys Ser
                85                  90
```

(2) INFORMATION FOR SEQ ID NO:38:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Tyr Gln Asn Ser Asp Met Thr Asn Val Gly Cys Glu Glu Cys Lys Leu
1               5                   10                  15

Lys Glu Asn Lys Val Phe Ser Asn Pro Gly Ala Pro Val Leu Gln Cys
                20                  25                  30

Thr Gly Cys Cys Phe Ser Arg Ala Tyr Pro Thr Pro Leu Gln Ser Lys
            35                  40                  45

Lys Ala Met Leu Val Pro Lys Asn Ile Thr Ser Glu Ala Thr Cys Cys
        50                  55                  60

Val Ala Lys Glu Gly Glu Arg Val Val Asp Asn Ile Lys Leu Thr
65                  70                  75                  80

Asn His Thr Glu Cys Trp Cys Asn Thr Cys Tyr His His Lys Ser
                85                  90                  95
```

(2) INFORMATION FOR SEQ ID NO:39:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Tyr Pro Asn Ser Asp Lys Thr Asn Met Gly Cys Glu Glu Cys Lys Leu
1               5                   10                  15

Lys Pro Asn Thr Ile Phe Pro Asn Pro Gly Ala Pro Ile Met Gln Cys
                20                  25                  30

Thr Gly Cys Cys Phe Ser Arg Ala Tyr Pro Thr Pro Leu Arg Ser Lys
            35                  40                  45

Gln Thr Met Leu Val Pro Lys Asn Ile Thr Ser Glu Ala Thr Cys Cys
    50                  55                  60

Val Ala Lys Glu Gly Glu Arg Val Thr Thr Lys Asp Gly Phe Pro Val
65                  70                  75                  80

Thr Asn His Thr Glu Cys His Cys Ser Thr Cys Tyr Tyr His Lys Ser
                85                  90                  95
```

(2) INFORMATION FOR SEQ ID NO:40:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Ser Arg Gly Pro Leu Arg Pro Leu Cys Arg Pro Ile Asn Ala Thr Leu
1               5                   10                  15

Ala Ala Glu Lys Glu Ala Cys Pro Ile Cys Ile Thr Phe Thr Thr Ser
                20                  25                  30

Ile Cys Ala Gly Tyr Cys Pro Ser Met Val Arg Val Met Pro Ala Ala
            35                  40                  45

Leu Pro Ala Ile Pro Gln Pro Val Cys Thr Tyr Arg Glu Leu Arg Phe
    50                  55                  60

Ala Ser Ile Arg Leu Pro Gly Cys Pro Pro Gly Val Asp Pro Met Val
65                  70                  75                  80

Ser Phe Pro Val Ala Leu Ser Cys His Cys Gly Pro Cys Gln Ile Lys
                85                  90                  95

Thr Thr Asp Cys Gly Val Phe Arg Asp Gln Pro Leu Ala Cys Ala Pro
            100                 105                 110

Gln Ala Ser Ser Ser Lys Asp Pro Pro Ser Gln Pro Leu Thr Ser
        115                 120                 125

Thr Ser Thr Pro Thr Pro Gly Ala Ser Arg Arg Ser Ser His Pro Leu
    130                 135                 140

Pro Ile Lys Thr Ser
145
```

(2) INFORMATION FOR SEQ ID NO:41:

(i) SEQUENCE CHARACTERISTICS:
        (A) LENGTH: 121 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Ser Arg Gly Pro Leu Arg Pro Leu Cys Arg Pro Ile Asn Ala Thr Leu
1               5                   10                  15

Ala Ala Glu Asn Glu Ala Cys Pro Val Cys Ile Thr Phe Thr Thr Thr
            20                  25                  30

Ile Cys Ala Gly Tyr Cys Pro Ser Met Val Arg Val Leu Pro Ala Ala
            35                  40                  45

Leu Pro Pro Val Pro Gln Pro Val Cys Thr Tyr His Glu Leu His Phe
        50                  55                  60

Ala Ser Ile Arg Leu Pro Gly Cys Pro Pro Gly Val Asp Pro Met Val
65                  70                  75                  80

Ser Phe Pro Val Ala Leu Ser Cys Arg Cys Gly Pro Cys Arg Leu Ser
                85                  90                  95

Asn Ser Asp Cys Gly Gly Pro Arg Ala Gln Ser Leu Ala Cys Asp Arg
            100                 105                 110

Pro Leu Leu Pro Gly Leu Leu Phe Leu
        115                 120
```

(2) INFORMATION FOR SEQ ID NO:42:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Leu Gly Gly Gly Gly Arg Pro Pro Cys Arg Pro Ile Asn Val Thr Val
1               5                   10                  15

Ala Val Glu Lys Asp Gly Cys Pro Gln Cys Met Ala Val Thr Thr Thr
            20                  25                  30

Ala Cys Gly Gly Thr Cys Arg Thr Arg Glu Pro Val Tyr Arg Ser Pro
            35                  40                  45

Leu Gly Pro Pro Pro Gln Ser Ala Cys Thr Tyr Gly Ala Leu Arg Tyr
        50                  55                  60

Glu Arg Trp Ala Leu Trp Gly Cys Pro Ile Gly Ser Asp Pro Arg Val
65                  70                  75                  80

Leu Leu Pro Val Ala Leu Ser Cys Arg Cys Ala Arg Cys Pro Met Ala
                85                  90                  95

Thr Ser Asp Cys Thr Val Gln Gly Leu Gly Pro Ala Phe Cys Gly Ala
            100                 105                 110

Pro Gly Gly Phe Gly Gly Glu
        115
```

(2) INFORMATION FOR SEQ ID NO:43:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Ser Arg Gly Pro Leu Arg Pro Leu Cys Gln Pro Ile Asn Ala Thr Leu
1               5                   10                  15

Ala Ala Glu Lys Glu Ala Cys Pro Val Cys Ile Thr Phe Thr Thr Ser
            20                  25                  30

Ile Cys Ala Gly Tyr Cys Pro Ser Met Lys Arg Val Leu Pro Val Ile
            35                  40                  45

Leu Pro Pro Met Pro Gln Arg Val Cys Thr Tyr His Glu Leu Arg Phe
50                      55                  60

Ala Ser Val Arg Ile Pro Gly Cys Pro Pro Gly Val Asp Pro Met Val
65                  70                  75                  80

Ser Phe Pro Val Ala Leu Ser Cys His Cys Gly Pro Cys Arg Leu Ser
                85                  90                  95

Ser Thr Asp Cys Gly Gly Pro Arg Thr Gln Pro Leu Ala Cys Asp His
                100                 105                 110

Pro Pro Leu Pro Asp Ile Leu Phe Leu
            115                 120

(2) INFORMATION FOR SEQ ID NO:44:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Ser Arg Gly Pro Leu Arg Pro Leu Cys Gln Pro Ile Asn Ala Thr Leu
1               5                   10                  15

Ala Ala Glu Lys Glu Ala Cys Pro Val Cys Ile Thr Phe Thr Thr Ser
            20                  25                  30

Ile Cys Ala Gly Tyr Cys Pro Ser Met Lys Arg Val Leu Pro Val Ile
            35                  40                  45

Leu Pro Pro Met Pro Gln Arg Val Cys Thr Tyr His Glu Leu Arg Phe
50                      55                  60

Ala Ser Val Arg Leu Pro Gly Cys Pro Pro Gly Val Asp Pro Met Val
65                  70                  75                  80

Ser Phe Pro Val Ala Leu Ser Cys His Cys Gly Pro Cys Arg Leu Ser
                85                  90                  95

Ser Thr Asp Cys Gly Pro Gly Arg Thr Gln Pro Leu Ala Cys Asp His
                100                 105                 110

Pro Pro Leu Pro Asp Ile Leu
            115

(2) INFORMATION FOR SEQ ID NO:45:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

Pro Glu Pro Ala Arg Gly Pro Leu Arg Pro Leu Cys Arg Pro Val Asn
1               5                   10                  15

Ala Thr Leu Ala Ala Glu Asn Glu Ala Cys Pro Val Cys Ile Thr Phe

```
            20                  25                  30
Thr Thr Ser Ile Cys Ala Gly Tyr Cys Pro Ser Met Val Arg Val Leu
        35                  40                  45

Pro Ala Ala Leu Pro Pro Val Pro Gln Pro Val Cys Thr Tyr Arg Glu
50                  55                  60

Leu Arg Phe Ala Ser Ile Arg Leu Pro Gly Cys Pro Pro Gly Val Asp
65                  70                  75                  80

Pro Glu Val Ser Phe Pro Val Ala Leu Ser Cys Arg Cys Gly Pro Cys
                85                  90                  95

Arg Leu Ser Ser Ser Asp Cys Gly Gly Pro Arg Ala Glu Pro Leu Ala
            100                 105                 110

Cys Asp Leu Pro His Leu Pro Gly
            115                 120
```

(2) INFORMATION FOR SEQ ID NO:46:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Ser Leu Met Gln Pro Cys Gln Pro Ile Asn Gln Thr Val Ser Leu Glu
1               5                   10                  15

Lys Glu Gly Cys Pro Thr Cys Leu Val Ile Arg Ala Pro Ile Cys Ser
            20                  25                  30

Gly His Cys Val Thr Lys Glu Pro Val Phe Lys Ser Pro Phe Ser Thr
        35                  40                  45

Val Thr Gln His Val Cys Thr Tyr Arg Asp Val Arg Tyr Glu Met Ile
    50                  55                  60

Arg Leu Pro Asp Cys Pro Pro Trp Ser Glu Pro His Val Thr Tyr Pro
65                  70                  75                  80

Val Ala Leu Ser Cys Asp Cys Ser Leu Cys Asn Met Asp Thr Ser Asp
                85                  90                  95

Cys Thr Ile Glu Ser Leu Gln Pro Asp Phe Cys Ile Thr Gln Arg Val
            100                 105                 110

Leu Thr Asp Gly Asp Met Trp
            115
```

(2) INFORMATION FOR SEQ ID NO:47:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Gly Thr Glu Cys Arg Tyr Gly Cys Arg Leu Asn Asn Met Thr Ile Ile
1               5                   10                  15

Val Glu Arg Glu Asp Cys His Gly Ser Ile Thr Ile Thr Thr Cys Ala
            20                  25                  30

Gly Leu Cys Glu Thr Thr Asp Leu Asn Tyr Glu Ser Thr Trp Leu Pro
        35                  40                  45

Arg Ser Gln Gly Val Cys Asn Phe Lys Glu Trp Ser Tyr Glu Lys Val
```

```
                50                  55                  60
Tyr Leu Glu Gly Cys Pro Ser Gly Val Glu Pro Phe Phe Ile Pro Val
 65                  70                  75                  80

Ala Lys Ser Cys Asp Cys Ile Lys Cys Lys Thr Asp Asn Thr Asp Cys
                 85                  90                  95

Asp Arg Ile Ser Met Ala Thr Pro Ser Cys Ile Val Asn Pro Leu Glu
                100                 105                 110

Met
```

(2) INFORMATION FOR SEQ ID NO:48:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Ser Leu Met Gln Pro Cys Gln Pro Ile Asn Gln Thr Val Ser Leu Glu
 1                   5                  10                  15

Lys Glu Gly Cys Pro Thr Cys Leu Val Ile Gln Thr Pro Ile Cys Ser
                 20                  25                  30

Gly His Cys Val Thr Lys Glu Pro Val Phe Lys Ser Pro Phe Ser Thr
                 35                  40                  45

Val Ile Gln His Val Cys Thr Tyr Arg Asp Val Arg Tyr Glu Thr Ile
                 50                  55                  60

Arg Leu Pro Asp Cys Pro Pro Trp Val Asp Pro His Val Thr Tyr Pro
 65                  70                  75                  80

Val Ala Leu Ser Cys Asp Cys Ser Leu Cys Asn Met Asp Thr Ser Asp
                 85                  90                  95

Cys Thr Ile Glu Ser Leu Gln Pro Asp Phe Cys Ile Thr Gln Arg Val
                100                 105                 110

Leu Thr Asp Gly Asp Met Trp
        115
```

(2) INFORMATION FOR SEQ ID NO:49:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Asn Ser Cys Glu Leu Thr Asn Ile Thr Ile Ala Ile Glu Lys Glu Glu
 1                   5                  10                  15

Cys Arg Phe Cys Ile Ser Ile Asn Thr Thr Trp Cys Ala Gly Tyr Cys
                 20                  25                  30

Tyr Thr Arg Asp Leu Val Tyr Lys Asp Pro Ala Arg Pro Asn Ile Gln
                 35                  40                  45

Lys Thr Cys Thr Phe Lys Glu Leu Val Tyr Glu Thr Val Lys Val Pro
                 50                  55                  60

Gly Cys Ala His His Ala Asp Ser Leu Tyr Tyr Pro Val Ala Thr
 65                  70                  75                  80

Ala Cys His Cys Gly Lys Cys Asn Ser Asp Ser Thr Asp Cys Thr Val
                 85                  90                  95
```

Arg Gly Leu Gly Pro Ser Tyr Cys Ser Phe Gly Asp Met Lys Glu
            100                 105                 110

(2) INFORMATION FOR SEQ ID NO:50:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Ser Cys Glu Leu Thr Asn Ile Thr Ile Thr Val Glu Lys Glu Cys
1               5                   10                  15

Ser Phe Cys Ile Ser Ile Asn Thr Thr Trp Cys Ala Gly Tyr Cys Tyr
                20                  25                  30

Thr Arg Asp Leu Val Tyr Lys Asp Pro Ala Arg Pro Asn Ile Gln Lys
                35                  40                  45

Thr Cys Thr Phe Lys Glu Leu Val Tyr Glu Thr Val Lys Val Pro Gly
            50                  55                  60

Cys Ala His His Ala Asp Ser Leu Tyr Thr Tyr Pro Val Ala Thr Glu
65                  70                  75                  80

Cys His Cys Gly Lys Cys Asp Ser Asp Ser Thr Asp Cys Thr Val Arg
                    85                  90                  95

Gly Leu Gly Pro Ser Tyr Cys Ser Phe Ser Asp Ile Glu Arg
            100                 105                 110

(2) INFORMATION FOR SEQ ID NO:51:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

Ser Cys Glu Leu Thr Asn Ile Thr Ile Thr Val Glu Lys Glu Cys
1               5                   10                  15

Gly Phe Cys Ile Ser Ile Asn Thr Thr Trp Cys Ala Gly Tyr Cys Tyr
                20                  25                  30

Thr Arg Asp Leu Val Tyr Arg Asp Pro Ala Arg Pro Asn Ile Gln Lys
                35                  40                  45

Thr Cys Thr Phe Lys Glu Leu Val Tyr Glu Thr Val Lys Val Pro Gly
            50                  55                  60

Cys Ala His His Ala Asp Ser Leu Tyr Thr Tyr Pro Val Ala Thr Glu
65                  70                  75                  80

Cys His Cys Ser Lys Cys Asp Ser Asp Ser Thr Asp Cys Thr Val Arg
                    85                  90                  95

Gly Leu Gly Pro Ser Tyr Cys Ser Phe Arg Glu Ile Lys Glu
            100                 105                 110

(2) INFORMATION FOR SEQ ID NO:52:

(i) SEQUENCE CHARACTERISTICS:
        (A) LENGTH: 111 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:52:

Asn Ser Cys Glu Leu Thr Asn Ile Thr Ile Thr Val Glu Lys Glu Glu
1               5                   10                  15

Cys Asn Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Asn Ile Gln
            35                  40                  45

Lys Thr Cys Thr Phe Lys Glu Leu Val Tyr Glu Thr Val Lys Val Pro
        50                  55                  60

Gly Cys Ala His His Ala Asp Ser Leu Tyr Thr Tyr Pro Val Ala Thr
65                  70                  75                  80

Glu Cys His Cys Gly Lys Cys Asp Ser Asp Ser Thr Asp Cys Thr Val
                85                  90                  95

Arg Gly Leu Gly Pro Ser Tyr Cys Ser Phe Ser Glu Met Lys Glu
            100                 105                 110

(2) INFORMATION FOR SEQ ID NO:53:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Ser Cys Glu Leu Thr Asn Ile Thr Ile Ser Val Glu Lys Glu Glu Cys
1               5                   10                  15

Arg Phe Cys Ile Ser Ile Asn Thr Thr Trp Cys Glu Gly Tyr Cys Tyr
                20                  25                  30

Thr Arg Asp Leu Val Tyr Lys Asp Pro Ala Arg Pro Asn Thr Gln Lys
            35                  40                  45

Val Cys Thr Phe Lys Glu Leu Val Tyr Glu Thr Ile Arg Leu Pro Gly
        50                  55                  60

Cys Ala Arg His Ser Asp Ser Leu Tyr Thr Tyr Pro Val Ala Thr Glu
65                  70                  75                  80

Cys His Cys Gly Lys Cys Asp Ser Asp Ser Thr Asp Cys Thr Val Arg
                85                  90                  95

Gly Leu Gly Pro Ser Tyr Cys Ser Phe Gly Glu Met Lys Glu
            100                 105                 110

(2) INFORMATION FOR SEQ ID NO:54:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

Phe Cys Ile Pro Thr Glu Tyr Met Met His Val Glu Arg Lys Glu Cys
1               5                   10                  15

Ala Tyr Cys Leu Thr Ile Asn Thr Thr Val Cys Ala Gly Tyr Cys Met
                20                  25                  30

Thr Arg Asp Val Asn Gly Lys Leu Phe Leu Pro Lys Tyr Ala Leu Ser
```

```
                    35                  40                  45
Gln Asp Val Cys Thr Tyr Arg Asp Met Tyr Lys Thr Ala Glu Ile Pro
 50                  55                  60
Gln Cys Pro Arg His Val Thr Pro Tyr Phe Ser Tyr Pro Val Ala Ile
 65                  70                  75                  80
Ser Cys Lys Cys Gly Lys Cys Asn Thr Asp Tyr Ser Asp Cys Ile His
                     85                  90                  95
Glu Ala Ile Lys Thr Asn Tyr Cys Thr Lys Pro Gln Lys Ser Tyr Met
                    100                 105                 110
Val Gly Phe Ser Ile
                115
```

(2) INFORMATION FOR SEQ ID NO:55:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Phe Cys Ile Pro Thr Glu Tyr Met Met His Val Glu Arg Lys Glu Cys
 1                   5                  10                  15
Ala Tyr Cys Leu Thr Ile Asn Ser Thr Ile Cys Ala Gly Tyr Cys Met
                     20                  25                  30
Thr Arg Asp Phe Asp Gly Lys Leu Phe Leu Pro Lys Tyr Ala Leu Ser
                    35                  40                  45
Gln Asp Val Cys Thr Tyr Arg Asp Met Tyr Lys Thr Val Glu Ile Pro
 50                  55                  60
Gln Cys Pro His His Val Thr Pro Tyr Phe Ser Tyr Pro Val Ala Ile
 65                  70                  75                  80
Ser Cys Lys Cys Gly Lys Cys Asp Thr Asp Tyr Ser Asp Cys Ile His
                     85                  90                  95
Glu Ala Ile Lys Thr Asn Tyr Cys Thr Lys Pro Glu Lys Ser Tyr
                    100                 105                 110
```

(2) INFORMATION FOR SEQ ID NO:56:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Phe Cys Ile Pro Thr Glu Tyr Thr Met Tyr Val Asp Arg Arg Glu Cys
 1                   5                  10                  15
Ala Tyr Cys Leu Thr Ile Asn Thr Thr Ile Cys Ala Gly Tyr Cys Met
                     20                  25                  30
Thr Arg Asp Ile Asn Gly Lys Leu Phe Leu Pro Lys Tyr Ala Leu Ser
                    35                  40                  45
Gln Asp Val Cys Thr Tyr Arg Asp Ile Tyr Arg Thr Val Glu Ile Pro
 50                  55                  60
Gln Cys Pro His His Val Thr Pro Tyr Phe Ser Phe Pro Val Ala Val
 65                  70                  75                  80
Ser Cys Lys Cys Gly Lys Cys Asn Thr Asp Asn Ser Asp Cys Ile His
```

85                  90                  95
Glu Ala Val Arg Thr Asn Tyr Cys Thr Lys Pro Gln Ser Phe Tyr Leu
                100                 105                 110

Gly Gly Phe Ser Tyr
        115

(2) INFORMATION FOR SEQ ID NO:57:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Phe Cys Ile Pro Thr Glu Tyr Met Met Tyr Val Asp Arg Arg Glu Cys
1               5                   10                  15

Ala Tyr Cys Leu Thr Ile Asn Thr Thr Ile Cys Ala Gly Tyr Cys Met
                20                  25                  30

Thr Arg Asp Ile Asn Gly Lys Leu Phe Leu Pro Lys Tyr Ala Leu Ser
                35                  40                  45

Gln Asp Val Cys Thr Tyr Arg Asp Thr Tyr Arg Thr Val Glu Ile Pro
    50                  55                  60

Gln Cys Pro His His Val Ala Pro Tyr Phe Ser Tyr Pro Val Ala Leu
65                  70                  75                  80

Ser Cys Lys Cys Gly Lys Cys Asn Thr Asp Tyr Ser Asp Cys Thr His
                85                  90                  95

Glu Ala Val Lys Thr Asn Tyr Cys Thr Lys Pro Gln Thr Phe Tyr Leu
                100                 105                 110

Gly Gly Phe Ser Gly
        115

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

AGCTGTCCTG GAGCTAGGAA TCT                                                      23

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CTAGCCTAGA AGCTCTGACT GTC                                                      23

(2) INFORMATION FOR SEQ ID NO:60:

(i) SEQUENCE CHARACTERISTICS:
        (A) LENGTH: 49 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:60:

AGCTGTCCTG GAGCTAGGAA TCTCTGTACG GAAGTGTTAC TTCTGCTCT              49

(2) INFORMATION FOR SEQ ID NO:61:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:61:

CTAGCCTAGA AGCTCTGACT GTCCTAGTTG TGGTTTGTCC AAACTCATC              49

(2) INFORMATION FOR SEQ ID NO:62:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:62:

AACCGCCCTG AACACATCCT GCAAAAAGCC CAGA                              34

(2) INFORMATION FOR SEQ ID NO:63:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:63:

GTGGCTCTCA GCTGTCAATG CGCGCTCTGC CGCAGATCTA CCACTGACTG CGGGGTCCCT  60

AAGGACCAC                                                         69

(2) INFORMATION FOR SEQ ID NO:64:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:64:

CCACACGGAT CCGAGCTCTT AGCGGGGGTC ATCACAGGTC AAGGGGTGGT CCTTAGGGAC  60

CCCGCAGTCA GT                                                     72

(2) INFORMATION FOR SEQ ID NO:65:

(i) SEQUENCE CHARACTERISTICS:
            (A) LENGTH: 45 base pairs
            (B) TYPE: nucleic acid
```

(C) STRANDEDNESS: single
            (D) TOPOLOGY: linear (ii) MOLECULE TYPE: cDNA (xi) SEQUENCE DESCRIPTION: SEQ ID NO:65:

ACTGTCCGGG GCTTGGGTCC CTTGACCTGT GATGACCCCC GCTTC                45

(2) INFORMATION FOR SEQ ID NO:66:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:66:

GGGACCCAAG CCGCGGACAG TACAGTCAGT ACTGTCGCTG TCGCAGAG             48

(2) INFORMATION FOR SEQ ID NO:67:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:67:

CCCAAGACCG CGGACAGTGC AGTCAGTGGT AGATCTGCG                       39

(2) INFORMATION FOR SEQ ID NO:68:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:68:

TGCACTGTCC GCGGTCTTGG CCCAAGCTAT TGCAGCTTCG GCGAATTCCA GGACTCCTCT    60

TCCTCAAAGG CC                                                       72

(2) INFORMATION FOR SEQ ID NO:69:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:69:

GATCCTTAAG ATTTGTGATA ATAACAAGTA CTGCA                           35

(2) INFORMATION FOR SEQ ID NO:70:

(i) SEQUENCE CHARACTERISTICS:
            (A) LENGTH: 81 base pairs
            (B) TYPE: nucleic acid
            (C) STRANDEDNESS: single
            (D) TOPOLOGY: linear -continued (ii) MOLECULE TYPE: cDNA (xi) SEQUENCE DESCRIPTION: SEQ ID NO:70:

GGTTCTGGTA CCGATGACGA TGACAAGTCT AAAGAACCGC TGCGGCCGCG TTGCCGCCCC          60

ATCAATGCCA CCCTGGCTGT G                                                   81

(2) INFORMATION FOR SEQ ID NO:71:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:71:

CCCACCGGAT CCTTAAGATT TGTGATAATA ACAAGTACTG CA                            42

(2) INFORMATION FOR SEQ ID NO:72:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:72:

TGCTTCTCTA GAGCATATCC AACTCCATTG AGATCTAAGA AGACTATGTT GGTCCAAAAG          60

CAAGTCACTA GTGAGTCCAC TTGC                                                84

(2) INFORMATION FOR SEQ ID NO:73:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:73:

CCGGCTGTTG TCCTACCATG ACACGTGTGC TGCA                                     34

(2) INFORMATION FOR SEQ ID NO:74:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:74:

CTGTAGCGTG CATTCCGGAC TATCCTGCAC ATCAGGAGC                                 39

(2) INFORMATION FOR SEQ ID NO:75:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:75:

CCATTGAGAT CTAAGAAGAC TATGTTGGTC CAAAAGGACG TCACTAGTGA GTCCACTTGC              60

(2) INFORMATION FOR SEQ ID NO:76:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:76:

ACAAGTACTG CAGTGACAAG CAGTGTGTTG CTCCACTTTG AAACC                              45

(2) INFORMATION FOR SEQ ID NO:77:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:77:

GCACACGTGT CATGGTAGGA CAACAG                                                  26

(2) INFORMATION FOR SEQ ID NO:78:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

GATCTGCTAG CTAAGCA                                                            17

(2) INFORMATION FOR SEQ ID NO:79:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:79:

CTAGTGCTTA GCTAGCA                                                            17

(2) INFORMATION FOR SEQ ID NO:80:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

GATCTAAGAA GACTATGCTT GTACAATGTA ACGTTA                                       36

(2) INFORMATION FOR SEQ ID NO:81:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

CTAGTAACGT TACATTGTAC AAGCATAGTC TTCTTA                    36

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

GGACTGTACA ACAAGTAGTA                                  20

(2) INFORMATION FOR SEQ ID NO:83:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

GATCTACTAC TTGTTGTACA GTCCGC                            26

(2) INFORMATION FOR SEQ ID NO:84:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

TGCCGCAGAT CTACTACTTG CTGCGGGGGT CCCAAGGACC AC              42

(2) INFORMATION FOR SEQ ID NO:85:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

CCATTGAGAT CTAAGAAGAC TATGTTGGTC CAAAAGAACG TCACTAGTGA GTCC      54

(2) INFORMATION FOR SEQ ID NO:86:

(i) SEQUENCE CHARACTERISTICS:
        (A) LENGTH: 57 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

ACAAGTACTG CAGTGACACG CCGTGTGGTT CTCACATTTA AAACCCCCCA TTACTGT            57

(2) INFORMATION FOR SEQ ID NO:87:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

CCGGCTATTG TCCTACTATG ACGCGTTGTC TGCA                                    34

(2) INFORMATION FOR SEQ ID NO:88:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:88:

GACAACGCGT CATAGTAGGA CAATAG                                             26

(2) INFORMATION FOR SEQ ID NO:89:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

CTGTGCTATA AG                                                            12

(2) INFORMATION FOR SEQ ID NO:90:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

GTCCTTATAG CACAGATCC                                                     19

(2) INFORMATION FOR SEQ ID NO:91:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:91:

CTTAATACGA CTCACTATAG GCTAGCCTCG AG                          32

(2) INFORMATION FOR SEQ ID NO:92:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:92:

CATCCCGCGG CACCTAGGAC AAAGCGGCTC CTTGGATGCC CATGT            45

(2) INFORMATION FOR SEQ ID NO:93:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Ala Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

(2) INFORMATION FOR SEQ ID NO:94:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Cys Cys Met Gly Cys Cys Phe Ser Arg Ala Tyr Pro Thr Pro

```
            50                  55                  60
Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
        115

(2) INFORMATION FOR SEQ ID NO:95:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

Met Asp Tyr Tyr Arg Lys Tyr Ala Ala Ile Phe Leu Val Thr Leu Ser
  1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
                 35                  40                  45

Ile Leu Gln Cys Cys Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
        115

(2) INFORMATION FOR SEQ ID NO:96:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Met Asp Tyr Tyr Arg Lys Tyr Ala Ala Ile Phe Leu Val Thr Leu Ser
  1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
                 35                  40                  45

Ile Leu Gln Cys Met Gly Cys Cys Phe Cys Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
```

```
                     85                  90                  95
Gly Phe Lys Val Glu Asn His Thr Ala Cys His Cys Ser Thr Cys Tyr
                100                 105                 110
Tyr His Lys Ser
        115

(2) INFORMATION FOR SEQ ID NO:97:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Cys Ala Tyr Pro Thr Pro
50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
                100                 105                 110

Tyr His Lys Ser
        115

(2) INFORMATION FOR SEQ ID NO:98:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Cys Pro Thr Pro
50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
                100                 105                 110

Tyr His Lys Ser
```

(2) INFORMATION FOR SEQ ID NO:99:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
Met Asp Tyr Tyr Arg Lys Tyr Ala Ala Ile Phe Leu Val Thr Leu Ser
  1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Cys Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
            115
```

(2) INFORMATION FOR SEQ ID NO:100:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

```
Met Asp Tyr Tyr Arg Lys Tyr Ala Ala Ile Phe Leu Val Thr Leu Ser
  1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Cys Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
            115
```

(2) INFORMATION FOR SEQ ID NO:101:

(i) SEQUENCE CHARACTERISTICS:

(A) LENGTH: 116 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:101:

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
50                      55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Ala Tyr
            100                 105                 110

Tyr His Lys Ser
        115
```

(2) INFORMATION FOR SEQ ID NO:102:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
50                      55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

(2) INFORMATION FOR SEQ ID NO:103:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Cys Val Glu Asn His Thr Ala Cys His Cys Ser Thr Cys Tyr
                100                 105                 110

Tyr His Lys Ser
        115

(2) INFORMATION FOR SEQ ID NO:104:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Cys Glu Asn His Thr Ala Cys His Cys Ser Thr Cys Tyr
                100                 105                 110

Tyr His Lys Ser
        115

(2) INFORMATION FOR SEQ ID NO:105:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Met Asp Tyr Tyr Arg Lys Tyr Ala Ala Ile Phe Leu Val Thr Leu Ser
1               5                   10                  15

```
Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
 50                      55                  60

Leu Arg Ser Lys Lys Thr Met Leu Val Gln Lys Asn Val Thr Ser Glu
 65                  70                  75                  80

Ser Thr Ala Cys
```

(2) INFORMATION FOR SEQ ID NO:106:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

```
Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Tyr Cys Tyr Thr Cys Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                 85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
        115                 120                 125

Glu
```

(2) INFORMATION FOR SEQ ID NO:107:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

```
Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Cys Gly
            35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80
```

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu (2) INFORMATION FOR SEQ ID NO:108:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Cys Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65              70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu (2) INFORMATION FOR SEQ ID NO:109:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65              70                  75                  80

Val Pro Gly Cys Ala His His Ala Asp Ser Leu Tyr Thr Tyr Pro Val

```
                    85                  90                  95
Ala Thr Gln Cys His Cys Gly Lys Cys Asp Ser Asp Ser Cys Asp Cys
                100                 105                 110

Thr Val Arg Gly Leu Gly Pro Ser Tyr Cys Ser Phe Gly Glu Met Lys
        115                 120                 125

Glu
```

(2) INFORMATION FOR SEQ ID NO:110:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
                20                  25                  30

Glu Gly Cys Gly Phe Cys Ile Thr Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Cys Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
        115                 120                 125

Glu
```

(2) INFORMATION FOR SEQ ID NO:111:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:111:

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
                20                  25                  30

Glu Gly Cys Gly Phe Cys Ile Thr Ile Asn Thr Thr Trp Cys Ala Gly
            35                  40                  45

Tyr Cys Tyr Cys Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95
```

```
Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu (2) INFORMATION FOR SEQ ID NO:112:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:112:

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Tyr Cys Tyr Thr Arg Cys Leu Val Tyr Lys Asp Pro Ala Arg Pro Lys
        50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu (2) INFORMATION FOR SEQ ID NO:113:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:113:

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
            35                  40                  45

Tyr Cys Tyr Thr Arg Asp Leu Val Tyr Cys Asp Pro Ala Arg Pro Lys
        50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110
```

```
Thr Val Arg Gly Leu Gly Pro Ser Tyr Cys Ser Phe Gly Glu Met Lys
        115                 120                 125
Glu (2) INFORMATION FOR SEQ ID NO:114:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Val Glu Lys
            20                  25                  30

Glu Gly Cys Gly Phe Cys Ile Thr Ile Asn Thr Thr Trp Cys Ala Gly
        35                  40                  45

Tyr Cys Tyr Thr Arg Asp Leu Cys Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
        115                 120                 125
Glu (2) INFORMATION FOR SEQ ID NO:115:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:115:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Cys Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
```

```
            115                 120                 125
Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:116:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:116:

Met Glu Met Phe Gln Gly Leu Leu Leu Leu Leu Leu Ser Met Gly
1                   5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Cys Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:117:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:117:

Met Glu Met Phe Gln Gly Leu Leu Leu Leu Leu Leu Ser Met Gly
1                   5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
```

```
                  50                  55                  60
Leu Gln Gly Val Leu Pro Ala Leu Pro Gln Val Cys Cys Asn Tyr Arg
 65                  70                  75                  80

Asp Val Arg Phe Glu Ser Ile Arg Leu Pro Gly Cys Pro Arg Gly Val
                     85                  90                  95

Asn Pro Val Val Ser Tyr Ala Val Ala Leu Ser Cys Gln Cys Ala Leu
                    100                 105                 110

Cys Arg Arg Ser Thr Thr Asp Cys Gly Gly Pro Lys Asp His Pro Leu
                    115                 120                 125

Thr Cys Asp Asp Pro Arg Phe Gln Asp Ser Ser Ser Lys Ala Pro
                130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:118:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:118:

Met Glu Met Phe Gln Gly Leu Leu Leu Leu Leu Leu Ser Met Gly
  1                   5                  10                  15

Gly Thr Trp Ala Ser Lys Glu Pro Leu Arg Pro Arg Cys Arg Pro Ile
                     20                  25                  30

Asn Ala Thr Leu Ala Val Glu Lys Glu Gly Cys Pro Val Cys Ile Thr
                     35                  40                  45

Val Asn Thr Thr Ile Cys Cys Gly Tyr Cys Pro Thr Met Thr Arg Val
 50                  55                  60

Leu Gln Gly Val Leu Pro Ala Leu Pro Gln Val Cys Cys Asn Tyr Arg
 65                  70                  75                  80

Asp Val Arg Phe Glu Ser Ile Arg Leu Pro Gly Cys Pro Arg Gly Val
                     85                  90                  95

Asn Pro Val Val Ser Tyr Ala Val Ala Leu Ser Cys Gln Cys Ala Leu
                    100                 105                 110

Cys Arg Arg Ser Thr Thr Asp Cys Gly Gly Pro Lys Asp His Pro Leu
                    115                 120                 125

Thr Cys Asp Asp Pro Arg Phe Gln Asp Ser Ser Ser Lys Ala Pro
                130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:119:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide
```

-continued (xi) SEQUENCE DESCRIPTION: SEQ ID NO:119:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Cys Cys Ala Gly Tyr Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:120:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:120:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Cys Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:121:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:121:

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Cys Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln
                165
```

(2) INFORMATION FOR SEQ ID NO:122:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Cys Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110
```

```
Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
            165

(2) INFORMATION FOR SEQ ID NO:123:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                  55                  60

Leu Cys Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
            85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
            165

(2) INFORMATION FOR SEQ ID NO:124:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45
```

```
Val Asn Thr Thr Ile Cys Ala Gly Tyr Cys Pro Thr Met Thr Arg Cys
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:125:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
                 20                  25                  30

Asn Ala Thr Leu Ala Val Glu Lys Glu Gly Cys Pro Val Cys Ile Thr
                 35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Cys Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

(2) INFORMATION FOR SEQ ID NO:126:

(i) SEQUENCE CHARACTERISTICS:
        (A) LENGTH: 141 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:126:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Cys
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
    130                 135                 140

(2) INFORMATION FOR SEQ ID NO:127:

(i) SEQUENCE CHARACTERISTICS:
         (A) LENGTH: 141 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:127:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Cys Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
    130                 135                 140

(2) INFORMATION FOR SEQ ID NO:128:

(i) SEQUENCE CHARACTERISTICS:
         (A) LENGTH: 141 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:128:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
        50                  55                  60

Leu Gln Ala Val Leu Pro Pro Leu Pro Gln Val Cys Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
            130                 135                 140

(2) INFORMATION FOR SEQ ID NO:129:

(i) SEQUENCE CHARACTERISTICS:
            (A) LENGTH: 141 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:129:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Cys Gly Tyr Cys Pro Thr Met Met Arg Val
        50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
            130                 135                 140

(2) INFORMATION FOR SEQ ID NO:130:

(i) SEQUENCE CHARACTERISTICS:
            (A) LENGTH: 141 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:130:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Cys Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
            115                 120                 125

Thr Cys Asp His Pro Gln Leu Ser Gly Leu Leu Phe Leu
        130                 135                 140

(2) INFORMATION FOR SEQ ID NO:131:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:131:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Cys Asp Cys Gly Gly Pro Lys Asp His Pro Leu
            115                 120                 125

Thr Cys Asp His Pro Gln Leu Ser Gly Leu Leu Phe Leu
        130                 135                 140

(2) INFORMATION FOR SEQ ID NO:132:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:132:

```
Met Glu Met Leu Gln Gly Leu Leu Leu Leu Leu Leu Ser Met Gly
 1               5                  10                  15

Gly Ala Trp Ala Ser Arg Glu Pro Leu Arg Pro Trp Cys His Pro Ile
                20                  25                  30

Asn Ala Ile Leu Ala Val Glu Lys Glu Gly Cys Pro Val Cys Ile Thr
             35                  40                  45

Val Asn Thr Thr Ile Cys Ala Gly Tyr Cys Pro Cys Met Met Arg Val
 50                  55                  60

Leu Gln Ala Val Leu Pro Pro Leu Pro Gln Val Val Cys Thr Tyr Arg
 65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
                130                 135                 140
```

(2) INFORMATION FOR SEQ ID NO:133:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:133:

```
Met Glu Met Leu Gln Gly Leu Leu Leu Leu Leu Leu Ser Met Gly
 1               5                  10                  15

Gly Ala Trp Ala Ser Arg Glu Pro Leu Arg Pro Trp Cys His Pro Ile
                20                  25                  30

Asn Ala Ile Leu Ala Val Glu Lys Glu Gly Cys Pro Val Cys Ile Thr
             35                  40                  45

Val Asn Thr Thr Ile Cys Ala Gly Tyr Cys Pro Thr Met Cys Arg Val
 50                  55                  60

Leu Gln Ala Val Leu Pro Pro Leu Pro Gln Val Val Cys Thr Tyr Arg
 65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
                130                 135                 140
```

(2) INFORMATION FOR SEQ ID NO:134:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:134:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
        50                  55                  60

Leu Cys Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
            130                 135                 140

(2) INFORMATION FOR SEQ ID NO:135:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:135:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
        50                  55                  60

Leu Gln Ala Val Leu Pro Pro Leu Pro Cys Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu
            130                 135                 140

(2) INFORMATION FOR SEQ ID NO:136:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:136:

```
Met Glu Met Phe Gln Gly Leu Leu Leu Leu Leu Leu Ser Met Gly
1               5                   10                  15

Gly Thr Trp Ala Ser Lys Glu Pro Leu Cys Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Cys Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys
130                 135                 140
```

(2) INFORMATION FOR SEQ ID NO:137:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:137:

```
Met Glu Met Phe Gln Gly Leu Leu Leu Leu Leu Leu Ser Met Gly
1               5                   10                  15

Gly Thr Trp Ala Ser Lys Glu Pro Leu Cys Asn Ser Cys Glu Leu Thr
            20                  25                  30

Asn Ile Thr Ile Ala Val Glu Lys Glu Gly Cys Gly Phe Cys Ile Thr
            35                  40                  45

Ile Asn Thr Thr Trp Cys Ala Gly Cys Cys Tyr Thr Arg Asp Leu Val
50                  55                  60

Tyr Lys Asp Pro Ala Arg Pro Lys Ile Gln Lys Thr Cys Thr Phe Lys
65                  70                  75                  80

Glu Leu Val Tyr Glu Thr Val Arg Val Pro Gly Cys Ala His His Ala
                85                  90                  95

Asp Ser Leu Tyr Thr Tyr Pro Val Ala Thr Gln Cys His Cys Gly Lys
                100                 105                 110

Cys Asp Ser Asp Ser Thr Asp Cys Thr Val Arg Gly Leu Gly Pro Ser
            115                 120                 125

Tyr Cys Ser Phe Gly Glu Met Lys Glu
130                 135
```

(2) INFORMATION FOR SEQ ID NO:138:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

```
Met Glu Met Phe Gln Gly Leu Leu Leu Leu Leu Leu Ser Met Gly
1               5                   10                  15

Gly Thr Trp Ala Ser Lys Glu Pro Leu Cys Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Cys Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Asp Ser Asp Ser Thr Asp Cys Thr Val Arg Gly Leu Gly Pro Ser
            115                 120                 125

Tyr Cys Ser Phe Gly Glu Met Lys Glu Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln
                165
```